United States Patent
Kadysh et al.

(10) Patent No.: US 12,053,452 B2
(45) Date of Patent: Aug. 6, 2024

(54) COMPOSITIONS COMPRISING NON-RACEMIC MIXTURES OF (R)- AND (S)-3,4-METHYLENEDIOXYMETHAMPHETAMINE OR (R) AND (S) N-METHYL-1,3-BENZODIOXOLYLBUTANAMINE AND USES THEREOF

(71) Applicant: PharmAla Biotech Inc., Vancouver (CA)

(72) Inventors: Nicholas Kadysh, Vancouver (CA); Leonard Howell, Atlanta, GA (US); Harpreet Kaur, Nanaimo (CA)

(73) Assignee: PHARMALA BIOTECH INC., Vancouver (CA)

( * ) Notice: Subject to any disclaimer, the term of this patent is extended or adjusted under 35 U.S.C. 154(b) by 0 days.

(21) Appl. No.: 18/117,723

(22) Filed: Mar. 6, 2023

(65) Prior Publication Data
US 2023/0201159 A1 Jun. 29, 2023

Related U.S. Application Data

(63) Continuation of application No. PCT/CA2022/051269, filed on Aug. 22, 2022.

(60) Provisional application No. 63/235,460, filed on Aug. 20, 2021, provisional application No. 63/298,820, filed on Jan. 12, 2022.

(51) Int. Cl.
*A61K 31/357* (2006.01)
*A61P 25/00* (2006.01)

(52) U.S. Cl.
CPC ............ *A61K 31/357* (2013.01); *A61P 25/00* (2018.01)

(58) Field of Classification Search
CPC .............................. A61K 31/357; A61K 31/36
See application file for complete search history.

(56) References Cited

U.S. PATENT DOCUMENTS

| | | |
|---|---|---|
| 2023/0097530 A1 | 3/2023 | Short et al. |
| 2023/0129723 A1 | 4/2023 | Short et al. |
| 2023/0218568 A1 | 7/2023 | Liechti |

FOREIGN PATENT DOCUMENTS

| | | |
|---|---|---|
| WO | 2022150525 A1 | 7/2022 |
| WO | 2022232948 A1 | 11/2022 |
| WO | 2022232949 A1 | 11/2022 |
| WO | 2022235500 A1 | 11/2022 |
| WO | 2022235514 A1 | 11/2022 |
| WO | 2022235529 A1 | 11/2022 |
| WO | 2022235530 A1 | 11/2022 |
| WO | 2022235531 A1 | 11/2022 |
| WO | 2022256720 A2 | 12/2022 |
| WO | WO 2022256720 A2 † | 12/2022 |

OTHER PUBLICATIONS

Search Report and Written Opinion dated Dec. 7, 2022 in respect of PCT/CA2022/051269.
Fagan et al., "Ecstasy tablets: Rapid identification and determination of enantiomeric excess of MDMA", Forensic Chemistry 26 (2011) 100381.
Dunlap et al., "Dark Classics in Chemical Neuroscience: 3,4-Methylenedioxymethamphetamine", ACS Chem. Neurosci. 2018, 9, 22408-2427.
Llabres et al., "Molecular basis of the selective binding of MDMA enantiomers to the alpha4beta2 nictonic receptor subtype: Synthesis, pharmacological evaluation and mechanistic studies", European Journal of Medicinal Chemistry 81 (2014) 35-46.
Curry et al., "Separating the agony from ecstasy: R(-)-3,4-methylenedioxymethamphetamine has prosocial and therapeutic-like effects without signs of neurotoxicity in mice", Neuropharmacology 128 (2018) 196-206.

(Continued)

*Primary Examiner* — Sahar Javanmard
(74) *Attorney, Agent, or Firm* — Bereskin & Parr LLP/S.E.N.C.R.L., s.r.l.; Sandra Marone

(57) ABSTRACT

The present application includes a composition comprising a non-racemic mixture a compound of Formula (R)-I, or a salt and/or solvate thereof, and (S)-I, or a salt and/or solvate thereof:

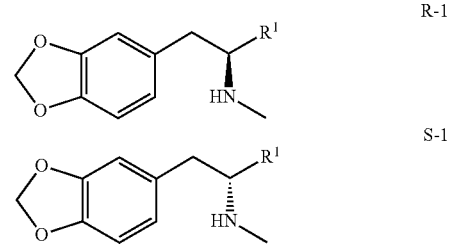

wherein (R)-I, or a salt and/or solvate thereof, is present in the composition in a greater amount by enantiomeric equivalents, relative to (S)-I, or a salt and/or solvate thereof. Also included are methods of using these compositions for treating, for example, a psychiatric disorder. The compounds of Formula (R)-I and (S)-I include the enantiomers of 3,4-methylenedioxymethamphetamine (MDMA) and N-methyl-1,3-benzodioxolylbutanamine (MBDB).

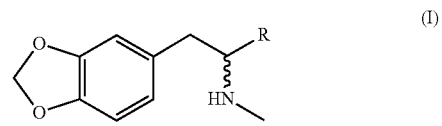

Also included in the present application is a method for treating various diseases, disorders or conditions using a therapeutically effective amount of (R)-MDMA, or a pharmaceutically acceptable salt and/or solvate thereof.

13 Claims, 24 Drawing Sheets

(56) References Cited

OTHER PUBLICATIONS

Pitts et al., "(±)-MDMA and its enantiomers: potential therapeutic advantages of R(−)MDMA", Psychopharmacology (2018) 235:377-392.

Schmidt et al., "Ecstasy counteracts catalepsy in rates, an anti-parkinsonian effect?", Neuroscience Letters 330 (2002) 251-254.

Huot et al., "Characterization of 3,4-Methylenedioxymethamphetamine (MDMA) Enantiomers In Vitro and in the MPTP-Lesioned Primate: R-MDMA Reduces Severity of Dyskinesia, Whereas S-MDMA Extends Duration of ON-Time", The Journal of Neuroscience, May 11, 2011, 31(19):7190-7198.

Lebsabft et al., "3,4-Methylenedioxymethamphetamine Counteracts Akinesia Enantioselectively in Rat Rotational Behaviour and Catalepsy", SYNAPSE 55:148-155 (2005).

Nichols, "Chemistry and Structure-Activity Relationships of Psychedelics", Curr Topics Behav Neurosci, 2017.

Felim et al., "Synthesis and in Vitro Cytotoxicity Profile of the R-Enantiomer of 3,4-Dihydroxymethamphetamine (R-(-)-HHMA): Comparison with Related Catecholamines", Chem. Res. Toxicol., vol. 23, No. 1, 2010, 211-219.

Setola et al., "3,4-Methylenedioxymethamphetamine (MDMA, "Ecstasy") Induces Fenfluramine-Like Proliferative Actions on Human Cardiac Valvular Interstitial Cells in Vitro", Molecular Pharmacology, 63:1223-1229, 2003.

"A Randomized, Double-Blind, Placebo-Controlled, Multi-Site Phase 3 Study of the Efficacy and Safety of Manualized MDMA-Assisted Psychotherapy for the Treatment of Posttraumatic Stress Disorder of Moderate or Greater Severity", Protocol and Synopsis MAPP2, MAPS Public Benefit Corporation, Mar. 23, 2021.

Office Action Response dated Jan. 26, 2024 in respect of U.S. Appl. No. 18/230,142.

Comments on Statement of Reasons for Allowance dated Feb. 13, 2024 in respect of U.S. Appl. No. 18/230,142.

Schmidt, W. J., Mayerhofer, A., Meyer, A., &Kovar, K. A. (2002). Ecstasy counteracts catalepsy in rats, an anti-parkinsonian effect?. Neuroscience letters, 330(3), 251-254. doi.org/10.1016/s0304-3940(02)00823-6 ("Schmidt 2002").†

Huot, P., Johnston, T. H., Lewis, K. D., Koprich, J. B., Reyes, M. G., Fox, S. H., Piggott, M. J., &Brotchie, J. M. (2011). Characterization of 3,4-methylenedioxy-methamphetamine (MDMA) enantiomers in vitro and in the MPTP-lesioned primate: R-MDMA reduces severity of dyskinesia, whereas S-MDMA extends duration of ON-time. The Journal of neuroscience, 31(19). 7190-7198. doi.org/10.1523/JNEUROSCI.1171-11.2011 ("Huot 2011").†

U.S. Appl. No. 63/196,226.†

Mitchell, J. M., et al. (2021). MDMA-assisted therapy for severe PTSD: a randomized, double-blind, placebo-controlled phase 3 study. Nature medicine, 27(6), 1025-1033. doi.org/10.1038/841591-021-01336-3 ("Mitchell 2021").†

† cited by third party

Effect of increased doses of Racemic MDMA injection on LMA in C57 and BTBR mice

COMPOSITIONS COMPRISING NON-RACEMIC MIXTURES OF (R)- AND (S)-3,4- METHYLENEDIOXY-METHAMPHETAMINE OR (R) AND (S) N-METHYL-1,3- BENZODIO-XOLYLBUTANAMINE AND USES THEREOF

RELATED APPLICATIONS

The present application is a continuation of co-pending International patent application no. PCT/CA2022/051269 filed Aug. 22, 2022 which claims the benefit of priority from U.S. provisional patent application No. 63/235,460 filed on Aug. 20, 2021, and from U.S. provisional patent application No. 63/298,820 filed on Jan. 12, 2022, the contents of each of which are incorporated herein by reference in their entirety.

FIELD

The present application relates to compositions comprising non-racemic mixtures of 3,4-methylenedioxymethamphetamine (MDMA) and N-methyl-1,3-benzodioxolylbutanamine (MBDB) and methods of using these compositions in therapeutic treatments. The present application further comprises various novel therapeutic treatments using (R)-MDMA.

BACKGROUND 3,4-Methylenedioxymethamphetamine (MDMA), commonly known as ecstasy (E) or molly, is a psychoactive drug first developed in 1912 by Merck. MDMA is often used recreationally today. However, an initial use of MDMA was as an adjunct to psychotherapy. More recently, MDMA has been studied in various clinical trials, for example, investigating MDMA-assisted psychotherapy for posttraumatic stress disorder (PTSD), anxiety related to advanced-stage illness, and social anxiety in autistic adults. MDMA has now been granted Breakthrough Therapy Designation for the treatment of PTSD by the United States Food and Drug Administration (FDA).

MDMA is generally available and consumed as a racemate. The racemate of MDMA is also known to have potential for adverse effects such as hyperthermia and neurotoxicity. However, studies have shown qualitative differences in the effects of the isomers of MDMA. Evidence suggests that the R isomer of MDMA may provide an improved therapeutic index while maintaining some of the therapeutic effects of MDMA racemate with a reduced side effect profile (Pitts et al. Psychopharmacology 235, 377-392, 2018, Curry et al. Neuropharmacology. 2018 January; 128: 196-206, Huot et al. Journal of Neuroscience, 2011, 31 (19) 7190-7198, Setola et al. Mol. Pharmacol. 63:1223-1229, 2003). There is a need for further investigations to determined therapeutic potential of the enantiomers of MDMA.

N-methyl-1,3-benzodioxolylbutanamine (MBDB) commonly known as Eden or Methyl-J, is an analogue of MDMA which has an ethyl group instead of a methyl group attached to the alpha carbon next to the amine. Like MDMA, MBDB is also classified as an entactogen. MBDB is also generally available and consumed as a racemate. Therefore, there is also a need for further investigation of the prosocial, therapeutic and toxicological effects of each enantiomer or MBDB.

SUMMARY 3,4-Methylenedioxymethamphetamine (MDMA) is generally administered as a racemate. The effect of the racemate of MDMA in social behaviour in humans has been studied. It is known that the racemate of MDMA exhibits adverse effects such as hyperthermia and neurotoxicity, and has the potential for drug abuse. The R enantiomer of MDMA ((R)-MDMA) has been shown to have prosocial effects with lower risk for adverse effects such as neurotoxicity and hypothermia. However, the S enantiomer of MDMA ((S)-MDMA) is known be the more potent enantiomer and to have the stimulant activity but it exhibits more adverse effects. Use of (R)-MDMA on its own, would result in loss of the stimulant activity and any synergistic effects provided from the S enantiomer.

The Applicant therefore investigates various non-racemic mixtures of the enantiomers of MDMA which comprise a greater amount of the R enantiomer to develop a composition comprising a sufficient amount of the R enantiomer to achieve the desired prosocial effects while decreasing the occurrence of adverse effects, such as hyperthermia and neurotoxicity, of the S enantiomer, yet comprising a sufficient amount of the S enantiomer for therapeutic efficacy. The compositions of the application also have a lower potential for drug abuse. Similar such studies are carried out for the enantiomers of N-methyl-1,3-benzodioxolylbutanamine (MBDB). Through these detailed studies, the Applicant develops a composition comprising an optimum range for the ratio of the two enantiomers of these valuable therapeutic compounds, to provide the desired efficacy yet minimize the undesirable effects associated with the current use of the racemic mixtures.

In the present application, the Applicant also describes new therapeutic uses for the (R)-enantiomer of MDMA and MBDB, including as therapy for autism-spectrum disorders, clinical depression in palliative patients and substance use disorder (e.g., opioid use disorder).

Therefore, the present application includes a composition comprising a non-racemic mixture a compound of Formula (R)-I, or a salt and/or solvate thereof, and (S)-I, or a salt and/or solvate thereof:

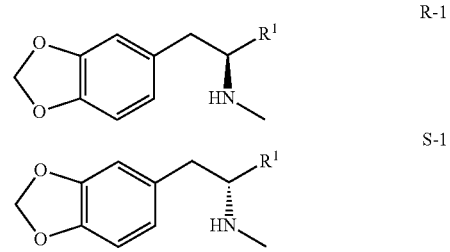

wherein $R^1$ is $CH_3$ or $CH_2CH_3$, and (R)-I, or a salt and/or solvate thereof, is present in the composition in a greater amount by enantiomeric equivalents, relative to (S)-I, or a salt and/or solvate thereof.

The present application also includes a method of reducing adverse side effects of treatment with a racemic mixture of a compound of Formula I, or pharmaceutically acceptable a salt and/or solvate thereof:

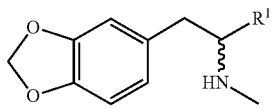

wherein
$R^1$ is selected from $CH_3$ and $CH_2CH_3$,
the method comprising administering a therapeutically effective amount of one or more compositions of the application to a subject in need thereof.

The present application includes a method of treating diseases, disorders or conditions that benefit from treatment with a racemic mixture of a compound of Formula I or a pharmaceutically acceptable salt and/or solvate thereof:

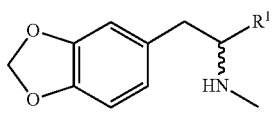

wherein
$R^1$ is selected from $CH_3$ and $CH_2CH_3$,
the method comprising administering a therapeutically effective amount of one or more compositions of the application to a subject in need thereof.

The present application also includes a method for treating diseases, disorders or conditions that benefit from treatment with racemic MDMA, or a pharmaceutically acceptable salt and/or solvate thereof, the method comprising administering a therapeutically effective amount of (R)-MDMA, or a pharmaceutically acceptable salt and/or solvate thereof, to a subject in need thereof Other features and advantages of the present application will become apparent from the following detailed description. It should be understood, however, that the detailed description and the specific examples, while indicating embodiments of the application, are given by way of illustration only and the scope of the claims should not be limited by these embodiments but should be given the broadest interpretation consistent with the description as a whole.

BRIEF DESCRIPTION OF THE DRAWINGS

The present application will be described in greater detail with reference to the attached drawings and Tables in which.

DETAILED DESCRIPTION

I. Definitions

Figure 1:
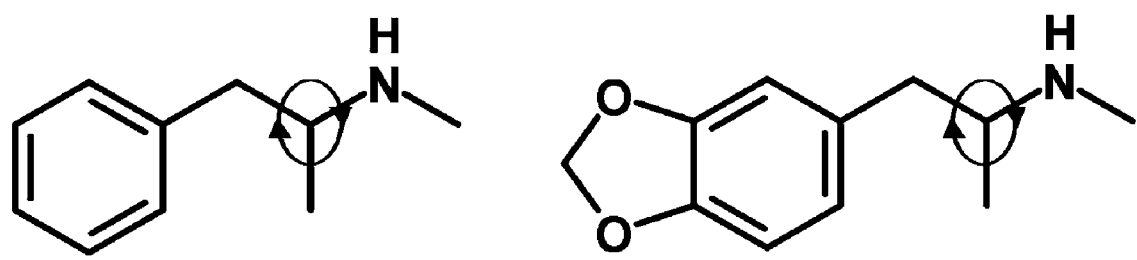
FIG. 1 shows the two-dimensional molecular structures of methamphetamine (left side structure) and 3,4-methylenedioxymethamphetamine (MDMA) (right side structure). Arrows indicate the chiral carbon in each structure, which gives rise to enantiomers.

Unless otherwise indicated, the definitions and embodiments described in this and other sections are intended to be applicable to all embodiments and aspects of the present application herein described for which they are suitable as would be understood by a person skilled in the art.

In understanding the scope of the present application, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives.

The term "composition of the application" as used herein refers to any composition comprising a non-racemic mixture of compounds of Formula (R)-I and (S)-I, and/or a salt and/or solvate thereof as described herein as well as any composition comprising (R)-I, and/or a salt and/or solvate thereof as described herein.

The term "consisting" and its derivatives, as used herein, are intended to be closed terms that specify the presence of the stated features, elements, components, groups, integers, and/or steps, but exclude the presence of other unstated features, elements, components, groups, integers and/or steps.

The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "substantially", "about" and "approximately" as used herein mean a reasonable amount of deviation of the modified term such that the end-result is not significantly changed. These terms of degree should be construed as including a deviation of at least ±5% of the modified term if this deviation would not negate the meaning of the word it modifies.

As used in this application, the singular forms "a", "an" and "the" include plural references unless the content clearly dictates otherwise.

In embodiments comprising an "additional" or "second" component, the second component as used herein is chemically different from the other components or first component. A "third" component is different from the other, first, and second components, and further enumerated or "additional" components are similarly different.

The term "and/or" as used herein means that the listed items are present, or used, individually or in combination. In effect, this term means that "at least one of" or "one or more" of the listed items is used or present.

The term "subject" as used herein includes all members of the animal kingdom including mammals, and suitably refers to humans. Thus, the methods of the present application are applicable to both human therapy and veterinary applications.

The term "MDMA" or as used herein refers to a compound having the IUPAC name: 1-(1,3-benzodioxol-5-yl)-N-methylpropan-2-amine, or the chemical name 3,4-Methylenedioxymethamphetamine, and having the chemical formula:

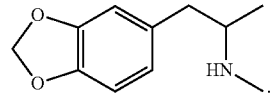

The term "(R)-MDMA" as used herein refers to a compound having the IUPAC name: (2R)-1-(1,3-benzodioxol-5-yl)-N-methylpropan-2-amine, or the chemical name (R)-3,4-Methylenedioxymethamphetamine, and having the chemical formula:

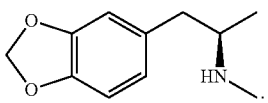

The term "(S)-MDMA" as used herein refers to a compound having the IUPAC name: (2S)-1-(1,3-benzodioxol-5-yl)-N-methylpropan-2-amine, or the chemical name (S)-3,4-Methylenedioxymethamphetamine, and having the chemical formula:

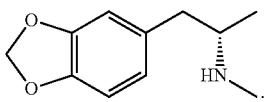

The term "MBDB" as used herein refers to a compound having the IUPAC name: 1-(1,3-benzodioxol-5-yl)-N-methylbutan-2-amine, or the chemical name N-methyl-1,3-benzodioxolylbutanamine, and having the chemical formula:

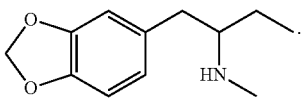

The term "(R)-MBDB" as used herein refers to a compound having the IUPAC name: (2R)-1-(1,3-benzodioxol-5-yl)-N-methylbutan-2-amine, or the chemical name (R)—N-methyl-1,3-benzodioxolylbutanamine, and having the chemical formula:

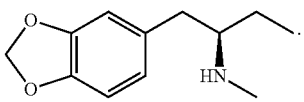

The term "(S)-MBDB" as used herein refers to a compound having the IUPAC name: (2S)-1-(1,3-benzodioxol-5-yl)-N-methylbutan-2-amine, or the chemical name (S)—N-methyl-1,3-benzodioxolylbutanamine, and having the chemical formula:

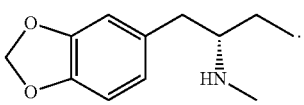

The term "pharmaceutical composition" as used herein refers to a composition of matter for pharmaceutical use.

The term "for pharmaceutical use" means compatible with the treatment of subjects.

The term "pharmaceutically acceptable" means compatible with the treatment of subjects.

The term "pharmaceutically acceptable salt" means an acid addition salt which is suitable for, or compatible with the treatment of subjects.

An acid addition salt suitable for, or compatible with, the treatment of subjects is any non-toxic organic or inorganic acid addition salt of any basic compound.

The term "solvate" as used herein means a compound, or a salt of a compound, wherein molecules of a suitable solvent are incorporated in the crystal lattice. A suitable solvent is physiologically tolerable at the dosage administered.

The term a "therapeutically effective amount" of compositions of the application or (R)-MDMA or a pharmaceutically acceptable salt and/or solvate thereof as used herein refers to a quantity sufficient to, when administered to a subject, effect beneficial or desired results, including clinical results, and, as such, a "therapeutically effective amount" or synonym thereto depends upon the context in which it is being applied. Therefore, as used herein "therapeutically effective amount" is intended to mean that amount of a compound or composition that is sufficient to treat, prevent or inhibit diseases or conditions. The amount of a given compound or composition of the present application that will correspond to such an amount will vary depending upon various factors, such as the given compound or composition, the pharmaceutical formulation, the route of administration, the type of disease or disorder, the identity of the subject being treated, and the like, but can nevertheless be routinely determined by one skilled in the art.

The term "administered" as used herein means administration of a therapeutically effective amount of a composition of the application or of (R)-MDMA, a pharmaceutically acceptable salt and/or solvate thereof, to a cell either in cell culture or in a subject.

The terms "to treat", "treating" and "treatment" as used herein and as is well understood in the art, means an approach for obtaining beneficial or desired results, including clinical results. Examples of beneficial or desired clinical results with respect to any disease, disorder or condition, include, but are not limited to diminishment of extent, stabilized (i.e., not worsening) state, preventing spread, delay or slowing of progression, amelioration or palliation of the state, and remission (whether partial or total), whether detectable or undetectable. "To treat", "treating" and "treatment" can also mean prolonging survival as compared to expected survival if not receiving treatment. "To treat", "treating" and "treatment" as used herein also includes prophylactic treatment.

"Palliating" a disease, disorder or condition means that the extent and/or undesirable clinical manifestations of a disease, disorder or condition are lessened and/or time course of the progression is slowed or lengthened, as compared to not treating the disease, disorder or condition.

The term "prevention" or "prophylaxis", or synonym thereto, as used herein refers to a reduction in the risk or probability of a patient becoming afflicted with a disease, disorder or condition or manifesting a symptom associated with a disease, disorder or condition.

The term "ON-time" as used herein means the duration of the antiparkinsonian effect of L-DOPA.

When used, for example, with respect to the methods of treatment, uses, compositions and/or kits of the application, a subject, for example a subject "in need thereof" is a subject who has been diagnosed and/or has been treated for a disease, disorder or condition that would benefit from administration of the compositions of the application or of (R)-MDMA or a pharmaceutically acceptable salt and/or solvate thereof.

The term "enantiomeric equivalents" as used herein refers to the molar amount of the base compound of each enantiomer of the compound of Formula I, i.e., (R)-I and (S)-I, irrespective of whether the enantiomer is present as a salt and/or solvate. Therefore, the percent of enantiomeric equivalents of each of (R)-I and (S)-I is defined by the molar quantity of either (R)-I or (S)-I divided by the total molar quantity of both (R)-I and (S)-I. The amounts of any anion forming salts and/or solvate-forming solvents are excluded and do not count in determining the percent of enantiomeric equivalents of each of (R)-I and (S)-I II. Non-Racemic Compositions of the application The present application includes a composition comprising a non-racemic mixture a compound of Formula (R)-I, or a salt and/or solvate thereof, and (S)-I, or a salt and/or solvate thereof:

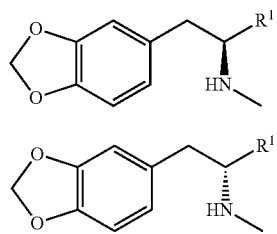

wherein $R^1$ is $CH_3$ or $CH_2CH_3$, and (R)-I, or a salt and/or solvate thereof, is present in the composition in a greater amount by enantiomeric equivalents, relative to (S)-I, or a salt and/or solvate thereof.

In some embodiments, the composition comprises about 70% to about 99% by enantiomeric equivalents of the compound of Formula (R)-I, or a salt and/or solvate thereof, and about 1% to about 30% by enantiomeric equivalents of the compound of Formula (S)-I, or a salt and/or solvate thereof.

In some embodiments, the composition comprises about 70% to about 79.9% by enantiomeric equivalents of the compound of Formula (R)-I, or a salt and/or solvate thereof, and about 20.1% to about 30% by enantiomeric equivalents of the compound of Formula (S)-I, or a salt and/or solvate thereof.

In some embodiments, the composition comprises about 70% to about 75% by enantiomeric equivalents of the compound of Formula (R)-I, or a salt and/or solvate thereof, and 25% to about 30% by enantiomeric equivalents of the compound of Formula (S)-I, or a salt and/or solvate thereof.

In some embodiments, the composition comprises about 75% to about 79.9% by enantiomeric equivalents of the compound of Formula (R)-I, or a salt and/or solvate thereof, and about 20.1% to about 25% by enantiomeric equivalents of the compound of Formula (S)-I, or a salt and/or solvate thereof.

In some embodiments, the composition comprises about 80% to about 89.9% by enantiomeric equivalents of the compound of Formula (R)-I, or a salt and/or solvate thereof, and about 10.1% to about 20% by enantiomeric equivalents of the compound of Formula (S)-I or a salt and/or solvate thereof.

In some embodiments, the composition comprises about 80% to about 85% by enantiomeric equivalents of the Formula (R)-I, or a salt and/or solvate thereof, and about 15% to about 20% by enantiomeric equivalents of the Formula (S)-I, or a salt and/or solvate thereof.

In some embodiments, the composition comprises about 80% by enantiomeric equivalents of the Formula (R)-I, or a salt and/or solvate thereof, and about 20% by enantiomeric equivalents of the Formula (S)-I, or a salt and/or solvate thereof.

In some embodiments, the composition comprises about 85% to about 89.9% by enantiomeric equivalents of the compound of Formula (R)-I, or a salt and/or solvate thereof, and about 10.1% to about 15% by enantiomeric equivalents of the compound of Formula (S)-I, or a salt and/or solvate thereof.

In some embodiments, the composition comprises about 90% to about 99% by enantiomeric equivalents of the compound of Formula (R)-I, or a salt and/or solvate thereof, and about 1% to about 10% by enantiomeric equivalents of the compound of Formula (S)-I, or a salt and/or solvate thereof.

In some embodiments, the composition comprises about 90% to about 95% by enantiomeric equivalents of the Formula (R)-I, or a salt and/or solvate thereof, and about 5% to about 10% by enantiomeric equivalents the compound of Formula (S)-I, or a salt and/or solvate thereof.

In some embodiments, the composition comprises about 95% to about 99% by enantiomeric equivalents of the Formula (R)-I, or a salt and/or solvate thereof, and about 1% to about 5% by enantiomeric equivalents of the compound of Formula (S)-I, or a salt and/or solvate thereof.

In some embodiments, $R^1$ is $CH_3$ and the compound of Formula (R)-I is (R)-3,4-methylenedioxymethamphetamine ((R)-MDMA), and the compound of Formula (S)-I is (S)-3,4-Methylenedioxymethamphetamine ((S)-MDMA).

In some embodiments, $R^1$ is $CH_2CH_3$ and the compound of Formula (R)-I is (R)—N-methyl-1,3-benzodioxolylbutanamine ((R)-MBDB) and the compound of Formula (S)-I is (S)—N-methyl-1,3-benzodioxolylbutanamine ((S)-MBDB).

(R)-MDMA and (S)-MDMA (compounds of Formula (R)-I and (S)-I, wherein $R^1$ is $CH_3$) can be prepared by various synthetic processes. The selection of a particular process is within the purview of the person of skill in the art. For example, (R)-MDMA and (S)-MDMA can be prepared, for example, by the methods disclosed in Dunlap et al (2018), ACS Chem Neurosci; 9(10): 2408-2427; Llabrés et al (2014), European J. of Med. Chem. 81 (2014) 35-46; Huot et al (2011), J Neurosci. (2011) May 11; 31(19): 7190-7198 and Felim et al., Chem Res Toxicol. 2010 23(1):211-9.

(R)-MBDB and (S)-MBDB (compounds of Formula (R)-I and (S)-I, wherein $R^1$ is $CH_2CH_3$) can be prepared by various synthetic processes. The selection of a particular process is within the purview of the person of skill in the art. For example, (R)-MBDB and (S)-MBDB can be prepared for example, by the methods for preparing (R)-MDMA and (S)-MDMA described above or the methods disclosed in Applicant's co-pending U.S. provisional application No. 63/201,609, U.S. provisional application No. 63/203,099, U.S. provisional application No. 63/201,610, and U.S. provisional application No. 63/203,101.

Alternatively, the compounds of Formula (R)-I and (S)-I are available using enantiomer separation methods known in the art, for example using chromatographic, crystallization or other such methods to isolate the individual enantiomers from the racemic mixture.

In some embodiments the compounds of Formula (R)-I and/or (S)-I are provided as salts. The selection of a suitable salt may be made by a person skilled in the art. Acids that are generally considered suitable for the formation of pharmaceutically acceptable salts from basic pharmaceutical compounds are discussed, for example, by P. Stahl et al, Camille G. (eds.) and Handbook of Pharmaceutical Salts.

Properties, Selection and Use. (2002) Zurich: Wiley VCH; S. Berge et al, Journal of Pharmaceutical Sciences 1977 66(1) 1-19; P. Gould, International J. of Pharmaceutics (1986) 33 201-217; Anderson et al, The Practice of Medicinal Chemistry (1996), Academic Press, New York; and in The Orange Book (Food & Drug Administration, Washington, D.C. on their website).

In some embodiments, the acid addition salt suitable for, or compatible with, the treatment of subjects is any non-toxic organic or inorganic acid addition salt. Illustrative inorganic acids which form suitable salts include hydrochloric, hydrobromic, sulfuric, nitric and phosphoric acids, as well as acidic metal salts such as sodium monohydrogen orthophosphate and potassium hydrogen sulfate. Illustrative organic acids which form suitable salts include mono-, di- and tricarboxylic acids. Illustrative of such organic acids are, for example, acetic, trifluoroacetic, propionic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, mandelic, salicylic, 2-phenoxybenzoic, p-toluenesulfonic acid and other sulfonic acids such as methanesulfonic acid, ethanesulfonic acid and 2-hydroxyethanesulfonic acid. In some embodiments, exemplary acid addition salts also include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates ("mesylates"), naphthalenesulfonates, nitrates, oxalates, phosphates, propionates, salicylates, succinates, sulfates, tartarates, thiocyanates, toluenesulfonates (also known as tosylates) and the like. In some embodiments, the salts exist in either a hydrated, solvated or substantially anhydrous form. In general, acid addition salts are more soluble in water and various hydrophilic organic solvents and generally demonstrate higher melting points in comparison to their free base forms.

Salts of compounds of compound of Formula (R)-I or (S)-I may be formed by methods known to those of ordinary skill in the art, for example, by reacting (R)-I or (S)-I with an amount of acid, such as an equivalent amount, in a medium such as one in which the salt precipitates or in aqueous medium followed by lyophilization.

In some embodiments the compounds of Formula (R)-I and/or (S)-I are provided solvates. The solvates include, for example, those made with solvents that are pharmaceutically acceptable. Examples of such solvents include water (resulting solvate is called a hydrate) and ethanol and the like. Suitable solvents are physiologically tolerable at the dosage administered.

In general, solvates are formed by dissolving the compound in the appropriate solvent and isolating the solvate by cooling or using an antisolvent. The solvate is typically dried or azeotroped under ambient conditions. The selection of suitable conditions to form a particular solvate can be made by a person skilled in the art.

The compounds of Formula (R)-I and (S)-I, or a pharmaceutically acceptable salt and/or solvate thereof, may further exist in varying polymorphic forms and it is contemplated that any polymorphs, or mixtures thereof, which form are included within the scope of the present application.

In some embodiments, the compounds of Formula (R)-I and (S)-I are both in free base form. In some embodiments, the compounds of Formula (R)-I and (S)-I are both in acid salt form.

The compounds of Formula (R)-I and (S)-I, and/or salts and/or solvates thereof are suitably formulated into pharmaceutical compositions for administration to subjects in a biologically compatible form suitable for administration in vivo. Accordingly, in an embodiment, the compositions of the application are pharmaceutical compositions and further comprise one or more pharmaceutically acceptable carriers.

The pharmaceutical compositions of the application are administered to a subject in a variety of forms depending on the selected route of administration, as will be understood by those skilled in the art. For example, the compositions of the application are administered by oral, inhalation, parenteral, buccal, sublingual, nasal, rectal, vaginal, patch, pump, minipump, topical or transdermal administration and the pharmaceutical compositions formulated accordingly. In some embodiments, administration is by means of a pump for periodic or continuous delivery. Conventional procedures and ingredients for the selection and preparation of suitable compositions are described, for example, in Remington's Pharmaceutical Sciences (2000-20th edition) and in The United States Pharmacopeia: The National Formulary (USP 24 NF19) published in 1999.

Parenteral administration includes systemic delivery routes other than the gastrointestinal (GI) tract, and includes, for example intravenous, intra-arterial, intraperitoneal, subcutaneous, intramuscular, transepithelial, nasal, intrapulmonary (for example, by use of an aerosol), intrathecal, rectal and topical (including the use of a patch or other transdermal delivery device) modes of administration. Parenteral administration may be by continuous infusion over a selected period of time.

In some embodiments, a composition of the application is orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the composition may be incorporated with excipient and used in the form of ingestible tablets, buccal tablets, troches, capsules, caplets, pellets, granules, lozenges, chewing gum, powders, syrups, elixirs, wafers, aqueous solutions or suspensions, and the like. In the case of tablets, carriers that are used include lactose, corn starch, sodium citrate and salts of phosphoric acid. Pharmaceutically acceptable excipients include binding agents (e.g., pregelatinized maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). The tablets are coated by methods well known in the art. In the case of tablets, capsules, caplets, pellets or granules for oral administration, pH sensitive enteric coatings, such as Eudragits™ designed to control the release of active ingredients are optionally used. Oral dosage forms also include modified release, for example immediate release and timed-release, formulations. Examples of modified-release formulations include, for example, sustained-release (SR), extended-release (ER, XR, or XL), time-release or timed-release, controlled-release (CR), or continuous-release (CR or Contin), employed, for example, in the form of a coated tablet, an osmotic delivery device, a coated capsule, a microencapsulated microsphere, an agglomerated particle, e.g., as of molecular sieving type particles, or, a fine hollow permeable fiber bundle, or chopped hollow permeable fibers, agglomerated or held in a fibrous packet. Timed-release compositions can be formulated, e.g., in liposomes or those wherein the compositions are protected with differentially degradable coatings, such as by microencapsulation, multiple coatings, etc. Liposome delivery systems include, for example, small unilamellar vesicles, large unilamellar vesicles and multilamellar vesicles. Liposomes can be formed from a variety of phospholipids, such as cholesterol, stearylamine or phosphatidylcholines. For oral administration in a capsule form, useful carriers or diluents include lactose and dried corn starch.

In some embodiments, liquid preparations for oral administration take the form of, for example, solutions, syrups or suspensions, or they are suitably presented as a dry product for re-constitution with water or other suitable vehicle(s) before use. When aqueous suspensions and/or emulsions are administered orally, the compositions of the application are suitably suspended or dissolved in an oily phase that is combined with emulsifying and/or suspending agents. If desired, certain sweetening and/or flavoring and/or coloring agents are added. In some embodiments, such liquid preparations for oral administration are prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid). Useful diluents include lactose and high molecular weight polyethylene glycols.

In some embodiments, the compositions of the application are formulated as solid or semi-solid compositions. In some embodiments, the compositions of the application are formulated as tablets, buccal tablets, troches, capsules, caplets, pellets, granules, lozenges, chewing gum, powders, syrups, elixirs, wafers, aqueous solutions or suspensions. In some embodiments, the compositions of the application are formulated as tablets or capsules. In some embodiments, the compositions of the application are formulated as tablets.

It is also possible to freeze-dry the compositions of the application and use the lyophilizates obtained, for example, for the preparation of products for injection.

In some embodiments, the compositions of the application are administered parenterally. For example, solutions of the compositions of the application are prepared in water suitably mixed with a surfactant such as hydroxypropylcellulose. In some embodiments, dispersions are prepared in glycerol, liquid polyethylene glycols, DMSO and mixtures thereof with or without alcohol, and in oils. Under ordinary conditions of storage and use, these preparations contain a preservative to prevent the growth of microorganisms. A person skilled in the art would know how to prepare suitable formulations. For parenteral administration, sterile solutions of the compositions of the application are usually prepared, and the pH's of the solutions are suitably adjusted and buffered. For intravenous use, the total concentration of solutes should be controlled to render the preparation isotonic. For ocular administration, ointments or droppable liquids are delivered, for example, by ocular delivery systems known to the art such as applicators or eye droppers. In some embodiments, such formulations include mucomimetics such as hyaluronic acid, chondroitin sulfate, hydroxypropyl methylcellulose or polyvinyl alcohol, preservatives such as sorbic acid, EDTA or benzyl chromium chloride, and the usual quantities of diluents or carriers. For pulmonary administration, diluents or carriers will be selected to be appropriate to allow the formation of an aerosol.

In some embodiments, the compositions of the application are formulated for parenteral administration by injection, including using conventional catheterization techniques or infusion. Compositions for injection are, for example, presented in unit dosage form, e.g., in ampoules or in multi-dose containers, with an added preservative. In some embodiments, the compositions are formulated as sterile suspensions, solutions or emulsions in oily or aqueous vehicles, and contain formulating agents such as suspending, stabilizing and/or dispersing agents. In all cases, the form must be sterile and must be fluid to the extent that easy syringability exists. Alternatively, the compositions of the application are suitably in a sterile powder form for reconstitution with a suitable vehicle, e.g., sterile pyrogen-free water, before use.

MDMA (±) 3,4-methylenedioxymethamphetamine, 'ecstasy') is used recreationally, reportedly because it increases feelings of empathy, sociability, and interpersonal closeness. Through clinical research and some animal studies, it is known that MDMA metabolism is rather complex. It includes 2 main hepatic metabolic pathways: (1) O-demethylation to generate, for example, (±)-4-hydroxy-3-methoxymethamphetamine (HMMA), and/or glucuronide/sulfate conjugation; and (2) N-dealkylation, deamination, and oxidation to the corresponding benzoic acid derivatives conjugated with glycine to generate, for example, form (±)-3,4-methylenedioxyamphetmaine (MDA) and 3,4-dihydroxymethamphetamine (DHMA), (±)-3,4-dihydroxyamphetamine (HHA) (Baumann M H et al., Drug Metab Dispos. 2009; 37(11):2163-70).

A marked difference in the Cmax of MDMA in rats based on the route of delivery has been observed (Baumann M H et al., Drug Metab Dispos. 2009; 37(11):2163-70). At 2 mg/kg, maximum MDMA concentrations were ~200 ng/ml for intraperitoneal (210 ng/ml) and subcutaneous routes (196 ng/ml), but less for the oral route (46 ng/ml). At higher doses, (10 mg/kg), Cmax via intraperitoneal (2257 ng/ml) and subcutaneous (1130 ng/ml) route of administration was higher than via oral route (966 ng/ml).

It is also known that the (R)- and (S)-enantiomers of racemic 3,4-methylenedioxymethamphetamine (MDMA) exhibit different dose-concentration curves. MDMA, MDA, DHMA, DHMA sulfates, HMMA, HMMA sulphates, and HMMA glucuronides have been shown to be excreted in human urine in substantial amounts (Schwaninger A E, et al. Biochem Pharmacol. 2012; 83(1):131-8). Statistically significant differences between the two enantiomers (R- and S- of individual metabolites) were observed for all compounds, except HMMA sulfate after creatinine normalization. Higher R-enantiomer Cmax was observed for MDMA, DHMA and HMMA sulfate, whereas S-enantiomers were higher for DHMA sulphate, HMMA, HMMA glucuronide, and MDA.

The oral mucosa is occasionally used as the site of drug absorption. Sublingual administration, in which a tablet or troche is allowed to dissolve completely in the oral cavity, takes advantage of the permeability of the oral epithelium and is the route of administration for a few potent lipophilic drugs, such as nitroglycerin and oxytocin, and even the oral sedative triazolam.

MDMA has demonstrated efficacy in phase 3 trials to treat Post Traumatic Stress Disorder (PTSD) via MDMA-assisted psychotherapy. It is known to have complex pharmacology and impact multiple receptors in the brain.

In some embodiments, intranasal administration is believed to offer both direct and indirect pathways to the delivery of psychopharmacological agents to the central nervous system (CNS). Direct nose-to-brain transport via olfactory and trigeminal nerve pathways after intranasal deposition and absorption on the olfactory and respiratory epithelia provides a non-invasive means of circumventing the blood-brain barrier (BBB), which is an obstacle for drug delivery to CNS. In some embodiments in comparison to other routes of administration (e.g. oral administration), intranasal offers ease of use, reduced systemic exposure, faster drug onset, increased compliance, and greater bioavailability by avoiding first-pass metabolism (Keller et al. Drug Deliv. and Transl. Res. 12, 735-757 (2022))

Therefore, in some embodiments, sublingual and intranasal administration avoids drug destruction. In some embodiments, sublingual and intranasal administration avoids drug destruction by bypassing gastric acid and intestinal and hepatic enzymes.

In some embodiments, sublingual and intranasal absorption is more efficient compared to intestinal uptake, for example, when using oral administration. In some embodiments, the onset of drug effects using sublingual or intranasal administration is faster compared to the onset of the same drug effects using oral administration.

In some embodiments, a better drug absorption and metabolic profile is achieved when using sublingual or intranasal administration compared to oral administration. In some embodiments, hepatic metabolism is more subdued using sublingual or intranasal administration compared to oral administration. In some embodiments, a lower dose of an active ingredient, e.g., MDMA, is used to achieve a biological effect by sublingual or intranasal administration compared to the dose of an active ingredient to achieve the same biological effect by oral administration. In some embodiments, sublingual or intranasal administration affords better bioavailability and a better safety profile for an active ingredient, e.g., MDMA compared with oral administration.

Accordingly, in some embodiments, the compositions comprising a non-racemic mixture a compound of Formula (R)-I, or a salt and/or solvate thereof, and (S)-I, or a salt and/or solvate thereof described above are formulated for intranasal administration or use.

Therefore, in some embodiments, the present application also includes an intranasal composition comprising a non-racemic mixture a compound of Formula (R)-I, or a salt and/or solvate thereof, and (S)-I, or a salt and/or solvate thereof:

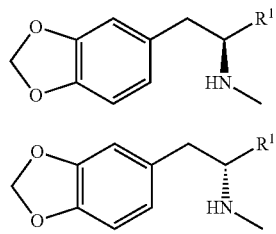

R-I

S-I wherein $R^1$ is $CH_3$ or $CH_2CH_3$, and (R)-I, or a salt and/or solvate thereof, is present in the composition in a greater amount by enantiomeric equivalents, relative to (S)-I, or a salt and/or solvate thereof.

In some embodiments, the amounts or enantiomeric equivalents of the compound of Formula (R)-I, or a salt and/or solvate thereof, and (S)-I, or a salt and/or solvate thereof in the non-racemic mixture in the intranasal compositions are as described above.

In some embodiments, the compositions comprising a non-racemic mixture of a compound of Formula (R)-I, or a salt and/or solvate thereof, and (S)-I, or a salt and/or solvate thereof are for use or administration in the treatment of any of the diseases, disorders or conditions described herein.

In some embodiments, compositions for nasal administration are conveniently formulated as aerosols, drops, gels and powders. For intranasal administration or administration by inhalation, the compositions of the application are conveniently delivered in the form of a solution, dry powder formulation or suspension from a pump spray container that is squeezed or pumped by the subject or as an aerosol spray presentation from a pressurized container or a nebulizer. Aerosol compositions typically comprise a solution or fine suspension of the compositions of the application in a physiologically acceptable aqueous or non-aqueous solvent and are usually presented in single or multidose quantities in sterile form in a sealed container, which, for example, take the form of a cartridge or refill for use with an atomising device. Alternatively, the sealed container is a unitary dispensing device such as a single dose nasal inhaler or an aerosol dispenser fitted with a metering valve which is intended for disposal after use. Where the dosage form comprises an aerosol dispenser, it will contain a propellant which is, for example, a compressed gas such as compressed air or an organic propellant such as fluorochlorohydrocarbon. Suitable propellants include but are not limited to dichlorodifluoromethane, trichlorofluoromethane, dichlorotetrafluoroethane, heptafluoroalkanes, carbon dioxide or another suitable gas. In the case of a pressurized aerosol, the dosage unit is suitably determined by providing a valve to deliver a metered amount. In some embodiments, the pressurized container or nebulizer contains a solution or suspension of the compositions of the application. Capsules and cartridges (made, for example, from gelatin) for use in an inhaler or insufflator are, for example, formulated containing a powder mix of a composition of the application and a suitable powder base such as lactose or starch. The aerosol dosage forms can also take the form of a pump-atomizer.

In some embodiments, the intranasal pharmaceutical composition comprising a non-racemic mixture a compound of Formula (R)-I, or a salt and/or solvate thereof, and (S)-I, or a salt and/or solvate thereof is formulated as an aerosol for use with a pump-atomizer.

In some embodiments, the intranasal pharmaceutical composition comprising a non-racemic mixture a compound of Formula (R)-I, or a salt and/or solvate thereof, and (S)-I, or a salt and/or solvate thereof described above is a powder. In some embodiments, the powder is a dry powder. In some embodiment, the dry powder is formulated to be reconstituted with a suitable vehicle before use or administration. In some embodiments the suitable vehicle is sterile pyrogen-free water.

In some embodiments, the powder is formulated for use or administration with an inhaler or insufflator. Accordingly, in some embodiments, the dry powder is formulated for use or administration as a capsule and cartridge for use with an inhaler or insufflator.

In some embodiments, the dry powder further comprises a suitable powder base. In some embodiment, the suitable powder based comprise lactose or starch.

In some embodiments, the intranasal pharmaceutical composition comprising a non-racemic mixture a compound of Formula (R)-I, or a salt and/or solvate thereof, and (S)-I, or a salt and/or solvate thereof described above further comprises water. Therefore, in some embodiments, the intranasal pharmaceutical composition comprising a non-racemic mixture a compound of Formula (R)-I, or a salt and/or solvate thereof, and (S)-I, or a salt and/or solvate thereof described above further comprises water and is an aqueous intranasal pharmaceutical composition.

In some embodiments, the intranasal pharmaceutical composition comprising a non-racemic mixture a compound of Formula (R)-I, or a salt and/or solvate thereof, and (S)-I, or a salt and/or solvate thereof described above is a solution, suspension or emulsion. In some embodiments, the intranasal pharmaceutical composition comprising a non-racemic mixture a compound of Formula (R)-I, or a salt and/or solvate thereof, and (S)-I, or a salt and/or solvate thereof described above is a solution.

In some embodiments, the aqueous intranasal pharmaceutical composition comprising a non-racemic mixture a compound of Formula (R)-I, or a salt and/or solvate thereof, and (S)-I, or a salt and/or solvate thereof described above is formulated for administration into the nose in the form of drops. In some embodiments, the aqueous intranasal pharmaceutical composition comprising a non-racemic mixture a compound of Formula (R)-I, or a salt and/or solvate thereof, and (S)-I, or a salt and/or solvate thereof described above is formulated for administration as a nasal spray. In some embodiments, the nasal spray is delivered in the form of a solution or suspension from a pump spray container that is squeezed or pumped by the patient or as an aerosol spray presentation from a pressurized container or a nebulizer. In some embodiments, the aqueous intranasal pharmaceutical composition comprising a non-racemic mixture a compound of Formula (R)-I, or a salt and/or solvate thereof, and (S)-I, or a salt and/or solvate thereof described above is formulated as an aerosol for use with a pump-atomizer.

In some embodiments, the water is present in the intranasal pharmaceutical composition in an amount of about 50% to about 75%, about 50% to about 70%, about 50% to about 65%, about 33% to about 75%, about 55% to about 70% or about 55% to about 65% by weight of the composition. In some embodiments, the water is present in an amount of about 50%, about 60%, about 65% or about 70% by weight of the composition. In some embodiments, the water is present in an amount of about 55% to about 65% by weight of the composition. In some embodiments, the water is about 60% by weight of the composition.

Compositions suitable for buccal or sublingual administration include tablets, lozenges, and pastilles, wherein the compositions of the application are formulated with a carrier such as sugar, acacia, tragacanth, or gelatin and glycerine. Compositions for rectal administration are conveniently in the form of suppositories containing a conventional suppository base such as cocoa butter.

In some embodiments, the compositions of the application are formulated for sublingual administration or use.

Therefore, in some embodiments, the present application also includes a sublingual composition comprising a non-racemic mixture a compound of Formula (R)-I, or a salt and/or solvate thereof, and (S)-I, or a salt and/or solvate thereof:

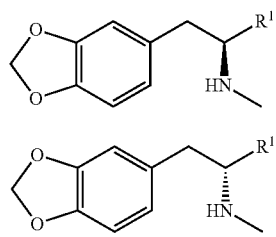

wherein $R^1$ is $CH_3$ or $CH_2CH_3$, and (R)-I, or a salt and/or solvate thereof, is present in the composition in a greater amount by enantiomeric equivalents, relative to (S)-I, or a salt and/or solvate thereof.

In some embodiments, the amounts or enantiomeric equivalents of the compounds in the non-racemic mixtures in the sublingual compositions of the application are as described above.

In some embodiments, the sublingual compositions comprising a non-racemic mixture are used in the treatment of any of the diseases, disorders or conditions described herein.

In some embodiments, the sublingual composition are formulated as tablets, drops, strips, sprays, lozenges or effervescent tablets.

Suppository forms of the compositions of the application are useful for vaginal, urethral and rectal administrations. Such suppositories will generally be constructed of a mixture of substances that is solid at room temperature but melts at body temperature. The substances commonly used to create such vehicles include but are not limited to theobroma oil (also known as cocoa butter), glycerinated gelatin, other glycerides, hydrogenated vegetable oils, mixtures of polyethylene glycols of various molecular weights and fatty acid esters of polyethylene glycol. See, for example: Remington's Pharmaceutical Sciences, 16th Ed., Mack Publishing, Easton, PA, 1980, pp. 1530-1533 for further discussion of suppository dosage forms.

In some embodiments, the compositions of the application comprise about 40 mg to about 180 mg of both the compounds of Formulae (R)-I and (S)-I, and/or a salt and/or solvate thereof. In some embodiments, the compositions of the application comprise 40 mg, 60 mg, 75 mg, 80 mg, 100 mg, 120 mg or 125 mg of both the compounds of Formulae (R)-I and (S)-I, and/or a salt and/or solvate thereof. In some embodiments, depending on the mode of administration, the compositions of the application are pharmaceutical compositions that comprise about 0.05 wt % to about 99 wt % or about 0.10 wt % to about 70 wt %, of both the compounds of Formulae (R)-I and (S)-I, and/or a salt and/or solvate thereof, and from about 1 wt % to about 99.95 wt % or about 30 wt % to about 99.90 wt % of one or more pharmaceutically acceptable carriers, all percentages by weight being based on the total composition.

In some embodiments, the compounds of Formulae (R)-I and (S)-I, and/or a salt and/or solvate thereof, are present in the compositions in an effective amount, for example an effective amount to treat or prevent a disease, disorder or condition that benefits from treatment with a racemic mixture of a compound of Formula I, and/or pharmaceutically acceptable salts and/or solvates thereof, or that benefits from psychotherapy in combination with a racemic mixture of a compound of Formula I, and/or pharmaceutically acceptable salts and/or solvates thereof. In some embodiments the effective amounts are determined as described in the Methods and Uses section below.

In some embodiments the compositions of the application are pharmaceutical compositions comprising an additional therapeutic agent, and optionally one or more pharmaceutically acceptable carriers. In some embodiments, the additional therapeutic agent is known agent useful for treating a disease, disorder or condition that benefits from treatment with a racemic mixture of a compound of Formula I, and/or pharmaceutically acceptable salts and/or solvates thereof, or that benefits from treatment with psychotherapy in combination with a racemic mixture of a compound of Formula I, and/or pharmaceutically acceptable salts and/or solvates thereof.

III. Methods and Uses of the Application (i) Methods and Uses of Compositions of the Application In some embodiments, the compositions of the application, including pharmaceutical compositions, can be used in a method of reducing adverse side effects of treatment with a racemic mixture of a compound of Formula I, or pharmaceutically acceptable a salt and/or solvate thereof:

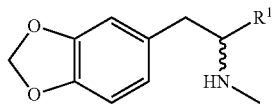
(I)

wherein
$R^1$ is selected from $CH_3$ and $CH_2CH_3$,
the method comprises administering a therapeutically effective amount of one or more compositions comprising a non-racemic mixture a compound of Formula (R)-I, or a salt and/or solvate thereof, and (S)-I, or a salt and/or solvate thereof described above to a subject in need thereof.

The present application further includes a use of one or more compositions comprising a non-racemic mixture a compound of Formula (R)-I, or a salt and/or solvate thereof, and (S)-I, or a salt and/or solvate thereof described above for reducing adverse side effects of treatment with a racemic mixture of Formula I, or a pharmaceutically acceptable salt and/or solvate thereof; a use of one or more compositions comprising a non-racemic mixture a compound of Formula (R)-I, or a salt and/or solvate thereof, and (S)-I, or a salt and/or solvate thereof described above for preparing a medicament for reducing adverse side effects of treatment with a racemic mixture of Formula I, or a pharmaceutically acceptable salt and/or solvate thereof, as well as one or more compositions comprising a non-racemic mixture a compound of Formula (R)-I, or a salt and/or solvate thereof, and (S)-I, or a salt and/or solvate thereof described above for use to reduce adverse side effects of treatment with a racemic mixture of Formula I, or a pharmaceutically acceptable salt and/or solvate.

In some embodiments, the adverse side effects are selected from one or more of neurotoxicity, hyperthermia, and substance use disorder. In some embodiments, the substance use disorder is drug abuse or drug dependence. In some embodiments, the substance use disorder is drug abuse of the compounds of Formula I.

In some embodiments, the adverse side effect is selected from one or more of hyperthermia and neurotoxicity.

Reports have suggested that long term use of MDMA could lead to heart valve fibroplasia and disfunction, such as valvular heart disease (VHD) (Setola et al. Mol. Pharmacol. 63:1223-1229, 2003). Therefore, in some embodiments, the adverse side effects is cardiotoxicity. In some embodiments, the cardiotoxicity is heart valve fibroplasia and disfunction. In some embodiments, the cardiotoxicity is valvular heart disease. Therefore, in some embodiments, the adverse side effect is valvular heart disease.

The present application also includes a method for treating diseases, disorders or conditions that benefit from treatment with a racemic mixture of a compound of Formula I or a pharmaceutically acceptable salt and/or solvate thereof:

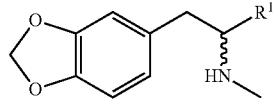
(I)

wherein
$R^1$ is selected from $CH_3$ and $CH_2CH_3$,
the method comprising administering a therapeutically effective amount of one or more compositions comprising a non-racemic mixture a compound of Formula (R)-I, or a salt and/or solvate thereof, and (S)-I, or a salt and/or solvate thereof described above to a subject in need thereof.

The present application further includes a use of one or more compositions comprising a non-racemic mixture a compound of Formula (R)-I, or a salt and/or solvate thereof, and (S)-I, or a salt and/or solvate thereof described above for treating diseases, disorders or conditions that benefit from treatment with a racemic mixture of a compound of Formula I, or a pharmaceutically acceptable salt and/or solvate thereof, a use of one or more compositions comprising a non-racemic mixture a compound of Formula (R)-I, or a salt and/or solvate thereof, and (S)-I, or a salt and/or solvate thereof described above for preparation of a medicament for treating diseases, disorders or conditions that benefit from treatment with a racemic mixture of a compound of Formula I, or a pharmaceutically acceptable salt and/or solvate thereof, as well as one or more compositions comprising a non-racemic mixture a compound of Formula (R)-I, or a salt and/or solvate thereof, and (S)-I, or a salt and/or solvate thereof described above for use to treat diseases, disorders or conditions that benefit from treatment with a racemic mixture of a compound of Formula I, or a pharmaceutically acceptable salt and/or solvate thereof.

In some embodiments, $R^1$ is $CH_3$ and the compound of Formula I in the methods and uses defined above is racemic 3,4-methylenedioxymethamphetamine (MDMA).

In some embodiments, $R^1$ is $CH_2CH_3$ and the compound of Formula I in the methods and used defined above is racemic N-methyl-1,3-benzodioxolylbutanamine (MBDB).

The Applicant has shown that S(+)-MDMA and racemic compositions of MDMA in BTBR mice elicit a dose dependent increase in temperature. However, exemplary compositions comprising a non-racemic mixture of a compound of Formula (R)-I, or a salt and/or solvate thereof, and (S)-I, or a salt and/or solvate thereof and compositions of pure R(−)-MDMA did not elicit significant effects on core temperature. It is known that hyperthermia results in cellular damage and neurotoxicity (Walter and Carraretto, Crit Care. 2016 Jul. 14; 20(1):199).

Accordingly, in some embodiments, the administrating or use of the one or more compositions comprising a non-racemic mixture a compound of Formula (R)-I, or a salt and/or solvate thereof, and (S)-I, or a salt and/or solvate thereof described above has reduced adverse side effects compared to treatment with a racemic mixture of a compound of Formula I, or pharmaceutically acceptable a salt and/or solvate thereof.

Therefore, in some embodiments, the application includes a method for treating diseases, disorders or conditions that benefit from treatment with a racemic mixture of a compound of Formula I or a pharmaceutically acceptable salt and/or solvate thereof:

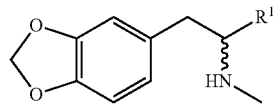

wherein
R¹ is selected from CH$_3$ and CH$_2$CH$_3$,
the method comprising administering a therapeutically effective amount of one or more compositions comprising a non-racemic mixture a compound of Formula (R)-I, or a salt and/or solvate thereof, and (S)-I, or a salt and/or solvate thereof described above to a subject in need thereof, and
the method further comprising having reduced adverse side effects compared to treatment with a racemic mixture of a compound of Formula I, or pharmaceutically a salt and/or solvate thereof.

The present application further includes a use of one or more compositions comprising a non-racemic mixture a compound of Formula (R)-I, or a salt and/or solvate thereof, and (S)-I, or a salt and/or solvate thereof described above for treating diseases, disorders or conditions that benefit from treatment with a racemic mixture of a compound of Formula I, or a pharmaceutically acceptable salt and/or solvate thereof and having reduced adverse side effects compared to treatment with a racemic mixture of a compound of Formula I, or pharmaceutically acceptable a salt and/or solvate thereof, a use of one or more compositions comprising a non-racemic mixture a compound of Formula (R)-I, or a salt and/or solvate thereof, and (S)-I, or a salt and/or solvate thereof described above for preparation of a medicament for treating diseases, disorders or conditions that benefit from treatment with a racemic mixture of a compound of Formula I, or a pharmaceutically acceptable salt and/or solvate thereof and having reduced adverse side effects compared to treatment with a racemic mixture of a compound of Formula I, or pharmaceutically acceptable a salt and/or solvate thereof, as well as one or more compositions comprising a non-racemic mixture a compound of Formula (R)-I, or a salt and/or solvate thereof, and (S)-I, or a salt and/or solvate thereof described above for use to treat diseases, disorders or conditions that benefit from treatment with a racemic mixture of a compound of Formula I, or a pharmaceutically acceptable salt and/or solvate thereof and having reduced adverse side effects compared to treatment with a racemic mixture of a compound of Formula I, or pharmaceutically acceptable a salt and/or solvate thereof.

In some embodiments, the adverse side effects are selected from one or more of neurotoxicity, hyperthermia, and substance use disorder. In some embodiments, the substance use disorder is drug abuse or drug dependence. In some embodiments, the substance use disorder is drug abuse of the compounds of Formula I.

In some embodiments, the adverse side effects are selected from one or more of hyperthermia and neurotoxicity. In some embodiments, the adverse side effect is hyperthermia.

In some embodiments, the diseases, disorders or conditions that benefit from treatment with a racemic mixture of a compound of Formula I or a pharmaceutically acceptable salt and/or solvate thereof, are any disease, disorder or condition that benefits from psychotherapy, including but not limited to one or more of post-traumatic stress disorder (PTSD), social anxiety disorder, depression, alcohol addiction, and eating disorders.

In some embodiments, the one or more compositions comprising a non-racemic mixture a compound of Formula (R)-I, or a salt and/or solvate thereof, and (S)-I, or a salt and/or solvate thereof described above are administered or used in combination with psychotherapy to treat the diseases, disorders or conditions. In some embodiments, the one or more compositions improve the efficacy of psychotherapy. In some embodiment, the psychotherapy is for psychiatric disorders.

In some embodiments, the diseases, disorders or conditions that benefit from treatment with a racemic mixture of a compound of Formula I, or a pharmaceutically acceptable salt and/or solvate thereof, are one or more psychiatric disorders. In some embodiments, the one or more psychiatric disorders are selected from one or more of anxiety disorders, mood disorders, developmental disorders, substance use disorders and addictions, eating disorders, personality disorders and psychotic disorders. In some embodiments, the substance use disorder is drug abuse or drug dependence.

In some embodiments, the anxiety disorder is selected from one or more of obsessive-compulsive disorder (OCD), social anxiety disorder, phobias, panic disorder and post-traumatic stress disorder (PTSD). In some embodiments, the anxiety disorder is social anxiety disorder. In some embodiments, the anxiety disorder is PTSD.

In some embodiments, the mood disorder is selected from one or both of depression and bipolar disorder.

In some embodiments, the developmental disorder is selected from an autism spectrum disorder (ASD). In some embodiments, the developmental disorder is Asperger syndrome.

In some embodiments, the substance use disorders and addictions are selected from one or more of alcoholism, drug abuse, drug dependence and compulsive gambling. In some embodiments, the drug dependence is opioid dependence. In some embodiments, the substance use disorder is opioid use disorder.

In some embodiments, the eating disorder is selected from anorexia and bulimia.

In some embodiments, the personality disorder is selected from borderline personality disorder and dependent personality disorder In some embodiments, the psychotic disorders are selected from schizophrenia and other disorders that cause detachment from reality.

In some embodiments, the one or more psychiatric disorders are selected from one or more of an autism spectrum disorder (ASD), depression and drug dependence. In some embodiments, the depression is clinical depression, for example, in palliative care subjects.

In some embodiments, the one or more psychiatric disorders are selected from post-traumatic stress disorder (PTSD), eating disorder and alcoholism. In some embodiments, the one or more psychiatric disorders is post-traumatic stress disorder (PTSD).

In some embodiments, the one or more psychiatric disorders are selected from an autism spectrum disorder (ASD), depression, and substance use disorder. In some embodiments, the depression is clinical depression, for example, in palliative care subjects. In some embodiments, the substance use disorder is opioid use disorder.

In some embodiments, the diseases, disorders or conditions that benefit from treatment with a racemic mixture of a compound of Formula I or a pharmaceutically acceptable salt and/or solvate thereof is an autism spectrum disorder.

In some embodiments, the autism spectrum disorder is selected from autism, Asperger's syndrome, childhood disintegrative disorder, Rett syndrome, and pervasive developmental disorder not otherwise specified.

The present application also includes a method of treating one or more symptoms of an autism spectrum disorder comprising administering a therapeutically effective amount of one or more compositions of comprising a non-racemic mixture a compound of Formula (R)-I, or a salt and/or solvate thereof, and (S)-I, or a salt and/or solvate thereof described above to a subject in need thereof.

The present application further includes a use of one or more compositions of comprising a non-racemic mixture a compound of Formula (R)-I, or a salt and/or solvate thereof, and (S)-I, or a salt and/or solvate thereof described above for treating one or more symptoms of an autism spectrum disorder, a use of one or more compositions of comprising a non-racemic mixture a compound of Formula (R)-I, or a salt and/or solvate thereof, and (S)-I, or a salt and/or solvate thereof described above for preparation of a medicament for treating one or more symptoms of an autism spectrum disorder, as well as one or more compositions of comprising a non-racemic mixture a compound of Formula (R)-I, or a salt and/or solvate thereof, and (S)-I, or a salt and/or solvate thereof described above for use to treat one or more symptoms of an autism spectrum disorder.

In some embodiments, the one or more symptoms of an autism spectrum disorder are selected from general anxiety, clinical anxiety, irritability, inappropriate speech, stereotypy, social withdrawal, repetitive behavior, and hyperactivity.

In some embodiments, the one or more symptoms of an autism spectrum disorder is selected from stereotypy and social withdrawal. In some embodiments, the one or more symptoms of an autism spectrum disorder is stereotypy. In some embodiments, the one or more symptoms of an autism spectrum disorder is social withdrawal. Accordingly, in some embodiments, compositions of comprising a non-racemic mixture a compound of Formula (R)-I, or a salt and/or solvate thereof, and (S)-I, or a salt and/or solvate thereof described above are for use to promote prosocial activity.

The Applicant has shown that the compositions of comprising a non-racemic mixture a compound of Formula (R)-I, or a salt and/or solvate thereof, and (S)-I, or a salt and/or solvate thereof described above promote pro-social behaviour in in vivo mice models of autism spectrum disorder. It has further been shown that the compositions of comprising a non-racemic mixture a compound of Formula (R)-I, or a salt and/or solvate thereof, and (S)-I, or a salt and/or solvate thereof described above do not influence locomotor activity in mice models of autism spectrum disorder. The Applicant has shown that S(+)-MDMA and racemic compositions of MDMA in BTBR mice elicit a dose dependent increase in temperature. However, exemplary compositions comprising a non-racemic mixture of a compound of Formula (R)-I, or a salt and/or solvate thereof, and (S)-I, or a salt and/or solvate thereof and compositions of pure R(−)-MDMA did not elicit significant effects on core temperature. It is known that hyperthermia results in cellular damage and neurotoxicity (Walter and Carraretto, Crit Care. 2016 Jul. 14; 20(1):199)

Further, it has been shown that stereotypy or hyperstimulation of mice is seen in mice dosed with S-MDMA and with high doses of racemic MDMA but not compositions of comprising a non-racemic mixture a compound of Formula (R)-I, or a salt and/or solvate thereof, and (S)-I, or a salt and/or solvate thereof described above.

Accordingly, in some embodiments, the administrating or use of the one or more compositions comprising a non-racemic mixture a compound of Formula (R)-I, or a salt and/or solvate thereof, and (S)-I, or a salt and/or solvate thereof described above has for treating one or more symptoms of an autism spectrum disorder has reduced adverse side effects compared to treatment with a racemic mixture of a compound of Formula I, or pharmaceutically acceptable a salt and/or solvate thereof.

Therefore, the present application also includes a method of treating one or more symptoms of an autism spectrum disorder and having reduced adverse side effects compared to treatment with a racemic mixture of a compound of Formula I, or pharmaceutically acceptable a salt and/or solvate thereof:

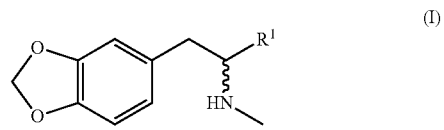

(I)

wherein
$R^1$ is selected from $CH_3$ and $CH_2CH_3$,
the method comprising administering a therapeutically effective amount of one or more compositions comprising a non-racemic mixture a compound of Formula (R)-I, or a salt and/or solvate thereof, and (S)-I, or a salt and/or solvate thereof described above to a subject in need thereof.

The present application further includes a use of one or more compositions of comprising a non-racemic mixture a compound of Formula (R)-I, or a salt and/or solvate thereof, and (S)-I, or a salt and/or solvate thereof described above for treating one or more symptoms of an autism spectrum disorder and reducing adverse side effects compared to treatment with a racemic mixture of a compound of Formula I, or pharmaceutically acceptable a salt and/or solvate thereof, a use of one or more compositions of comprising a non-racemic mixture a compound of Formula (R)-I, or a salt and/or solvate thereof, and (S)-I, or a salt and/or solvate thereof described above for preparation of a medicament for treating one or more symptoms of an autism spectrum disorder and reducing adverse side effects compared to treatment with a racemic mixture of a compound of Formula I, or pharmaceutically acceptable a salt and/or solvate thereof, as well as one or more compositions of comprising a non-racemic mixture a compound of Formula (R)-I, or a salt and/or solvate thereof, and (S)-I, or a salt and/or solvate thereof described above for use to treat one or more symptoms of an autism spectrum disorder and reducing adverse side effects compared to treatment with a racemic mixture of a compound of Formula I, or pharmaceutically acceptable a salt and/or solvate thereof.

In some embodiments, the one or more symptoms of an autism spectrum disorder is selected from stereotypy and social withdrawal and adverse side effect is selected from hyperthermia, stereotypy and neurotoxicity. In some embodiments, the one or more symptoms of an autism spectrum disorder is selected from stereotypy and social withdrawal and adverse side effect is selected from hyperthermia and neurotoxicity. In some embodiments, the one or more symptoms of an autism spectrum disorder is selected from stereotypy and social withdrawal and adverse side effect is selected from hyperthermia.

In some embodiments, the autistic spectrum disorder is, as defined by DSM-IV, wherein the one or more symptoms is selected from: (i) qualitative impairment in social interaction; (ii) qualitative impairment in communication; and (iii) restricted repetitive and stereotyped patterns of behaviour, interest and activities.

In some embodiments, one or more symptoms is selected from qualitative impairment in social interaction.

In some embodiments, the qualitative impairment in social interaction includes one or more of: marked impairment in the use of multiple nonverbal behaviours, including eye-to-eye gaze, facial expression, body postures, and gestures to regulate social interaction; failure to develop peer relationships appropriate to developmental level; (c) a lack of spontaneous seeking to share enjoyment, interests, or achievements with other people (e.g., by a lack of showing, bringing, or pointing out objects of interest); and (d) lack of social or emotional reciprocity.

In some embodiments, the qualitative impairment in communication include one or more of: delay in, or total lack of, the development of spoken language (not accompanied by an attempt to compensate through alternative modes of communication such as gesture or mime); in individuals with adequate speech, marked impairment in the ability to initiate or sustain a conversation with others; stereotyped and repetitive use of language or idiosyncratic language; and lack of varied, spontaneous make-believe play or social imitative play appropriate to developmental level.

In some embodiments, the restricted repetitive and stereotyped patterns of behaviour, interest and activities include one or more of: encompassing preoccupation with one or more stereotyped and restricted patterns of interest that is abnormal either in intensity or focus; apparently inflexible adherence to specific, non-functional routines or rituals; stereotyped and repetitive motor mannerisms (e.g., hand or finger flapping or twisting or complex whole-body movements); and persistent preoccupation with parts of objects.

In some embodiments, the one or more compositions comprising a non-racemic mixture a compound of Formula (R)-I, or a salt and/or solvate thereof, and (S)-I, or a salt and/or solvate thereof described above are administered or use as a second agent or "add-on" therapy.

In some embodiments, the one or more compositions comprising a non-racemic mixture a compound of Formula (R)-I, or a salt and/or solvate thereof, and (S)-I, or a salt and/or solvate thereof described above are administered before, during and/or after psychotherapy. In some embodiments, the one or more compositions comprising a non-racemic mixture a compound of Formula (R)-I, or a salt and/or solvate thereof, and (S)-I, or a salt and/or solvate thereof described above are administered during and/or after the psychotherapy.

In some embodiments, the psychotherapy is selected from behavior psychotherapy, exposure-based psychotherapy, cognitive psychotherapy, and psycho-dynamically oriented psychotherapy.

In some embodiments, the diseases, disorders or conditions that benefit from treatment with a racemic mixture of a compound of Formula I or a pharmaceutically acceptable salt and/or solvate thereof, are any diseases, disorders or conditions that benefits from treatment with L-3,4-dihydroxyphenylalanine (L-DOPA).

In some embodiments, the one or more compositions comprising a non-racemic mixture a compound of Formula (R)-I, or a salt and/or solvate thereof, and (S)-I, or a salt and/or solvate thereof described above are administered or used in combination with L-DOPA to treat the diseases, disorders or conditions that benefit from treatment with L-DOPA. In some embodiments, the one or more compositions comprising a non-racemic mixture a compound of Formula (R)-I, or a salt and/or solvate thereof, and (S)-I, or a salt and/or solvate thereof described above improve the efficacy of L-DOPA. In some embodiments, the one or more compositions comprising a non-racemic mixture a compound of Formula (R)-I, or a salt and/or solvate thereof, and (S)-I, or a salt and/or solvate thereof described above are administered or used in combination with L-DOPA to improve the efficacy of L-DOPA.

In some embodiments, the diseases, disorders or conditions that benefit from treatment with L-DOPA is Parkinson's Disease.

The present application also includes a method for treating Parkinson's Disease comprising administering a therapeutically effective amount of one or more compositions comprising a non-racemic mixture a compound of Formula (R)-I, or a salt and/or solvate thereof, and (S)-I, or a salt and/or solvate thereof described above to a subject in need thereof.

The present application further includes a use of one or more compositions comprising a non-racemic mixture a compound of Formula (R)-I, or a salt and/or solvate thereof, and (S)-I, or a salt and/or solvate thereof described above for treating Parkinson's Disease, a use of one or more compositions of the application for preparation of a medicament for treating Parkinson's Disease, as well as one or more compositions comprising a non-racemic mixture a compound of Formula (R)-I, or a salt and/or solvate thereof, and (S)-I, or a salt and/or solvate thereof described above for use to treat Parkinson's Disease.

In some embodiments, the one or more compositions comprising a non-racemic mixture a compound of Formula (R)-I, or a salt and/or solvate thereof, and (S)-I, or a salt and/or solvate thereof described above are administered or used in combination with L-DOPA to treat Parkinson's Disease. In some embodiments, the one or more compositions improve the efficacy of L-DOPA for treating Parkinson's Disease. In some embodiments, the one or more compositions comprising a non-racemic mixture a compound of Formula (R)-I, or a salt and/or solvate thereof, and (S)-I, or a salt and/or solvate thereof described above are administered or used in combination with L-DOPA to improve the efficacy of L-DOPA for treating Parkinson's Disease.

In some embodiments, the one or more compositions comprising a non-racemic mixture a compound of Formula (R)-I, or a salt and/or solvate thereof, and (S)-I, or a salt and/or solvate thereof described above improves the efficacy of L-DOPA by decreasing L-DOPA-induced dyskinesia.

Therefore, in some embodiments, the diseases, disorders or conditions that benefit from treatment with a racemic mixture of a compound of Formula I or a pharmaceutically acceptable salt and/or solvate thereof is dyskinesia. In some embodiments, the dyskinesia is L-DOPA-induced dyskinesia.

In some embodiments, the one or more compositions comprising a non-racemic mixture a compound of Formula (R)-I, or a salt and/or solvate thereof, and (S)-I, or a salt and/or solvate thereof described above improves the efficacy of L-DOPA by increasing the duration of antiparkinsonian benefits of L-DOPA (e.g. on-time). In some embodiments, the one or more compositions comprising a non-racemic mixture a compound of Formula (R)-I, or a salt and/or solvate thereof, and (S)-I, or a salt and/or solvate thereof described above improves the efficacy of L-DOPA by increasing the duration of antiparkinsonian benefits of L-DOPA without disabling dyskinesia.

In some embodiments, the one or more compositions comprising a non-racemic mixture a compound of Formula (R)-I, or a salt and/or solvate thereof, and (S)-I, or a salt and/or solvate thereof described above improves the efficacy of L-DOPA by decreasing L-DOPA-induced Parkinson disease psychosis.

Therefore, in some embodiments, the diseases, disorders or conditions that benefit from treatment with a racemic mixture of a compound of Formula I or a pharmaceutically acceptable salt and/or solvate thereof is L-DOPA-induced Parkinson disease psychosis.

By "decreasing L-DOPA-induced dyskinesia" or "decreasing L-DOPA-induced Parkinson disease psychosis" it is meant any diminishment of extent, stabilized (i.e., not worsening) state, delay or slowing of progression, amelioration or palliation, and remission (whether partial or total), whether detectable or undetectable of dyskinesia in the presence of one or more compositions comprising a non-racemic mixture a compound of Formula (R)-I, or a salt and/or solvate thereof, and (S)-I, or a salt and/or solvate thereof described above compared to otherwise identical conditions except in the absence of one or more compositions of the application.

By "increasing the duration of antiparkinsonian benefits of L-DOPA" it is meant any increase in the duration of antiparkinsonian benefits of L-DOPA compared to otherwise identical conditions except in the absence of one or more compositions comprising a non-racemic mixture a compound of Formula (R)-I, or a salt and/or solvate thereof, and (S)-I, or a salt and/or solvate thereof described above.

By "increasing the duration of antiparkinsonian benefits of L-DOPA without disabling dyskinesia" it is meant any increase in the duration of antiparkinsonian benefits of L-DOPA without disabling dyskinesia compared to otherwise identical conditions except in the absence of one or more compositions comprising a non-racemic mixture a compound of Formula (R)-I, or a salt and/or solvate thereof, and (S)-I, or a salt and/or solvate thereof described above.

It would be appreciated by a person skilled in the art that methods for the assessment of L-DOPA induced dyskinesia and/or psychosis are well known in the art, such as those found, for example, in Fox et al. 2006 Arch Neurol 63:1343-1344; Gomez-Ramirez et al. 2006, Mov Disord 21:839-846; Visanji et al. 2006, Mov Disord 21:1879-1891; Huot et al. Journal of Neuroscience, 2011, 31 (19) 7190-7198, and Fox et al. 2010 Can J Neurol Sci 37:86-95).

In some embodiments, the amount of a given composition comprising a non-racemic mixture a compound of Formula (R)-I, or a salt and/or solvate thereof, and (S)-I, or a salt and/or solvate thereof described above that will correspond to an effective amount will vary depending upon factors, such as the given composition(s), the pharmaceutical formulation, the route of administration, the type of condition, disease or disorder, the identity of the subject being treated, and the like, but can nevertheless be routinely determined by one skilled in the art. In an embodiment, the effective amount is one that, following treatment therewith, manifests as an improvement in or reduction of any disease, disorder or condition symptom, in particular compared to the disease, disorder or condition symptom without treatment.

In some embodiments, the compositions comprising a non-racemic mixture a compound of Formula (R)-I, or a salt and/or solvate thereof, and (S)-I, or a salt and/or solvate thereof described above are administered at least once a week. In some embodiments, the compositions comprising a non-racemic mixture a compound of Formula (R)-I, or a salt and/or solvate thereof, and (S)-I, or a salt and/or solvate thereof described above are administered from about one time per two weeks, three weeks or one month. In some embodiments, the compositions comprising a non-racemic mixture a compound of Formula (R)-I, or a salt and/or solvate thereof, and (S)-I, or a salt and/or solvate thereof described above are administered about one time per week to about once daily. In some embodiments, the compositions of the application are administered 2, 3, 4, 5 or 6 times daily. The length of the treatment period depends on a variety of factors, such as the severity of the disease, disorder or condition, the age of the subject, the concentration and/or the activity of the compositions of the application, and/or a combination thereof.

It will also be appreciated that the effective dosage of the compositions comprising a non-racemic mixture a compound of Formula (R)-I, or a salt and/or solvate thereof, and (S)-I, or a salt and/or solvate thereof described above used for the treatment may increase or decrease over the course of a particular treatment regime. Changes in dosage may result and become apparent by standard diagnostic assays known in the art. In some instances, chronic administration is required. For example, the compositions comprising a non-racemic mixture a compound of Formula (R)-I, or a salt and/or solvate thereof, and (S)-I, or a salt and/or solvate thereof described above are administered to the subject in an amount and for duration sufficient to treat the subject.

In some embodiments, the subject is a mammal. In some embodiments, the subject is human. In some embodiments, the subject is a non-human animal. In some embodiments, the subject is canine. In some embodiments, the subject is feline. Accordingly, the compositions, methods and uses of the present application are directed to both human and veterinary diseases, disorders and conditions.

Compositions comprising a non-racemic mixture a compound of Formula (R)-I, or a salt and/or solvate thereof, and (S)-I, or a salt and/or solvate thereof described above are either used alone or in combination with other known agents useful for treating diseases, disorders or conditions that benefit from treatment with psychotherapy. When used in combination with other agents useful in treating diseases, disorders or conditions benefits from treatment with psychotherapy, it is an embodiment that a composition comprising a non-racemic mixture a compound of Formula (R)-I, or a salt and/or solvate thereof, and (S)-I, or a salt and/or solvate thereof described above is administered contemporaneously with those agents. As used herein, "contemporaneous administration" of two substances to a subject means providing each of the two substances so that they are both active in the individual at the same time. The exact details of the administration will depend on the pharmacokinetics of the substances in the presence of each other, and can include administering the substances within a few hours of each other, or even administering one substance within 24 hours of administration of the other, if the pharmacokinetics are suitable. Design of suitable dosing regimens is routine for one skilled in the art. In particular embodiments, substances will be administered substantially simultaneously, i.e., within minutes of each other, or in a single composition that contains all substances. It is a further embodiment of the present application that a combination of agents is administered to a subject in a non-contemporaneous fashion.

The dosage of a composition comprising a non-racemic mixture a compound of Formula (R)-I, or a salt and/or solvate thereof, and (S)-I, or a salt and/or solvate thereof described above varies depending on many factors such as the pharmacodynamic properties of the compound, the mode of administration, the age, health and weight of the recipient, the nature and extent of the symptoms, the frequency of the treatment and the type of concurrent treatment, if any, and the clearance rate of the compound in the subject to be treated. One of skill in the art can determine the appropriate dosage based on the above factors. In some embodiments, a composition of the application is administered initially in a suitable dosage that is adjusted as required, depending on the clinical response.

(ii) Methods and Uses of (R)-MDMA

The R enantiomer of MDMA ((R)-MDMA) has been shown to have an improved toxicological profile while maintaining the therapeutic effects of MDMA racemate.

Therefore, (R)-MDMA can be used in a method of reducing adverse side effects of treatment with a racemic MDMA, or a pharmaceutically acceptable salt and/or solvate thereof, the method comprising administering a therapeutically effective amount of (R)-MDMA, or a pharmaceutically acceptable salt and/or solvate thereof, to a subject in need thereof.

The present application further includes a use of (R)-MDMA or a pharmaceutically acceptable salt and/or solvate thereof for reducing adverse side effects of treatment with a racemic MDMA, or a pharmaceutically acceptable salt and/or solvate thereof; a use of (R)-MDMA or a pharmaceutically acceptable salt and/or solvate thereof for preparing a medicament for reducing adverse side effects of treatment with a racemic MDMA, or a pharmaceutically acceptable salt and/or solvate thereof, as well as (R)-MDMA for use to reduce adverse side effects of treatment with a racemic MDMA, or a pharmaceutically acceptable salt and/or solvate.

In some embodiments, the adverse side effects are selected from one or more of neurotoxicity, hyperthermia, and substance use disorder. In some embodiments, the substance use disorder is drug abuse or drug dependence. In some embodiments, the substance use disorder is drug abuse of the compounds of Formula I.

Accordingly, in some embodiments, the adverse side effect is one or more of hyperthermia and neurotoxicity.

Reports have suggested that long term use of MDMA could lead to heart valve fibroplasia and disfunction, such as valvular heart disease (VHD). Therefore, in some embodiments, the adverse side effects are cardiotoxicity. In some embodiments, the cardiotoxicity is heart valve fibroplasia and disfunction. In some embodiments, the cardiotoxicity is valvular heart disease. Therefore, in some embodiments, the adverse side effect is valvular heart disease.

Accordingly, (R)-MDMA, for example, may be useful for the treatment of various diseases, disorders or conditions that benefit from treatment with racemic MDMA, or a pharmaceutically acceptable salt and/or solvate thereof.

Therefore, the present application also includes a method for treating diseases, disorders or conditions that benefit from treatment with racemic MDMA, or a pharmaceutically acceptable salt and/or solvate thereof, the method comprising administering a therapeutically effective amount of (R)-MDMA, or a pharmaceutically acceptable salt and/or solvate thereof, to a subject in need thereof.

The present application further includes a use of (R)-MDMA, or a pharmaceutically acceptable salt and/or solvate thereof, for treating diseases, disorders or conditions that benefit from treatment with racemic MDMA, or a pharmaceutically acceptable salt and/or solvate thereof, a use of (R)-MDMA, or a pharmaceutically acceptable salt and/or solvate thereof, for preparation of a medicament for treating diseases, disorders or conditions that benefit from treatment with racemic MDMA, or a pharmaceutically acceptable salt and/or solvate thereof, as well as (R)-MDMA, or a pharmaceutically acceptable salt and/or solvate thereof, for use to treat diseases, disorders or conditions that benefit from treatment with racemic MDMA, or a pharmaceutically acceptable salt and/or solvate thereof.

The Applicant has shown that S(+)-MDMA and racemic compositions of MDMA in BTBR mice elicit a dose dependent increase in temperature. However, exemplary compositions comprising a non-racemic mixture a compound of Formula (R)-I, or a salt and/or solvate thereof, and (S)-I, or a salt and/or solvate thereof and compositions of pure R(−)-MDMA did not elicit significant effects on core temperature. It is known that hyperthermia results in cellular damage and neurotoxicity (Walter and Carraretto, Crit Care. 2016 Jul. 14; 20(1):199).

In some embodiments, the administrating or use of (R)-MDMA, or a pharmaceutically acceptable salt and/or solvate thereof has reduced adverse side effects compared to treatment with a racemic MDMA, or a pharmaceutically acceptable salt and/or solvate thereof.

Accordingly, in some embodiments, the application includes a method for treating diseases, disorders or conditions that benefit from treatment with racemic MDMA, or a pharmaceutically acceptable salt and/or solvate thereof and having reduced adverse side effects compared to treatment with racemic MDMA, or a pharmaceutically acceptable salt and/or solvate thereof;

the method comprising administering a therapeutically effective amount of (R)-MDMA, or a pharmaceutically acceptable salt and/or solvate thereof to a subject in need thereof.

The present application further includes a use of (R)-MDMA, or a pharmaceutically acceptable salt and/or solvate thereof for treating diseases, disorders or conditions that benefit from treatment with racemic MDMA, or a pharmaceutically acceptable salt and/or solvate thereof and having reduced adverse side effects compared to treatment with a racemic MDMA, or a pharmaceutically acceptable salt and/or solvate thereof, a use of (R)-MDMA, or a pharmaceutically acceptable salt and/or solvate thereof for preparation of a medicament for treating diseases, disorders or conditions that benefit from treatment with racemic MDMA, or a pharmaceutically acceptable salt and/or solvate thereof and having reduced adverse side effects compared to treatment with a racemic MDMA, or a pharmaceutically acceptable salt and/or solvate thereof, as well as (R)-MDMA, or a pharmaceutically acceptable salt and/or solvate thereof for use to treat diseases, disorders or conditions that benefit from treatment with racemic MDMA, or a pharmaceutically acceptable salt and/or solvate thereof and having reduced adverse side effects compared to treatment with a racemic MDMA, or a pharmaceutically acceptable salt and/or solvate thereof.

In some embodiments, the adverse side effects are selected from one or more of neurotoxicity, hyperthermia, and substance use disorder. In some embodiments, the substance use disorder is drug abuse or drug dependence. In some embodiments, the substance use disorder is drug abuse of the compounds of Formula I.

In some embodiments, the adverse side effects are selected from one or more of hyperthermia and neurotoxicity. In some embodiments, the adverse side effect is hyperthermia.

In some embodiments, the diseases, disorders or conditions that benefit from treatment with racemic MDMA, or a pharmaceutically acceptable salt and/or solvate thereof, are any disease, disorder or condition that benefits from psychotherapy, including but not limited to one or more of post-traumatic stress disorder (PTSD), social anxiety disorder, depression, alcohol addiction, and eating disorders.

In some embodiments, (R)-MDMA, or a pharmaceutically acceptable salt and/or solvate thereof, is administered or used in combination with psychotherapy to treat the diseases, disorders or conditions. In some embodiments, the (R)-MDMA, or a pharmaceutically acceptable salt and/or solvate thereof, improves the efficacy of psychotherapy. In some embodiment, the psychotherapy is for psychiatric disorders.

In some embodiments, the diseases, disorders or conditions that benefit from treatment with racemic MDMA, or a pharmaceutically acceptable salt and/or solvate thereof, are one or more psychiatric disorders. In some embodiments, the one or more psychiatric disorders are selected from one or more of anxiety disorders, mood disorders, developmental disorders, substance use disorders and addictions, eating disorders, personality disorders and psychotic disorders. In some embodiments, the substance use disorder is drug abuse or drug dependence.

In some embodiments, the anxiety disorder is selected from one or more of obsessive-compulsive disorder (OCD), social anxiety disorder, phobias, panic disorder and post-traumatic stress disorder (PTSD). In some embodiments, the anxiety disorder is social anxiety disorder. In some embodiments, the anxiety disorder is PTSD.

In some embodiments, the mood disorder is selected from one or both of depression and bipolar disorder.

In some embodiments, the developmental disorder is selected from an autism spectrum disorder (ASD). In some embodiments, the developmental disorder is Asperger syndrome.

In some embodiments, the substance use disorders and addictions are selected from one or more of alcoholism, drug abuse, drug dependence and compulsive gambling. In some embodiments, the drug dependence is opioid dependence. In some embodiments, the substance use disorder is opioid use disorder.

In some embodiments, the eating disorder is selected from anorexia and bulimia.

In some embodiments, the personality disorder is selected from borderline personality disorder and dependent personality disorder In some embodiments, the psychotic disorders are selected from schizophrenia and other disorders that cause detachment from reality.

In some embodiments, the one or more psychiatric disorders are selected from one or more of autism spectrum disorder (ASD), depression and drug dependence. In some embodiments, the depression is clinical depression, for example, in palliative care subjects.

In some embodiments, the one or more psychiatric disorders are selected from post-traumatic stress disorder (PTSD), eating disorder and alcoholism. In some embodiments, the one or more psychiatric disorders is post-traumatic stress disorder (PTSD).

In some embodiments, the one or more psychiatric disorders are selected from an autism spectrum disorder (ASD), depression and drug dependence. In some embodiments, the depression is clinical depression, for example, in palliative care subjects. In some embodiments, the substance use disorder is opioid use disorder.

In some embodiments, the diseases, disorders or conditions that benefit from treatment with racemic MDMA, or a pharmaceutically acceptable salt and/or solvate thereof, is an autism spectrum disorder.

In some embodiments, the autism spectrum disorder is selected from autism, Asperger's syndrome, childhood disintegrative disorder, Rett syndrome, and pervasive developmental disorder not otherwise specified.

The present application also includes a method of treating one or more symptoms of an autism spectrum disorder comprising administering a therapeutically effective amount of (R)-MDMA, or a pharmaceutically acceptable salt and/or solvate thereof, to a subject in need thereof.

The present application further includes a use (R)-MDMA, or a pharmaceutically acceptable salt and/or solvate thereof, for treating one or more symptoms of an autism spectrum disorder, a use of (R)-MDMA, or a pharmaceutically acceptable salt and/or solvate thereof, for preparation of a medicament for treating one or more symptoms of an autism spectrum disorder, as well as (R)-MDMA, or a pharmaceutically acceptable salt and/or solvate thereof, for use to treat one or more symptoms of an autism spectrum disorder.

In some embodiments, the one or more symptoms are selected from general anxiety, clinical anxiety, irritability, inappropriate speech, stereotypy, social withdrawal, repetitive behavior, and hyperactivity.

In some embodiments, the one or more symptoms of an autism spectrum disorder is selected from stereotypy and social withdrawal. In some embodiments, the one or more symptoms of an autism spectrum disorder is stereotypy. In some embodiments, the one or more symptoms of an autism spectrum disorder is social withdrawal. Accordingly, in some embodiments, (R)-MDMA, or a pharmaceutically acceptable salt and/or solvate thereof are for use to promote prosocial activity.

The Applicant has shown that (R)-MDMA, or a pharmaceutically acceptable salt and/or solvate thereof promotes pro-social behaviour in in vivo mice models of autism spectrum disorder. It has further been shown that (R)-MDMA and the compositions of comprising a non-racemic mixture a compound of Formula (R)-I, or a salt and/or solvate thereof, and (S)-I, or a salt and/or solvate thereof described above do not influence locomotor activity in mice models of autism spectrum disorder. The Applicant has shown that S(+)-MDMA and racemic compositions of MDMA in BTBR mice elicit a dose dependent increase in temperature. However, exemplary compositions comprising a non-racemic mixture of a compound of Formula (R)-I, or a salt and/or solvate thereof, and (S)-I, or a salt and/or solvate thereof and compositions of pure R(−)-MDMA did not elicit significant effects on core temperature. It is known that hyperthermia results in cellular damage and neurotoxicity (Walter and Carraretto, Crit Care. 2016 Jul. 14; 20(1): 199)

Further, it has been shown that stereotypy or hyperstimulation of mice is seen in mice dosed with S-MDMA and with high doses of racemic MDMA but not compositions of comprising a non-racemic mixture a compound of Formula (R)-I, or a salt and/or solvate thereof, and (S)-I, or a salt and/or solvate thereof described above.

Therefore, in some embodiments, the administrating or use of (R)-MDMA, or a pharmaceutically acceptable salt and/or solvate thereof has reduced adverse side effects compared to treatment with a racemic MDMA, or a pharmaceutically acceptable salt and/or solvate thereof.

Therefore, the present application also includes a method of treating one or more symptoms of an autism spectrum disorder and having reduced adverse side effects compared to treatment with racemic MDMA, or a pharmaceutically acceptable salt and/or solvate thereof, the method comprising administering a therapeutically effective amount of (R)-MDMA, or a pharmaceutically acceptable salt and/or solvate thereof to a subject in need thereof.

The present application further includes a use of (R)-MDMA, or a pharmaceutically acceptable salt and/or solvate thereof for treating one or more symptoms of an autism spectrum and having reduced adverse side effects compared to treatment with racemic MDMA, or a pharmaceutically acceptable salt and/or solvate thereof, a use of (R)-MDMA, or a pharmaceutically acceptable salt and/or solvate thereof for preparation of a medicament for treating one or more symptoms of an autism spectrum disorder and having reduced adverse side effects compared to treatment with racemic MDMA, or a pharmaceutically acceptable salt and/ or solvate thereof, as well as (R)-MDMA, or a pharmaceutically acceptable salt and/or solvate thereof for use to treat one or more symptoms of an autism spectrum disorder and having reduced adverse side effects compared to treatment with racemic MDMA, or a pharmaceutically acceptable salt and/or solvate thereof.

In some embodiments, the one or more symptoms of an autism spectrum disorder is selected from stereotypy and social withdrawal and adverse side effect is selected from hyperthermia, stereotypy and neurotoxicity. In some embodiments, the one or more symptoms of an autism spectrum disorder is selected from stereotypy and social withdrawal and adverse side effect is selected from hyperthermia and neurotoxicity. In some embodiments, the one or more symptoms of an autism spectrum disorder is selected from stereotypy and social withdrawal and adverse side effect is selected from hyperthermia.

In some embodiments, the autistic spectrum disorder is, as defined by DSM-IV, wherein the one or more symptoms is selected from: (i) qualitative impairment in social interaction; (ii) qualitative impairment in communication; and (iii) restricted repetitive and stereotyped patterns of behaviour, interest and activities.

In some embodiments, one or more symptoms is selected from qualitative impairment in social interaction.

In some embodiments, the qualitative impairment in social interaction include one or more of: marked impairment in the use of multiple nonverbal behaviours, including eye-to-eye gaze, facial expression, body postures, and gestures to regulate social interaction; failure to develop peer relationships appropriate to developmental level; (c) a lack of spontaneous seeking to share enjoyment, interests, or achievements with other people (e.g., by a lack of showing, bringing, or pointing out objects of interest); and (d) lack of social or emotional reciprocity.

In some embodiments, the qualitative impairment in communication include one or more of: delay in, or total lack of, the development of spoken language (not accompanied by an attempt to compensate through alternative modes of communication such as gesture or mime); in individuals with adequate speech, marked impairment in the ability to initiate or sustain a conversation with others; stereotyped and repetitive use of language or idiosyncratic language; and lack of varied, spontaneous make-believe play or social imitative play appropriate to developmental level.

In some embodiments, the restricted repetitive and stereotyped patterns of behaviour, interest and activities include one or more of: encompassing preoccupation with one or more stereotyped and restricted patterns of interest that is abnormal either in intensity or focus; apparently inflexible adherence to specific, non-functional routines or rituals; stereotyped and repetitive motor mannerisms (e.g., hand or finger flapping or twisting or complex whole-body movements); and persistent preoccupation with parts of objects.

In some embodiments, (R)-MDMA, or a pharmaceutically acceptable salt and/or solvate thereof, is administered or used as a second agent or "add-on" therapy.

In some embodiments, the (R)-MDMA, or a pharmaceutically acceptable salt and/or solvate thereof, is administered before, during and/or after psychotherapy. In some embodiments, the (R)-MDMA, or a pharmaceutically acceptable salt and/or solvate thereof, is administered during and/or after the psychotherapy.

In some embodiments, the psychotherapy is selected from behavior psychotherapy, exposure-based psychotherapy, cognitive psychotherapy, and psycho-dynamically oriented psychotherapy.

The present application also includes a method for treating Parkinson's Disease comprising administering a therapeutically effective amount of (R)-MDMA, or a pharmaceutically acceptable salt and/or solvate thereof to a subject in need thereof.

The present application further includes a use of (R)-MDMA, or a pharmaceutically acceptable salt and/or solvate thereof for treating Parkinson's Disease, a use of the (R)-MDMA, or a pharmaceutically acceptable salt and/or solvate thereof for preparation of a medicament for treating Parkinson's Disease, as well as (R)-MDMA, or a pharmaceutically acceptable salt and/or solvate thereof for use to treat Parkinson's Disease.

In some embodiments, the (R)-MDMA has an enantiomeric purity of greater than 99%.

In some embodiments, the amount of (R)-MDMA, or a pharmaceutically acceptable salt and/or solvate thereof, that will correspond to an effective amount will vary depending upon factors, such as the pharmaceutical formulation, the route of administration, the type of condition, disease or disorder, the identity of the subject being treated, and the like, but can nevertheless be routinely determined by one skilled in the art. In an embodiment, the effective amount is one that, following treatment therewith, manifests as an improvement in or reduction of any disease, disorder or condition symptom, in particular compared to the disease, disorder or condition symptom without treatment.

In an embodiment, the (R)-MDMA, or a pharmaceutically acceptable salt and/or solvate thereof, are administered at least once a week. However, in another embodiment, the (R)-MDMA, or a pharmaceutically acceptable salt and/or solvate thereof, is administered to the subject from about one time per two weeks, three weeks or one month. In another embodiment, the (R)-MDMA, or a pharmaceutically acceptable salt and/or solvate thereof, is administered about one time per week to about once daily. In another embodiment, the (R)-MDMA, or a pharmaceutically acceptable salt and/ or solvate thereof, is administered 2, 3, 4, 5 or 6 times daily. The length of the treatment period depends on a variety of factors, such as the severity of the disease, disorder or condition, the age of the subject, the concentration and/or the activity of the (R)-MDMA, or a pharmaceutically acceptable salt and/or solvate thereof, and/or a combination thereof. It will also be appreciated that the effective dosage of the (R)-MDMA, or a pharmaceutically acceptable salt and/or solvate thereof, used for the treatment may increase or decrease over the course of a particular treatment regime. Changes in dosage may result and become apparent by standard diagnostic assays known in the art. In some instances, chronic administration is required. For example, the (R)-MDMA, or a pharmaceutically acceptable salt and/or solvate thereof, is administered to the subject in an amount and for duration sufficient to treat the subject.

In an embodiment, the subject is a mammal. In another embodiment, the subject is human. In an embodiment, the subject is a non-human animal. In an embodiment, the subject is canine. In an embodiment, the subject is feline. Accordingly, the methods and uses of the present application are directed to both human and veterinary diseases, disorders and conditions.

(R)-MDMA, or a pharmaceutically acceptable salt and/or solvate thereof, is either used alone or in combination with other known agents useful for treating diseases, disorders or conditions that benefit with treatment of psychotherapy. When used in combination with other agents useful in treating diseases, disorders or conditions benefits from treatment with psychotherapy, it is an embodiment that (R)-MDMA, or a pharmaceutically acceptable salt and/or solvate thereof, is administered contemporaneously with those agents. As used herein, "contemporaneous administration" of two substances to a subject means providing each of the two substances so that they are both active in the individual at the same time. The exact details of the administration will depend on the pharmacokinetics of the two substances in the presence of each other and can include administering the two substances within a few hours of each other, or even administering one substance within 24 hours of administration of the other, if the pharmacokinetics are suitable. Design of suitable dosing regimens is routine for one skilled in the art. In particular embodiments, two substances will be administered substantially simultaneously, i.e., within minutes of each other, or in a single composition that contains both substances. It is a further embodiment of the present application that a combination of agents is administered to a subject in a non-contemporaneous fashion.

The dosage of (R)-MDMA, or a pharmaceutically acceptable salt and/or solvate thereof, varies depending on many factors such as the pharmacodynamic properties of the compound, the mode of administration, the age, health and weight of the recipient, the nature and extent of the symptoms, the frequency of the treatment and the type of concurrent treatment, if any, and the clearance rate of the (R)-MDMA, or a pharmaceutically acceptable salt and/or solvate thereof, in the subject to be treated. One of skill in the art can determine the appropriate dosage based on the above factors.

In some embodiments, the dosage of (R)-MDMA, or a pharmaceutically acceptable salt and/or solvate thereof is about 40 mg to about 180 mg. In some embodiments, the dosage of (R)-MDMA, or a pharmaceutically acceptable salt and/or solvate thereof is about 40 mg, 60 mg, 75 mg, 80 mg, 100 mg, 120 mg or 125 m. In some embodiments, depending on the mode of administration, the compositions of the application are pharmaceutical compositions that comprise about 0.05 wt % to about 99 wt % or about 0.10 wt % to about 70 wt % of (R)-MDMA, or a pharmaceutically acceptable salt and/or solvate thereof and from about 1 wt % to about 99.95 wt % or about 30 wt % to about 99.90 wt % of one or more pharmaceutically acceptable carriers, all percentages by weight being based on the total composition.

(R)-MDMA or a pharmaceutically acceptable salt and/or solvate thereof is suitably formulated in a conventional manner into compositions using one or more carriers. Accordingly, the present application also includes a composition comprising (R)-MDMA or a pharmaceutically acceptable salt and/or solvate thereof and a carrier. The compounds of the application are suitably formulated into pharmaceutical compositions for administration to subjects in a biologically compatible form suitable for administration in vivo. Accordingly, the present application further includes a pharmaceutical composition comprising (R)-MDMA or a pharmaceutically acceptable salt and/or solvate thereof and a pharmaceutically acceptable carrier.

In embodiments of the application the pharmaceutical compositions of (R)-MDMA or a pharmaceutically acceptable salt and/or solvate thereof are used in the treatment of any of the diseases, disorders or conditions described herein.

(R)-MDMA or a pharmaceutically acceptable salt and/or solvate thereof is administered to a subject in a variety of forms depending on the selected route of administration, as will be understood by those skilled in the art. For example, the variety of forms and routes of administration described in the "Non-Racemic Compositions of the application" section above A marked difference in the Cmax of MDMA in rats based on the route of delivery has been observed (Baumann M H et al., Drug Metab Dispos. 2009; 37(11):2163-70). At 2 mg/kg, maximum MDMA concentrations were ~200 ng/ml for intraperitoneal (210 ng/ml) and subcutaneous routes (196 ng/ml), but less for the oral route (46 ng/ml). At higher doses, (10 mg/kg), Cmax via intraperitoneal (2257 ng/ml), and subcutaneous (1130 ng/ml) route of administration was higher than via oral route (966 ng/ml).

It is also known that the (R)- and (S)-enantiomers of racemic 3,4-methylenedioxymethamphetamine (MDMA) exhibit different dose-concentration curves. MDMA, MDA, DHMA, DHMA sulfates, HMMA, HMMA sulphates, and HMMA glucuronides have been shown to be excreted in human urine in substantial amounts (Schwaninger A E, et al. Biochem Pharmacol. 2012; 83(1):131-8). Statistically significant differences between the two enantiomers ((R)- and (S)- of individual metabolites) were observed for all compounds, except HMMA sulfate after creatinine normalization. Higher R-enantiomer Cmax was observed for MDMA, DHMA and HMMA sulfate, whereas S-enantiomers were higher for DHMA sulphate, HMMA, HMMA glucuronide, and MDA.

The oral mucosa is occasionally used as the site of drug absorption. Sublingual administration, in which a tablet or troche is allowed to dissolve completely in the oral cavity, takes advantage of the permeability of the oral epithelium and is the route of administration for a few potent lipophilic drugs, such as nitroglycerin and oxytocin, and even the oral sedative triazolam.

MDMA has demonstrated efficacy in phase 3 trials to treat Post Traumatic Stress Disorder (PTSD) via MDMA-assisted psychotherapy. It is known to have complex pharmacology and impact multiple receptors in the brain.

In some embodiments, intranasal administration is believed to offer both direct and indirect pathways to the delivery of psychopharmacological agents to the central nervous system (CNS). Direct nose-to-brain transport via olfactory and trigeminal nerve pathways after intranasal deposition and absorption on the olfactory and respiratory epithelia provides a non-invasive means of circumventing the blood-brain barrier (BBB), which is an obstacle for drug delivery to CNS. Further, in some embodiments, in comparison to other routes of administration (e.g oral administration) intranasal offers ease of use, reduced systemic exposure, faster drug onset, increased compliance, and greater bioavailability by avoiding first-pass metabolism (Keller et al. Drug Deliv. and Transl. Res. 12, 735-757 (2022)).

Therefore, in some embodiments, sublingual and intranasal administration avoids drug destruction. In some embodiments, sublingual and intranasal administration avoids drug destruction by bypassing gastric acid and intestinal and hepatic enzymes.

In some embodiments, sublingual and intranasal absorption is more efficient compared to intestinal uptake, for example, when using oral administration. In some embodiments, the onset of drug effects using sublingual or intranasal administration is faster compared to the onset of the same drug effects using oral administration.

In some embodiments, a better drug absorption and metabolic profile is achieved when using sublingual or intranasal administration compared to oral administration. In some embodiments, hepatic metabolism is more subdued using sublingual or intranasal administration compared to oral administration. In some embodiments, a lower dose of an active ingredient, e.g., MDMA, is used to achieve a biological effect by sublingual or intranasal administration compared to the dose of an active ingredient to achieve the same biological effect by oral administration. In some embodiments, sublingual or intranasal administration affords better bioavailability and a better safety profile for an active ingredient, e.g., MDMA compared with oral administration.

Therefore, in some embodiments, the compositions of (R)-MDMA or a pharmaceutically acceptable salt and/or solvate thereof are formulated for intranasal or sublingual administration or use. In some embodiments, the compositions of (R)-MDMA or a pharmaceutically acceptable salt and/or solvate thereof are formulated for intranasal administration or use.

Therefore, in some embodiments, the present application also includes an intranasal composition comprising (R)-MDMA or a pharmaceutically acceptable salt and/or solvate thereof.

In some embodiments, the R enantiomer of MDMA ((R)-MDMA) or a pharmaceutically acceptable salt and/or solvate thereof is as described above.

In some embodiments, the intranasal compositions comprising (R)-MDMA or a pharmaceutically acceptable salt and/or solvate thereof are for use or administration in the treatment of any of the diseases, disorders or conditions described herein.

In some embodiments, the intranasal compositions comprising (R)-MDMA or a pharmaceutically acceptable salt and/or solvate thereof are conveniently formulated as aerosols, drops, gels and powders. For intranasal administration or administration by inhalation, the compositions of the application are conveniently delivered in the form of a solution, dry powder formulation or suspension from a pump spray container that is squeezed or pumped by the subject or as an aerosol spray presentation from a pressurized container or a nebulizer. Aerosol compositions typically comprise a solution or fine suspension of the compositions of the application in a physiologically acceptable aqueous or non-aqueous solvent and are usually presented in single or multidose quantities in sterile form in a sealed container, which, for example, take the form of a cartridge or refill for use with an atomising device. Alternatively, the sealed container is a unitary dispensing device such as a single dose nasal inhaler or an aerosol dispenser fitted with a metering valve which is intended for disposal after use. Where the dosage form comprises an aerosol dispenser, it will contain a propellant which is, for example, a compressed gas such as compressed air or an organic propellant such as fluorochlorohydrocarbon. Suitable propellants include but are not limited to dichlorodifluoromethane, trichlorofluoromethane, dichlorotetrafluoroethane, heptafluoroalkanes, carbon dioxide or another suitable gas. In the case of a pressurized aerosol, the dosage unit is suitably determined by providing a valve to deliver a metered amount. In some embodiments, the pressurized container or nebulizer contains a solution or suspension of the compositions of the application. Capsules and cartridges (made, for example, from gelatin) for use in an inhaler or insufflator are, for example, formulated containing a powder mix of a composition of the application and a suitable powder base such as lactose or starch. The aerosol dosage forms can also take the form of a pump-atomizer.

In some embodiments, the intranasal compositions comprising (R)-MDMA or a pharmaceutically acceptable salt and/or solvate thereof is formulated as an aerosol for use with a pump-atomizer.

In some embodiments, the intranasal compositions comprising (R)-MDMA or a pharmaceutically acceptable salt and/or solvate thereof is a powder. In some embodiments, the powder is a dry powder. In some embodiment, the dry powder is formulated to be reconstituted with a suitable vehicle before use or administration. In some embodiments the suitable vehicle is sterile pyrogen-free water.

In some embodiments, the powder is formulated for use or administration with an inhaler or insufflator. Accordingly, in some embodiments, the dry powder is formulated for use or administration as a capsule and cartridge for use with an inhaler or insufflator.

In some embodiments, the dry powder further comprises a suitable powder base. In some embodiment, the suitable powder based comprise lactose or starch.

In some embodiments, the intranasal compositions comprising (R)-MDMA or a pharmaceutically acceptable salt and/or solvate thereof further comprises water. Therefore, in some embodiments, the intranasal pharmaceutical composition further comprises water and is an aqueous intranasal pharmaceutical composition.

In some embodiments, the intranasal compositions comprising (R)-MDMA or a pharmaceutically acceptable salt and/or solvate thereof is a solution, suspension or emulsion. In some embodiments, the intranasal compositions comprising (R)-MDMA or a pharmaceutically acceptable salt and/or solvate thereof is a solution.

In some embodiments, the aqueous the intranasal compositions comprising (R)-MDMA or a pharmaceutically acceptable salt and/or solvate thereof is formulated for administration into nose in the form of drops. In some embodiments, the aqueous the intranasal compositions comprising (R)-MDMA or a pharmaceutically acceptable salt and/or solvate thereof is formulated for administration as a nasal spray. In some embodiments, the nasal spray is delivered in the form of a solution or suspension from a pump spray container that is squeezed or pumped by the patient or as an aerosol spray presentation from a pressurized container or a nebulizer. In some embodiments, the aqueous intranasal pharmaceutical composition is formulated as an aerosol for use with a pump-atomizer.

In some embodiments, the water is present in the intranasal pharmaceutical composition in an amount of about 50% to about 75%, about 50% to about 70%, about 50% to about 65%, about 33% to about 75%, about 55% to about 70% or about 55% to about 65% by weight of the composition. In some embodiments, the water is present in an amount of about 50%, about 60%, about 65% or about 70% by weight of the composition. In some embodiments, the water is present in an amount of about 55% to about 65% by weight of the composition. In some embodiments, the water is about 60% by weight of the composition.

Compositions suitable for buccal or sublingual administration include tablets, lozenges, and pastilles, wherein the compositions of the application are formulated with a carrier such as sugar, acacia, tragacanth, or gelatin and glycerine. Compositions for rectal administration are conveniently in the form of suppositories containing a conventional suppository base such as cocoa butter.

In some embodiments, the compositions of (R)-MDMA or a pharmaceutically acceptable salt and/or solvate thereof are formulated for sublingual administration or use.

Therefore, in some embodiments, the present application also includes a sublingual composition comprising (R)-MDMA or a pharmaceutically acceptable salt and/or solvate thereof.

In some embodiments, the sublingual compositions (R)-MDMA or a pharmaceutically acceptable salt and/or solvate thereof are used or administered in the treatment of any of the diseases, disorders or conditions described herein.

In some embodiments, the sublingual compositions are formulated as tablets, drops, strips, sprays, lozenges or effervescent tablets.

EXAMPLES

The following non-limiting examples are illustrative of the present application:

Example 1: Exemplary Compositions of the Application

Exemplary Composition 1 (ALA001): 90-99% (R)-MDMA, 1-10% (S)-MDMA
Exemplary Composition 2 (ALA002): 80-89.9% (R)-MDMA, 10.1%-20% (S)-MDMA
Exemplary Composition 2(i): 80% (R)-MDMA and 20% (S)-MDMA. 80% (R)-MDMA and 20% (S)-MDMA were dissolved in physiological 0.9%. Exemplary composition 2(i) was tested at various doses in the examples below, for example, 3 mg/kg and 10 mg/kg.
Exemplary Composition 3 (ALA003): 70-79.9% (R)-MDMA, 20.1-30% (S)-MDMA
Exemplary Composition 4 (ALA004): 90-99% (R)-MBDB, 1-10% (S)-MBDB
Exemplary Composition 5 (ALA005): 80-89.9% (R)-MBDB, 10.1%-20% (S)-MBDB
Exemplary Composition 6 (ALA006): 70-79.9% (R)-MBDB, 20.1-30% (S)-MBDB
Exemplary Composition 7: (R)-MDMA (>99% R enantiomer)
Comparative Composition 1: Racemic MDMA
Comparative Composition 2: Racemic MBDB
Comparative Composition 3: (S)-MDMA (>99% S enantiomer)

In the in-vivo studies below, all drugs, (R)-MDMA, (S)-MDMA and control drugs, were dissolved in physiological 0.9% saline and administered at a constant volume of 1 ml/100 g body weight.

Biological Data

Example 2: Behaviour Experiments

Social Interaction Testing

A social interaction test that has been used to test the effects of MDMA, specifically to test prosocial effects of MDMA, is described in Morley and McGregnor Eur J Pharmacol. 2000; 408:41-9, and is used to test the exemplary and comparative compositions of the application.

In order to familiarize subjects (mice) with the testing procedure and screen out aggressive subjects, the social interaction test is performed twice. During the first session, subjects receive injections of exemplary compositions of the application, comparative compositions or saline, and are isolated in clean cages for 30 minutes. Each subject is then paired with an unfamiliar weight-matched conspecific from the same treatment group in a 30×18 cm clear Plexiglas testing chamber for 10 minutes. An experimenter is present during the first test day to separate aggressive subjects. Any removed subjects are replaced with new naïve subjects so that each treatment condition has an equal number of non-aggressive subjects.

The second test session is performed 48 hours later using the same pairs, treatments, and procedure except that an experimenter is not present in the room during testing. While in the testing arena, subjects are free to move around and interact, allowing a diverse range of observable behaviors. On the second test day, the social pairings are videotaped and the duration of social behavior is quantified using JWatcher or BORIS (Friard and Gamba, Methods Ecol Evol. 2016; 7 (11) 1325-1330) by an observer blind to the experimental conditions. The durations of 3 behaviors are scored: anogenital investigation (sniffing the conspecific's anogenital area), general investigation (non-anogenital sniffing, grooming, and following the conspecific), and adjacent lying (side-by-side contact or huddling). These behaviors are averaged for each pair and then summed to produce a total social interaction score, upon which statistical analysis is performed.

Locomotor Behaviour

Effects of exemplary compositions of the application and comparative compositions on locomotor activity is tested in 45×39×37 cm open field chambers with 16×16 photocells positioned 2.5 cm off the chamber. Mice are treated with the exemplary compositions of the application, comparative compositions or saline (n=13/group) immediately before being placed into the chambers for 1 hour. Testing is performed in a dark, enclosed space. Accumulative beam breaks of adjacent photocells are recorded as the measure of locomotor activity.

Fear Conditioning and Extinction

The effects of exemplary compositions of the application and comparative compositions on conditioned freezing are evaluated using an established protocol (Young et al., 2015, Transl Psychiatry. 5:1-8) previously used to test racemic MDMA. For consistency with this prior study, C57BL/6 mice are used in this experiment. Briefly, mice are exposed to cued fear conditioning on day 1, fear extinction training on day 3, and extinction testing on day 4. Cued fear conditioning consists of a single pairing of a conditioned stimulus (CS) tone (80 dB, 4.5 kHz, 30 s) and an unconditioned stimulus (US) foot shock (1 mA, 2 s). Extinction training is carried out 48 hours later in a new context from conditioning. (R)-MDMA, (S)-MDMA, or saline (n=6-7/group) were administered on day 3, 30 minutes before training. Extinction training consists of a sub-optimal regimen of 4 C(S)-tone re-exposures separated by 45 seconds. Extinction testing is performed 24 hours later to determine the lasting effect of treatment on conditioned freezing. Extinction testing is performed in the same context as training and followed the same procedure except that no treatments is administered. Throughout these experiments, percent freezing (the conditioned response) is estimated by scoring the presence or absence of non-respiratory movement every 5 seconds.

Example 3: Neurotoxicity Studies

Neurotoxic Dosing and Tissue Collection

In a modified dosing regimen from Itzhak et al., Psychopharmacol. 2003; 166:241-248, subjects receive a total of four injections of exemplary compositions of the application, comparative compositions or saline given twice, two hours apart on two consecutive days. Subject are isolated during treatment and returned to their home cages 2 hours after the second daily dose. Following treatment, subjects are divided into two groups. 48 hours after the final injection, subjects from group 1 are anesthetized and transcardially perfused with 4% formaldehyde. Their brains are post-fixed overnight and then immersed in 15% sucrose for 48 hours, frozen in chilled methyl butane, sectioned at 35 µm, and stored at −20° C. until analysis by immunohistochemistry. Subjects in group 2 are euthanized by cervical dislocation 14 days after the last injection. Their brains are removed and prefrontal cortex, striatum, and hippocampus are rapidly dissected and stored at −80° C. for subsequent analysis by high-performance liquid chromatography (HPLC) or Western blot.

Body Temperature Monitoring

The effect of exemplary compositions of the application and comparative compositions on body temperature, given twice at a two-hour intervals, is monitored using a rectal thermometer (n=5/group). Measurements are taken every 30 minutes at an ambient room temperature of 22±2° C. During monitoring, mice are separated to individual holding cages.

Discussion (R)-MDMA will be less neurotoxic than a comparative composition comprising racemic mixture of MDMA.

Exemplary composition of the application ALA001 will present a neurotoxicity profile which is better than a comparative composition comprising a racemic mixture of MDMA.

(R)-MDMA is less neurotoxic than exemplary composition of the application ALA001 but exemplary composition of the application ALA001 will have a subjective psychological experience more similar to comparative composition comprising a racemic mixture of MDMA.

Example 4: Studies in Rat Models

Studies in Rat Models of Autism Spectrum Disorder

Introduction

Autism spectrum disorder (ASD) is a complex neurodevelopmental disorder defined by two main clusters of behaviors. The first group of behaviors is defined by deficits in social communication and social interaction, while the second group of behaviors consists of repetitive and inflexible patterns of behaviors, interests, and thoughts. In 2016, the Autism and Developmental Disabilities Monitoring Network estimated ASD prevalence at 1 in 54 children, and stated that ASD was 4.3 times more prevalent among boys compared to girls. Over the last several decades, the reported incidence of ASD has increased in the US, but the etiology of ASD remains poorly understood. To better understand the neurological basis of ASD, rodent models of ASD have been developed for research. The BTBR T+Itpr3tf/J mouse (BTBR), originally bred for studies on insulin-resistance, diabetes-induced nephropathy and phenyloketonuria, was identified approximately a decade ago as displaying strong and consistent autism-relevant behaviors. Identification of novel drugs which increase sociability and decrease repetitive behaviors in the autism-like BTBR mouse and in the C57BL/6J (C57) background stock are therefore therapeutically useful in the context of ASD. The bald patch often seen on the dorsal flank of BTBR mouse is due to repetitive grooming and "barbering" behavior exhibited by all mice of this strain, congruent with high rates of self-directed behavior which are characteristic of human ASD. Accordingly, the ability to remain blinded to strain is difficult.

The studies described in Example 4 used male BTBR and C57 mice to evaluate the effects of racemic 3,4-methylenedioxymethamphetamine (MDMA) (e.g., comparative composition 1, MDMA)), its component S enantiomer (e.g comparative composition 3, (S)-MDMA)) and R enantiomer (e.g., exemplary composition 7, (R)-MDMA), and customized compositions comprising a non-racemic mixture of (R)-MDMA, or a salt and/or solvate thereof, and (S)-MDMA, or a salt and/or solvate thereof wherein (R)-MDMA or a salt and/or solvate thereof is present in the composition in a greater amount by enantiomeric equivalents, relative to (S)-MDMA, or a salt and/or solvate thereof (e.g., exemplary composition 2(i)) in an autism-relevant assay of social preference, as well as in studies of the safety and abuse liability of these drugs. FIG. 1 provides the two dimensional molecular structures of methamphetamine (left structure) and 3,4-methylenedioxymethamphetamine (MDMA, right structure). Pharmacologically, enantiomers can have very different biological effects, including quantitative differences in potency and effectiveness, as well as qualitative differences in mechanism of action or interoceptive effects. In the case of methamphetamine, the S(+)-enantiomer is an abused psychostimulant with potent and long lasting psychoactive effects, while the R(−)-enantiomer is more than 100-fold less potent at eliciting any of these effects. In the case of MDMA, both enantiomers are active, at similar doses, although they elicit effects which are different in kind from one another. Based on their similar chemical structures, methamphetamine was chosen as a positive control compound against which to compare the effects of MDMA in the social preference tests. Both compounds were expected to elicit locomotor stimulant effects at large doses, but methamphetamine was not expected to elicit any pro-social effects.

General Animal Handling

Adult male C57 and BTBR mice were shipped to the University of Arkansas for Medical Sciences from Charles River Laboratories and The Jackson Laboratory, respectively. Upon arrival, mice were housed 3 per cage, according to strain, with food and water available ad lib. Mice were allowed to acclimatize to the UAMS facilities for at least 48 hours before any experimental procedures were performed.

Drug Administration:

All drugs were dissolved in physiological 0.9% saline and administered at a constant volume of 1 ml/100 g body weight. Because all drugs utilized in these studies were synthesized as hydrochloride (HCl) salts, they were weighed as salts prior to the preparation of all solutions. All drugs at all concentrations are readily dissolved in an aqueous solution at normal pH. Injections of all drugs were administered intraperitoneally (IP) to mimic pharmacokinetic parameters typical of oral administration, without the Behaviour-impairing effects of gavage stress.

Social Preference Testing Methods

This assay was conducted in adult male C57 and BTBR mice (n=6 per group) in a dedicated conditioning room where ambient light, sound, and human contact were tightly controlled. Social preference chambers consist of two polycarbonate boxes (13.5 cm wide×22.5 cm tall×31.0 cm deep), floored with rough-textured black ABS plastic, and connected to one another by a 1.25" PVC T-junction. An infrared photobeam emitter/detector array is mounted at each intersection of the T-junction and each preference compartment, and as a mouse traversed the apparatus, it would break the photobeam upon entry to or exit from each preference compartment. Beam breaks started or stopped a counter on an interfaced computer, allowing automated collection of time spent in each compartment. At the end of each test, data were reported as time (in seconds) spent in each compartment, the number of entries into each compartment, and the average time spent in each compartment following an entry. Social preference tests were conducted in an iterative manner, with each test subject completing four distinct phases as described below. Between testing sessions, chambers were sanitized by wiping the insides with a disinfectant product provided by the UAMS Department of Laboratory Animal Medicine. At the end of the week (upon completion of all phases of the procedure), each apparatus was disassembled and all parts were sanitized. No food or water were available during social preference sessions, but were available in the home cage immediately afterwards.

Phase 1—Habituation

A single habituation session occurred prior to preference testing, where each compartment contained an identical empty wire mesh pencil cup (9.0 cm diameter×10.5 cm tall). During this session, mice were weighed, no injection was administered, and subjects were introduced into the T-junction and allowed to explore both preference compartments for 30 minutes. This habituation session was conducted as a procedural control to allow animals to become accustomed to the apparatus and to screen out any animals with a strong initial bias for one of the two compartments. An a priori exclusion criterion was established such that any subjects spending more than 75% of the total time in one single preference compartment would be excluded from further study, but no subjects in these studies met this standard for exclusion. Habituation sessions always occurred on Mondays or Tuesdays to prevent any weekend testing.

Phase 2—Novelty Preference

A single novelty preference session occurred the day after the habituation test, where one compartment contained an empty wire mesh cup and the other compartment contained an identical wire mesh cup with a novel dummy mouse inside. The position of the dummy mouse (left or right compartment) was counterbalanced across subjects. Dummy mice were constructed from 2.5" lengths of white ¾" PVC pipe, with a zip tie attached to one end (to mimic a tail) and two red dots drawn on the other end (to mimic eyes.) During this session, mice were weighed, administered an injection, and returned to their home cage for a 30 min pretreatment period. Mice were then introduced into the T-junction and allowed to explore both preference compartments for 15 minutes. These tests were conducted as a procedural control to ensure that any observed drug effects were not simply due to enhancement of the innate novelty preference of mice. Novelty preference sessions always occurred on Tuesdays or Wednesdays to prevent any weekend testing.

Phase 3—Sociability Testing

A single sociability session occurred the day after the novelty preference test, where one compartment contained a wire mesh cup with a dummy mouse inside while the other compartment contained a male NIH Swiss stranger mouse inside the previously empty cup. The wire mesh cups allowed visual, olfactory, auditory, and limited tactile contact, but prevented aggressive behaviors which may otherwise have resulted in injury. The position of the dummy mouse (left or right compartment) remained the same for each subject as during the novelty test the day before, thereby counterbalancing the position of the stranger mouse across subjects. NIH Swiss stranger mice were similar in mass and appearance to the dummy PVC mice, and were housed separately from the experimental subjects (C57 and BTBR mice) in the colony facility. The first time the experimental subjects ever encountered the stranger mice was when they entered the compartment where they were contained. During this session, mice were weighed, administered the same injection as the day before, and returned to their home cage for a 30 min pretreatment period. Mice were then introduced into the T-junction and allowed to explore both preference compartments for 15 minutes. Sociability tests always occurred on Wednesdays or Thursdays to prevent any weekend testing.

Phase 4—Social Novelty Preference

A single social novelty preference session occurred the day after the sociability test, where one compartment contained a wire mesh cup with the same NIH Swiss mouse from the previous day inside (referred to now as the "familiar" mouse) while the other compartment contained a new male NIH Swiss stranger mouse inside the cup which previously contained the dummy mouse during the sociability test. The wire mesh cups allowed visual, olfactory, auditory, and limited tactile contact, but prevented aggressive behaviors which may otherwise have resulted in injury. The position of the now familiar NIH Swiss mouse (left or right compartment) remained the same for each subject as during the sociability test the day before, thereby counterbalancing the position of the new NIH Swiss stranger mouse across subjects. As before, the new NIH Swiss stranger mice were housed separately from the experimental subjects (C57 and BTBR mice) in the colony facility, and the first time the experimental subjects ever encountered them was when they entered the compartment where they were contained. During this session, mice were weighed, administered the same injection as the day before, and returned to their home cage for a 30 min pretreatment period. Mice were then introduced into the T-junction and allowed to explore both preference compartments for 15 minutes. Social novelty tests always occurred on Thursdays or Fridays to prevent any weekend testing.

Social Preference Testing Results

Drug Effect on Locomotor Activity

Quantification of total entries into the preference compartments provided a proxy measurement for locomotor stimulant effects of the various doses of the various test drugs. This established a limit to the drug doses that can be tested in the social preference procedure, as induction of locomotor stimulant effects confounds preference assessments (because mice stop attending to the social stimuli in each compartment and instead spend their time engaged in locomotor behavior.) Motor activity varied across the distinct phases of social preference testing, in part because the habituation session is twice as long (30 minutes) as the novelty, sociability, and social novelty tests (15 minutes each), but also because mice emitted high levels of exploratory behavior in novel environments. Thus, as familiarity with the test apparatus increased over successive exposures to the chambers, the number of entries decreased.

Figure 2:
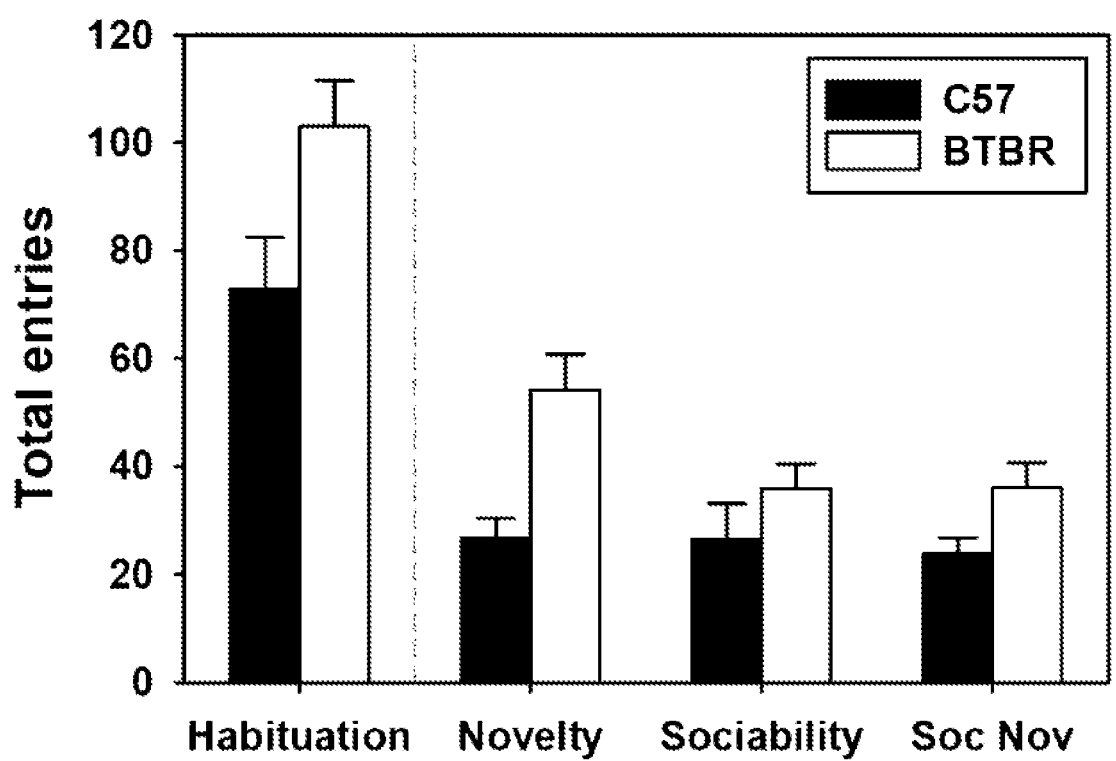
FIG. 2 is a graph showing total entries into the testing compartments during each phase of the social preference procedure in C57 (filled black bars) and BTBR (open white bars) mice administered saline injections prior to the novelty, sociability and social novelty (Soc Nov) tests.

FIG. 2 illustrates this decreasing trend in motor activity in C57 (filled black bars) and BTBR (open white bars) in the absence of any drug injections. Baseline differences in locomotor activity were also observed between the C57 and BTBR mice in the absence of drug injection, such that BTBR subjects always exhibited more entries during every phase of the social preference procedure.

Because baseline activity for C57 and BTBR mice did not change from the sociability to the social novelty test (the final testing phase, when mice are at maximum familiarity with the apparatus), the focus was on drug effects during this phase to determine locomotor stimulant effects of the various treatment drugs. (Note that entries were collected for every test, but drug effects on entries during earlier phases may be less reliable due to the confounding influence of changing familiarity with the apparatus across phases.)

Figure 3:
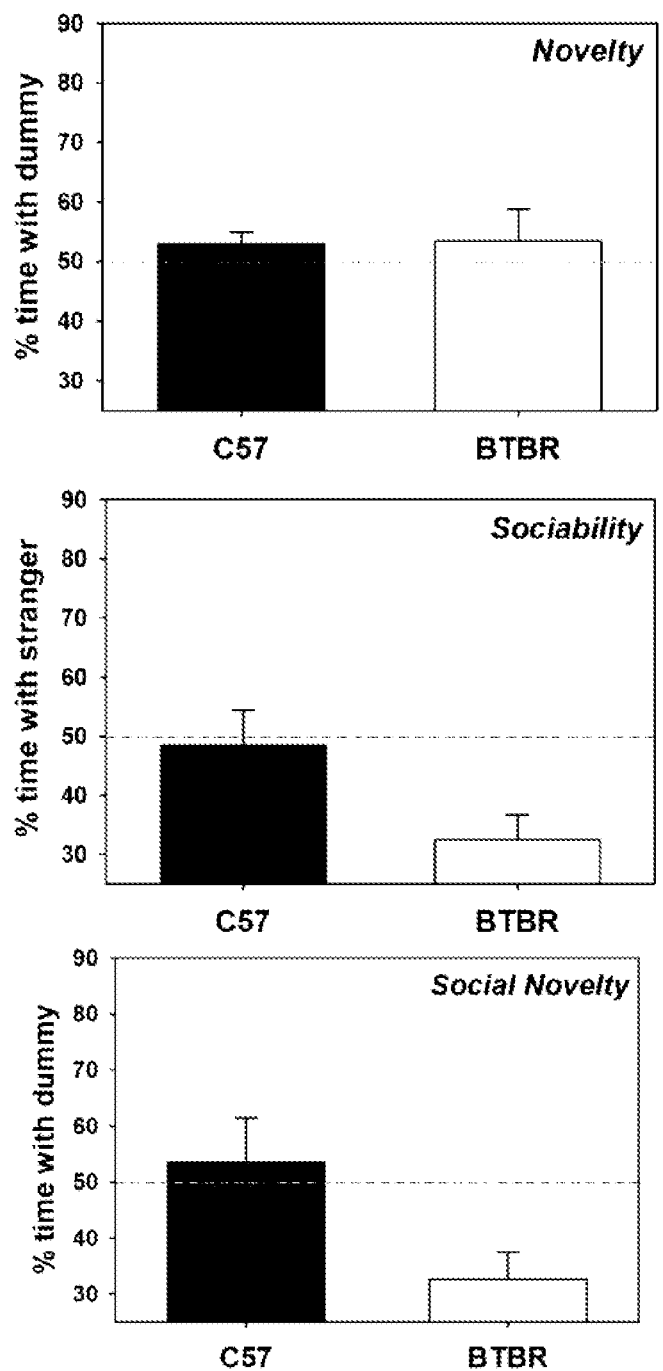
FIG. 3 are graphs showing baseline strain differences in preference during each phase of the social preference procedure in C57 (filled black bars) and BTBR (open bars) mice administered saline injections prior to testing. Bars represent group means, and error bars represent standard error mean (SEM). Note that both strains exhibit a comparable indifference during the novelty preference control test (top graph), but consistent with their autism-like phenotype, BTBR mice show social avoidance in the sociability (middle graph) and social novelty (bottom graph) phases.

In C57 mice (see FIG. 3, black bars), approximately 20 entries were observed following the administration of saline.

Figure 4:
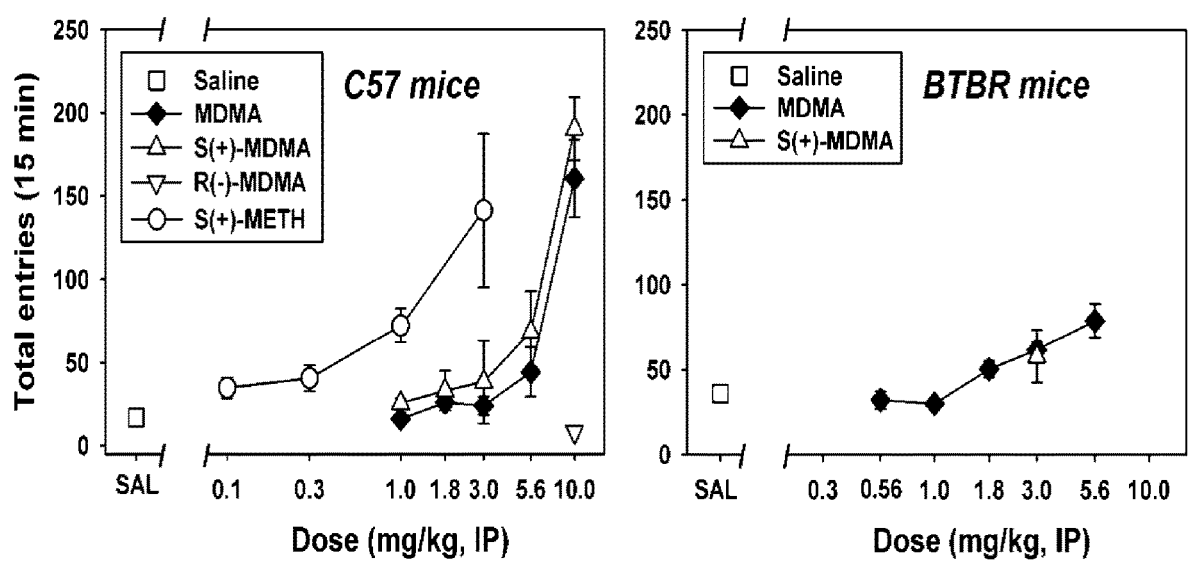
FIG. 4 are graphs showing the effects of saline (open square) or various doses of methamphetamine (circles), racemic MDMA (comparative composition 1, filled black diamonds), S(+)-MDMA ((comparative composition 3, upward triangles) or R(−)-MDMA (exemplary composition 7, downward triangle) on compartment entries during the social novelty test in C57 mice (left graph) and in BTBR mice (right graph). Dose is expressed in mg/kg and presented on a log scale.

Injection of methamphetamine (positive control), racemic MDMA (e.g, comparative composition 1) and S(+)-MDMA (e.g., comparative composition 3) dose-dependently increased entries to over 150, indicating locomotor stimulant effects which confound the assessment of social preference following 3.0 mg/kg methamphetamine, 10.0 mg/kg racemic MDMA (e.g. comparative composition 1) and 10.0 mg/kg S(+)-MDMA (e.g. comparative composition 3) (see FIG. 4). In contrast, administration of 10.0 mg/kg R(−)-MDMA (e.g. exemplary composition 7) did not increase compartment entries.

However, in BTBR mice (see FIG. 4, right pane open bars), approximately 40 entries were observed following administration of saline, consistent with their greater baseline levels of locomotor activity previously described in FIG. 2.

Injection of racemic MDMA (e.g., comparative composition 1) dose-dependently increased entries to close to 100 at 5.6 mg/kg, suggesting a more potent locomotor stimulant effect in BTBR mice than in C57s. A single dose of S(+)-MDMA (e.g comparative composition 3) was tested, and similar to the C57 mice, 3.0 mg/kg S(+)-MDMA (e.g. comparative composition 3) elicited roughly equivalent entries to 3.0 mg/kg racemic MDMA (e.g comparative composition 1). Because no dose of racemic MDMA (e.g comparative composition 1) or S(+)-MDMA (e.g comparative composition 3) increased entries to more than 100, all tested doses are presented in the social preference results described below.

Drug Effects on Novelty Preference

Figure 5:
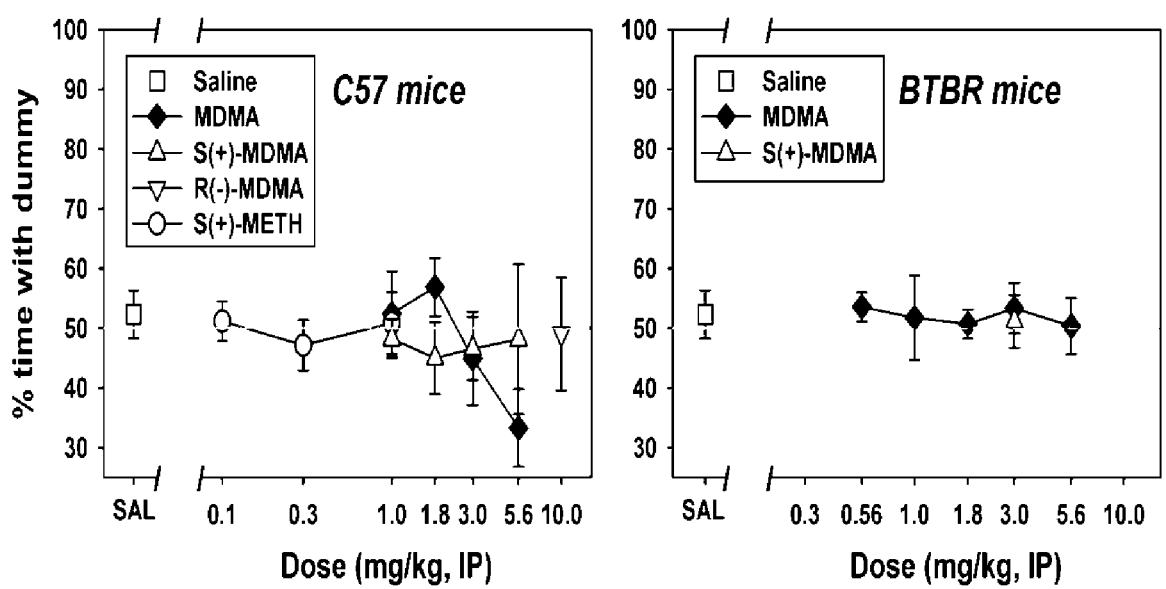
FIG. 5 are graphs showing effects of saline (open square) or various doses of methamphetamine (circles), racemic MDMA (comparative composition 1, filled black diamonds), S(+)-MDMA (comparative composition 3, upward triangles) or R(−)-MDMA (exemplary composition 7, downward triangle) on time spent with the dummy mouse during the novelty preference test in C57 mice (left graph) and in BTBR mice (right graph). Symbols represent group means, and error bars represent SEM unless the SEM is smaller than the size of the symbol. The dashed line indicates indifference for the compartment containing the dummy versus the compartment containing the empty cup. Dose is expressed in mg/kg and presented on a log scale. Note that C57s and BTBRs receiving saline display essentially identical behavior in this test, exhibiting a small preference for the novel dummy mouse.

C57 mice (see FIG. 5, left graph) exhibited no strong preference for the dummy mouse over the empty cup, as approximately equal amounts of time was spent in each compartment following administration of saline. Injection of methamphetamine, S(+)-MDMA (e.g comparative composition 3) or R(−)-MDMA (e.g. exemplary composition 7) had no systematic effects on novelty preference, but administration of racemic MDMA (e.g comparative composition 1) elicited avoidance of the dummy mouse at the 5.6 mg/kg dose.

BTBR mice (see FIG. 5, right graph) also did not display a strong preference for the dummy mouse over the empty cup, as like the C57s, approximately equal amounts of time were spent in each compartment following administration of saline.

No dose of racemic MDMA (e.g comparative composition 1) or S(+)-MDMA (e.g comparative composition 3) elicited any effects on novelty preference. Because none of the test drugs increased novelty preference, any enhancement of social preference in subsequent tests is unlikely to be confounded by novelty-related effects, such as changes in the motivational properties of novel objects, which might otherwise be confused for pro-social effects.

Drug Effects on Sociability

Figure 6:
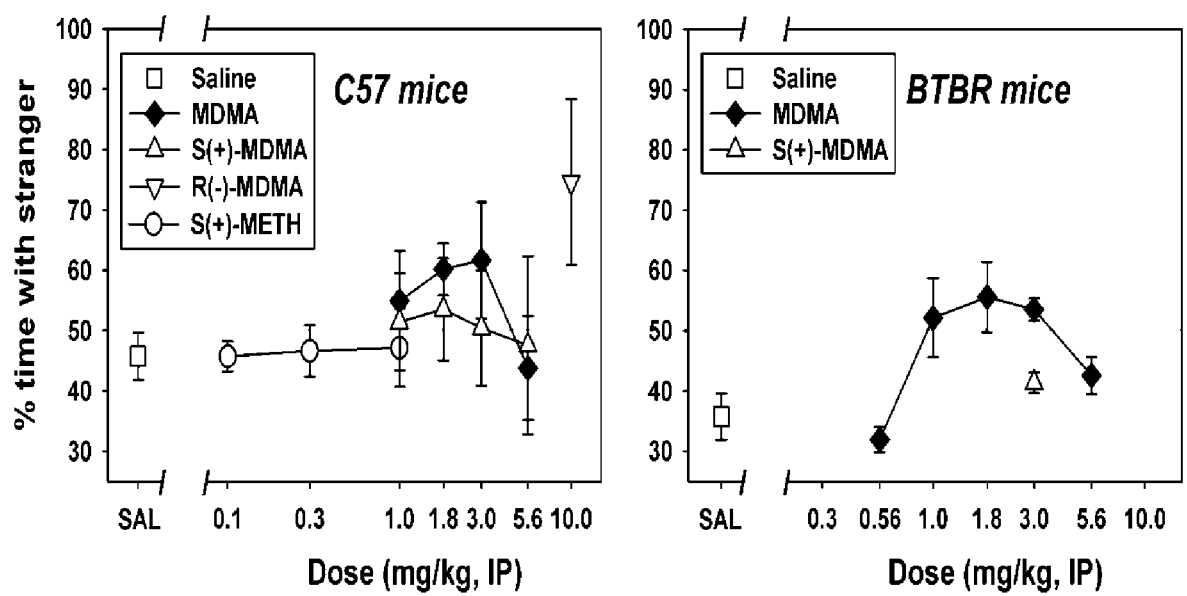
FIG. 6 are graphs showing effects of saline (open square) or various doses of methamphetamine (circles), racemic MDMA (comparative composition 1, filled black diamonds), S(+)-MDMA (comparative composition 3, upward triangles) or R(−)-MDMA (exemplary composition 7, downward triangle) on time spent with the stranger mouse during the novelty preference test in C57 mice (left graph) and in BTBR mice (right graph). Symbols represent group means, and error bars represent SEM unless the SEM is smaller than the size of the symbol. The dashed line indicates indifference for the compartment containing the dummy versus the compartment containing the stranger mouse. Dose is expressed in mg/kg and presented on a log scale. Note that BTBRs receiving saline display the expected autism-like social avoidance in this test, exhibiting avoidance of the stranger mouse.

C57 mice exhibited a slight avoidance of the stranger mouse, as slightly less time was spent in the compartment containing the stranger mouse than in the compartment containing the dummy following administration of saline (see FIG. 6, left graph).

Injection of methamphetamine or S(+)-MDMA (e.g comparative composition 3) had no systematic effects on sociability, but administration of racemic MDMA elicited a dose-dependent increase in time spent with the stranger mouse, producing a moderate preference for the stranger over the dummy at the 3.0 mg/kg dose. The largest effect on sociability was elicited by administration of 10.0 mg/kg R(−)-MDMA (e.g exemplary composition 7). Interestingly, these doses of racemic MDMA (e.g comparative composition 3) and R(−)-MDMA (e.g exemplary composition 7) which increased sociability had no effects on locomotor activity (see FIG. 4) or novelty preference (see FIG. 5).

In BTBR mice (see FIG. 3, right bar), the expected autism-like social decrement was observed following saline administration, where mice exhibited a strong avoidance of the stranger mouse. Administration of racemic MDMA elicited a similar biphasic effect on sociability as observed in the C57s, with the smallest tested dose having no effect, intermediate doses increasing preference for the stranger mouse, but these pro-social effects were not observed after injection of the largest dose. Also similar to C57 mice, the single dose of S(+)-MDMA (e.g comparative composition 3) tested did not alter sociability in the BTBRs (See FIG. 6). In contrast to the dissociation of locomotor effects from pro-social effects observed in the C57 mice, BTBR mice only exhibited increased sociability following administration of racemic MDMA (e.g comparative composition 1) doses which increased motor activity (as previously seen).

Drug Effects on Social Novelty Preference

Figure 7:
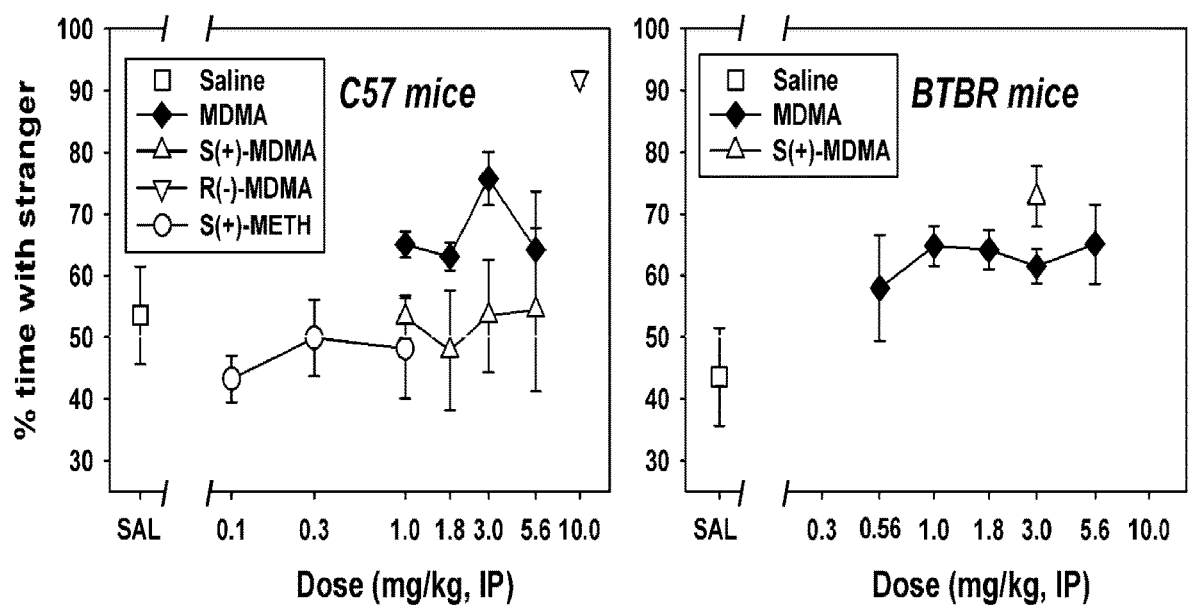
FIG. 7 are graphs showing effects of saline (open square) or various doses of methamphetamine (circles), racemic MDMA (comparative composition 1, filled black diamonds), S(+)-MDMA (comparative composition 3, upward triangles) or R(−)-MDMA (exemplary composition 7, downward triangle) on time spent with the stranger mouse during the social novelty preference test in C57 mice (left graph) and in BTBR mice (right graph). Symbols represent group means, and error bars represent SEM unless the SEM is smaller than the size of the symbol. The dashed line indicates indifference for the compartment containing the now familiar mouse versus the compartment containing the new stranger mouse. Dose is expressed in mg/kg and presented on a log scale. Note that BTBRs receiving saline display the expected autism-like social avoidance in this test, exhibiting avoidance of the stranger mouse.

C57 mice exhibited a small preference for the new stranger mouse, as slightly more time was spent in the compartment containing the new stranger mouse than in the compartment containing the now familiar mouse following administration of saline (see FIG. 7, left graph).

Injection of methamphetamine or S(+)-MDMA (e.g comparative composition 3) had no systematic effects on social novelty preference, but administration of racemic MDMA (e.g comparative composition 1) elicited a dose-dependent increase in time spent with the stranger mouse, producing a strong preference for the stranger over the now familiar mouse at the 3.0 mg/kg dose.

As observed in the sociability test, the largest effect on social novelty preference was elicited by administration of 10.0 mg/kg R(−)-MDMA (e.g exemplary composition 7). Interestingly, these doses of racemic MDMA (e.g comparative composition 1 and R(−)-MDMA (e.g exemplary composition 7) which strongly increased social novelty preference had no effects on locomotor activity (see FIG. 4) or novelty preference (see FIG. 5).

In BTBR mice (see FIG. 7, right graph), the expected autism-like social decrement was observed following saline administration, where mice exhibited a small avoidance of the stranger mouse. Administration of all doses of racemic MDMA (e.g comparative composition 1) elicited similar effects on social novelty preference, with BTBR mice treated with any dose of racemic MDMA (e.g comparative composition 1) exhibiting preferences for the stranger mouse. Distinct to the lack of pro-social effects of S(+)-MDMA (e.g comparative composition 3) observed in C57 mice, the single dose of S(+)-MDMA (e.g comparative composition 3) tested in BTBR mice elicited a strong preference for the stranger mouse. Again in contrast to the dissociation of locomotor effects from pro-social effects observed in the C57 mice, and with the exception of the smallest racemic MDMA (e.g comparative composition 1) dose tested, BTBR mice exhibited increased social novelty preference following administration of racemic MDMA (e.g comparative composition 1) and S(+)-MDMA (e.g comparative composition 3) at doses which increased motor activity Overview of Drug Effect in C57 Mice Racemic MDMA (e.g comparative composition 1), S-(+)-MDMA (e.g comparative composition 3) stimulated the motor activity in C57 mice in a dose-dependent manner, with over 100 entries documented at 10 mg/kg, intraperitoneal administration (see 8, top left graph). In contrast, even at 10 mg/kg R-(−) MDMA (e.g exemplary composition 7) has no stimulant effect on the motor activity of C57. Exemplary composition 2(i) comprising 80% (R)-MDMA and 20% (S)-MDMA dosed at higher doses has some stimulant effect, but it is substantially lower than that observed for S-MDMA (e.g comparative composition 3) and racemic MDMA (e.g comparative composition 1).

Figure 8:
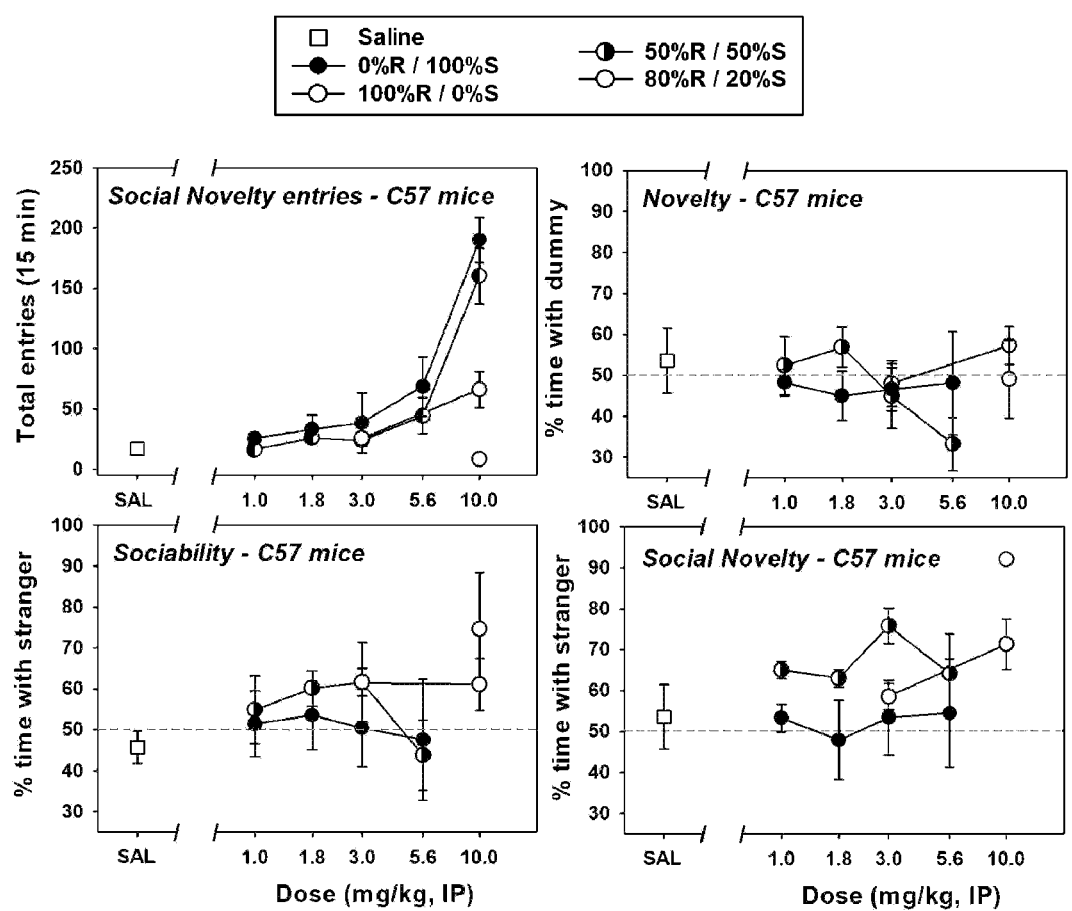
FIG. 8 are graphs showing the effects of saline (square), racemic MDMA (comparative composition 1, black and white circles), S(+)-MDMA (comparative composition 3, black circles), R(−)-MDMA (exemplary composition 7, white circles) and exemplary composition 2(i) (80% R(−)-MDMA and 20% S(+)-MDMA, gray circle) on compartment entries (top left graph), novelty preference (top right graph), sociability (bottom left graph) and social novelty preference (bottom right graph) in C57 mice at doses up to 10 mg/kg.

C57 mice, upon administration of 10 mg/kg R-MDMA (e.g exemplary composition 7) exhibited a strong preference for the new stranger mouse, as more time, was spent in the compartment containing the new stranger mouse than in the compartment containing the now familiar mouse (bottom right graph, FIG. 8). In contrast, even after administration of 3.0 mg/kg and 5.6 mg/kg of S-MDMA (e.g comparative composition 3), C57 does not elicit any substantial preference for the stranger mouse compared to the now familiar mouse (bottom right graph, FIG. 8). Racemic MDMA (e.g comparative composition 1) demonstrated a bi-phasic dose-response preference for stranger mouse over familiar mouse, with maximum preference documented at 3 mg/kg dose. Exemplary composition 2(i) dosed at 10 mg/kg elicited a strong preference for the stranger mouse without overly stimulating the mouse, as is seen with Racemic MDMA (e.g comparative composition 1).

Drug Effect in C57 vs BTBR Mice

Figure 9:
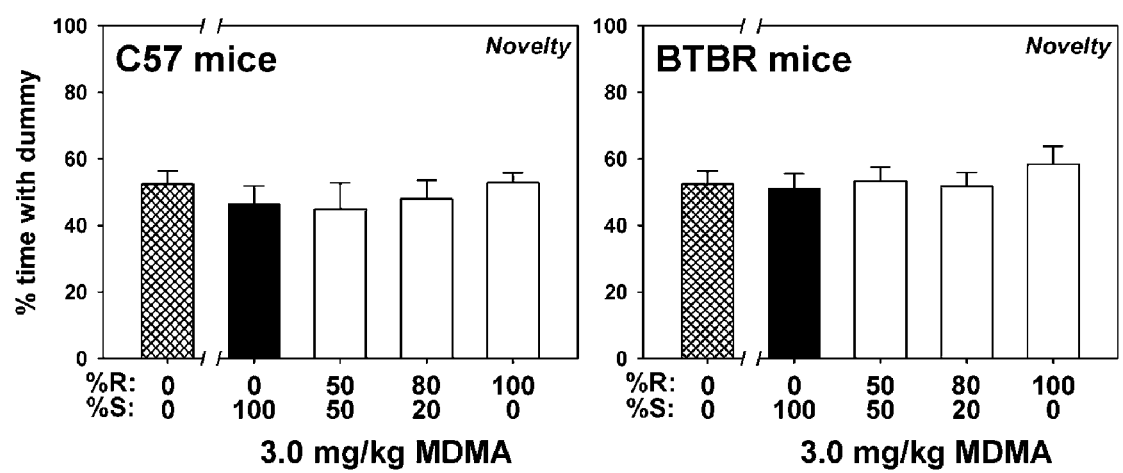
FIG. 9 are graphs showing the effect of saline (hatched bar) and 3.0 mg/kg of MDMA at specified enantiomer ratios: saline (hatched bar, first bar from left), 100% S(+)-MDMA (comparative composition 3, second bar from left), racemic MDMA (50% R(−)-MDMA and 50% S(+)-MDMA, comparative composition 1, third bar from left), exemplary composition 2(i) (80% R(−)-MDMA and 20% S(+)-MDMA, fourth bar from left), and 100% R(−)-MDMA (exemplary composition 7, fifth bar from left), on Novelty preference in C57 (left graph) vs BTBR (right graph) mice. Thus, the total dose of drug remains the same (3.0 mg/kg), but the enantiomeric composition of the administered dose differs between groups

When studying the impact of the drugs on the novelty preference (preference for a novel dummy mouse over an empty cup), no systemic effects were observed in either strain, based on data (see FIG. 9). This was a control experiment to ensure that observed drug effects in subsequent social preference tests are truly related to the social behaviour as opposed to changes in salience of novel stimuli.

Figure 10:
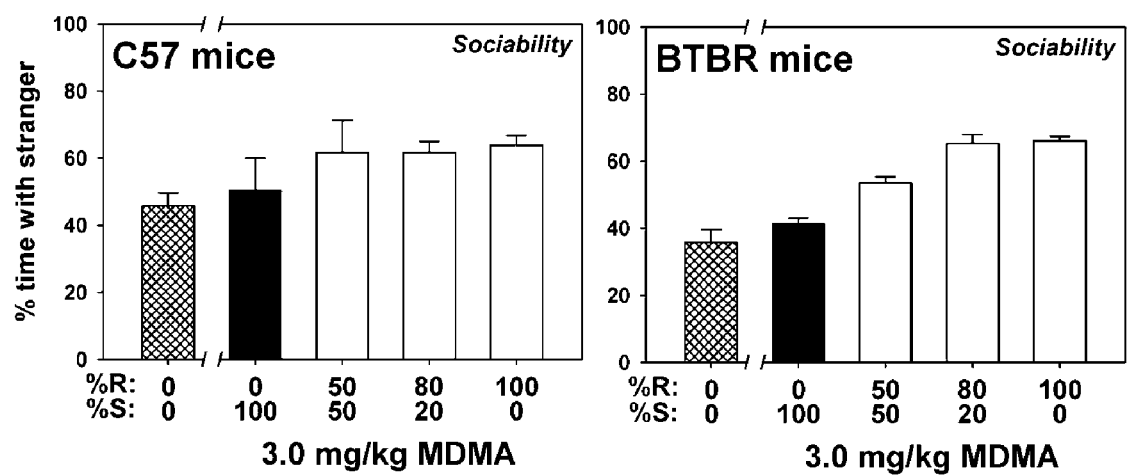
FIG. 10 shows the effect of saline and MDMA (3.0 mg/kg) at specified enantiomer ratios: saline (hatched bar, first bar from left), 100% S(+)-MDMA (comparative composition 3, second bar from left), racemic MDMA (50% R(−)-MDMA and 50% S(+)-MDMA, comparative composition 1, third bar from left), exemplary composition 2(i) (80% R(−)-MDMA and 20% S(+)-MDMA, fourth bar from left), and 100% R(−)-MDMA (exemplary composition 7, fifth bar from left), on sociability in C57 (left graph) and BTBR (right graph) mice. Darker bars indicate more S-MDMA, lighter bars indicate more R-MDMA. The total dose of drug remains the same (3.0 mg/kg), but the enantiomeric composition of the administered dose differs between groups FIG. 11 are graphs showing the effect of saline and 3.0 mg/kg MDMA at specified enantiomer ratios: saline (hatched bar, first bar from left), 100% S(+)-MDMA (comparative composition 3, second bar from left), racemic MDMA (50% R(−)-MDMA and 50% S(+)-MDMA comparative composition 1, third bar from left), exemplary composition 2(i) (80% R(−)-MDMA and 20% S(+)-MDMA, fourth bar from left), and 100% R(−)-MDMA (exemplary composition 7, fifth bar from left), on social novelty preference test (preference for a new stranger mouse over a familiar mouse) in c57 (left graph) and BTBR mice (right graph). Darker bars indicate more S-MDMA and lighter bars indicate more R-MDMA, Thus, the total dose of drug remains the same (3.0 mg/kg), but the enantiomeric composition of the administered dose differs between groups FIG. 12 are graphs showing the effects of saline (hatched bar) and 3.0 mg/kg MDMA at specified enantiomer ratios: saline (hatched bar, first bar from left), 100% S(+)-MDMA (comparative composition 3, second bar from left), racemic MDMA (50% R(−)-MDMA and 50% S(+)-MDMA, comparative composition 1, third bar from left), exemplary composition 2(i) (80% R(−)-MDMA and 20% S(+)-MDMA, fourth bar from left), and 100% R(−)-MDMA (exemplary composition 7, fifth bar from left), at specified enantiomer ratios on the number of entries into the two distinct compartments (a proxy measure for exploratory behavior/locomotor activity) assessed during the social novelty preference test in C57 (left graph) and BTBR mice (Right graph).

For C57 mice, racemic (50/50) MDMA (e.g comparative composition 3), exemplary composition 2(i) comprising 80% (R)-MDMA and 20% (S)-MDMA d, and pure R-MDMA (e.g, exemplary composition 7) elicit significant effects on sociability at the 3.0 mg/kg dose, but the effects of pure S-MDMA (e.g comparative composition 3), are not different from saline (see FIG. 10). For the BTBR mice, there appears to be a "dose-dependent" effect such that the more R-MDMA is present in the mixture, the bigger the effect (although there may be a plateau as exemplary composition 2(i)—is identical to the pure R-MDMA (e.g, exemplary composition 7.) Thus exemplary composition 2(i)— elicits a stronger sociability response than Racemic MDMA (e.g comparative composition 1) and S-MDMA (e.g comparative composition 3).

Figure 11:
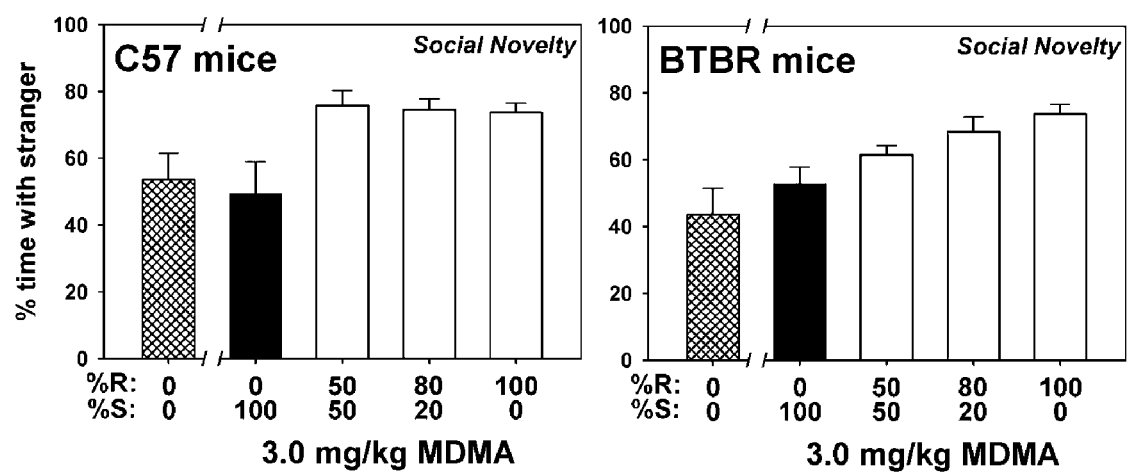
Figure 12:
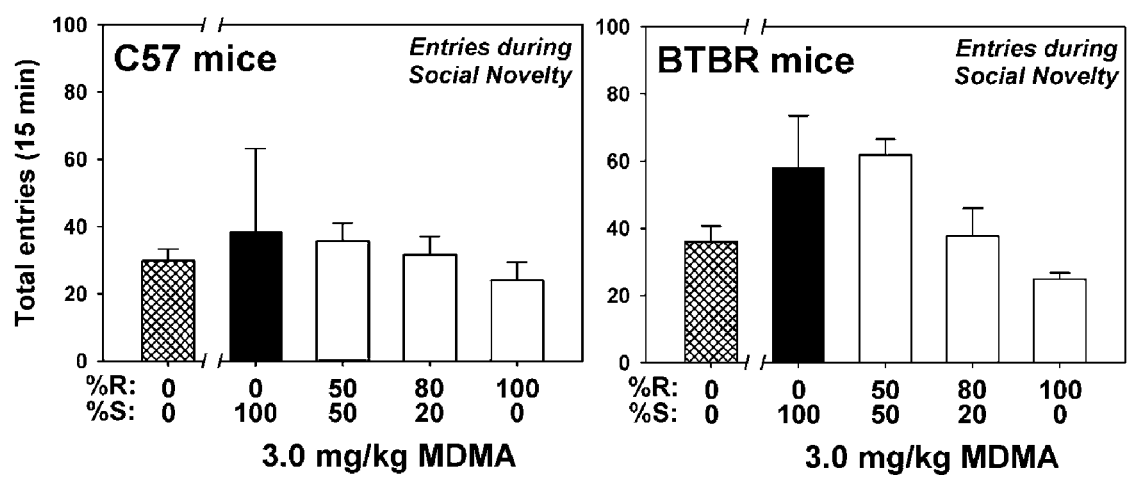

For C57 mice, racemic (50/50) MDMA (e.g comparative composition 1), exemplary composition 2(i) and pure R-MDMA (e.g exemplary composition 7) elicit significant effects on sociability at the 3.0 mg/kg dose, but the effects of pure S-MDMA (e.g comparative composition 3), are not different from saline (See FIG. 11). For the BTBR mice, there again appears to be a "dose-dependent" effect such that the more R-MDMA is present in the mixture, the bigger the effect with exemplary composition 2(i) performing nearly similar as R-MDMA (e.g exemplary composition 7). It is important to take this into consideration along with the locomotor stimulant effect captured in FIG. 12. For C57 mice, none of the MDMA formulations significantly altered entries. For the BTBR mice, pure S-MDMA (e.g comparative composition 3), and the racemic mixture (e.g comparative composition 1) increased the number of entries observed at this dose, but no stimulation of motor activity was observed with exemplary composition 2(i) comprising 80% (R)-MDMA and 20% (S)-MDMA, while pure R-MDMA (e.g exemplary composition 7) reduced entries at this dose.

Summary:

In summary, it has been demonstrated that S-MDMA (e.g comparative composition 3) and Racemic MDMA (e.g comparative composition 3) have a dose-response stimulant effect on the C57 mice (representative of the general population) and BTBR mice (representative of the autistic population), while R-MDMA (e.g exemplary composition 7) at higher doses (3 mg/kg) suppresses the locomotor activity in BTBR mice. Exemplary composition 2(i) comprising 80% (R)-MDMA and 20% (S)-MDMA does not influence the locomotor activity in BTBR and C57 mice.

The influence of exemplary composition 2(i) on pro-social behaviour is well captured through the social novelty preference test, where at 3 mg/kg administration (i.p) in BTBR and C57 mice, the mice under the influence of the drug have a strong preference to interact with and spend time with a stranger over mouse over a familiar mouse. The time spent with the stranger is much more than that observed under the influence of Racemic MDMA (e.g comparative composition 1) and S-MDMA (e.g comparative composition 3).

B. Radiotelemetry of Core Temperature and Motor Activity Testing Methods

Radiotelemetry of Core Temperature and Motor Activity Testing Methods

Monoamine-mimetic agents can affect temperature control, particularly amphetamine derivatives such as MDMA, which has perhaps been most widely studied (Freedman et al., Psychopharmacology, (2005) 183, 248-256; Kendrick et al., (1977) Annals of Internal Medicine, 86, 381-387; Parrott, A C (2012) Drug and Alcohol Dependence, 121, 1-9; Docherty & Green, (2010), British Journal of Pharmacology, 160, 1029-1044). Thus, the purpose of this study was to study the impact of the drug(s) of interest on the core body temperature of C57 and BTBR mice. Building on the social preference demonstrated by exemplary composition 2(i) the impact of the such non-racemic compositions of the application and (R)-MDMA (exemplary composition 7) was included in this study.

The radiotelemetry assay was conducted in adult male C57 and BTBR mice (n=6 per group) in a dedicated testing room where ambient light, sound, and human contact were tightly controlled.

Prior to surgical implantation of radiotelemetry probes, mice received 3 mg/kg meloxicam (IP), and anesthesia was induced with 4% inhaled isoflurane and maintained with 1-3% isoflurane (as needed) throughout the procedure at a flow rate of 1.5 litres/minute. The abdominal area of each animal was treated with depilatory cream, then sanitized with 3 alternating scrubs with iodine and alcohol. A rostral-caudal cut approximately 1.5 cm in length was made with sterile skin scissors, providing access to the intraperitoneal cavity. A cylindrical glass-encapsulated radiotelemetry probe (model ER-4000 E-Mitter, Mini Mitter, Bend, OR, USA) was then inserted. These probes measure 15.5 mm×6.5 mm and weigh approximately 1 gram. Incisions were closed (skin layer and muscle layer separately) using reverse cutting 5-0 Vicryl absorbable sutures for the muscle layer and 5-0 nylon suture material for the skin layer. Surgeries were carried out at least 7 days before initiation of experimental conditions, allowing time for incisions to heal and for animals to recover normal body weights. Following surgery, all implanted mice were individually housed in Plexiglas cages within the telemetry room for the duration of all experiments. Implanted transmitters produce activity- and temperature-modulated signals which are sent to a receiver (model ER-4000 Receiver, Mini Mitter Co., Inc.) underneath each cage. Following use, telemetry probes were removed from carcasses, wiped with alcohol swabs, and stored in the disinfectant solution until re-use.

At least 7 days after surgical implantation of radiotelemetry probes, mice in their individual home cages were placed atop a telemetry energizer/receiver, which powered probes and transmitted their data to an interfaced computer. Upon initiation of an experimental session, the computer collected two data updates from the probes at 5 min intervals: core temperature (in ° C.) on one channel, and locomotor counts (in arbitrary units, depending on the relative position of the probe atop the receiver) on the other. After at least 60 minutes of baseline data collection, mice were removed from their cages, injected with saline or a given dose of a specific drug, then returned to the home cage 24 hours of data collection.

Food and water were always freely available in the home cage. Mice were injected with ascending doses of a given drug, with at least 48 hours separating doses. Because there are few studies of drug effects in BTBR mice, the first drug dose tested occasionally elicited unexpectedly large locomotor effects in these animals. In these cases, smaller drug doses were tested next, after a washout period of at least one full day.

Effect of Saline Injection on Core Temperature and (Locomotor Activity) LMA in C57 and BTBR Mice [Establishment of Baseline and Characteristics of the Mice Species]

Figure 13:
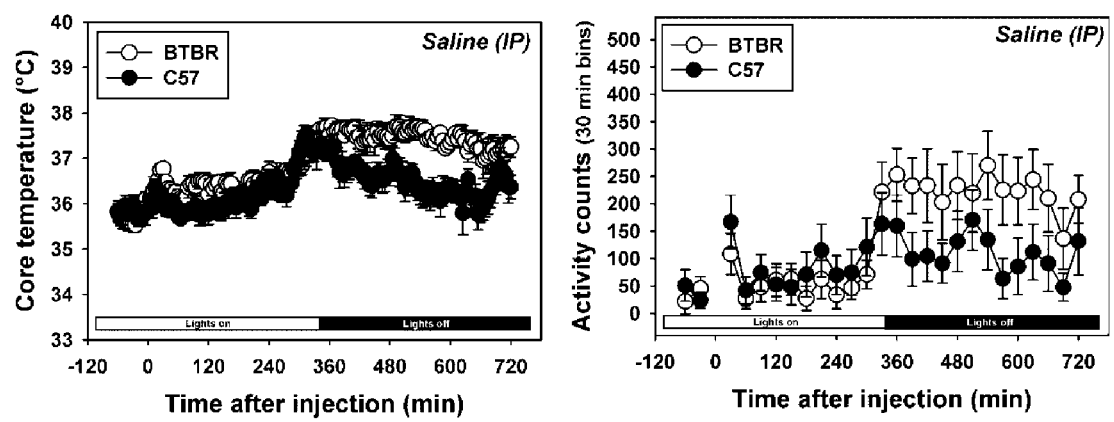
FIG. 13 are graphs showing the effect of saline injection on core temperature (left panel) and locomotor activity (right panel) in C57 (filled circles) and BTBR mice (filled circles). Symbols represent group means, and error bars represent SEM unless the SEM is smaller than the size of the symbol. The bar at the bottom of each panel indicates when room lights were on or off.

FIG. 13 shows the saline injection on core temperature (left panel) and locomotor activity (right panel) in C57 (filled circles) and BTBR mice (filled circles. Both strains display a transiently increased core temperature and higher activity levels for approximately 30 min following saline administration. The activity also follows the normal circadian pattern for both strains. More motor activity was recorded during the subjective dark phase, but interestingly, the BTBR mice exhibit more activity than the C57s, along with an elevated core temperature likely due to this higher activity.

Figure 14:
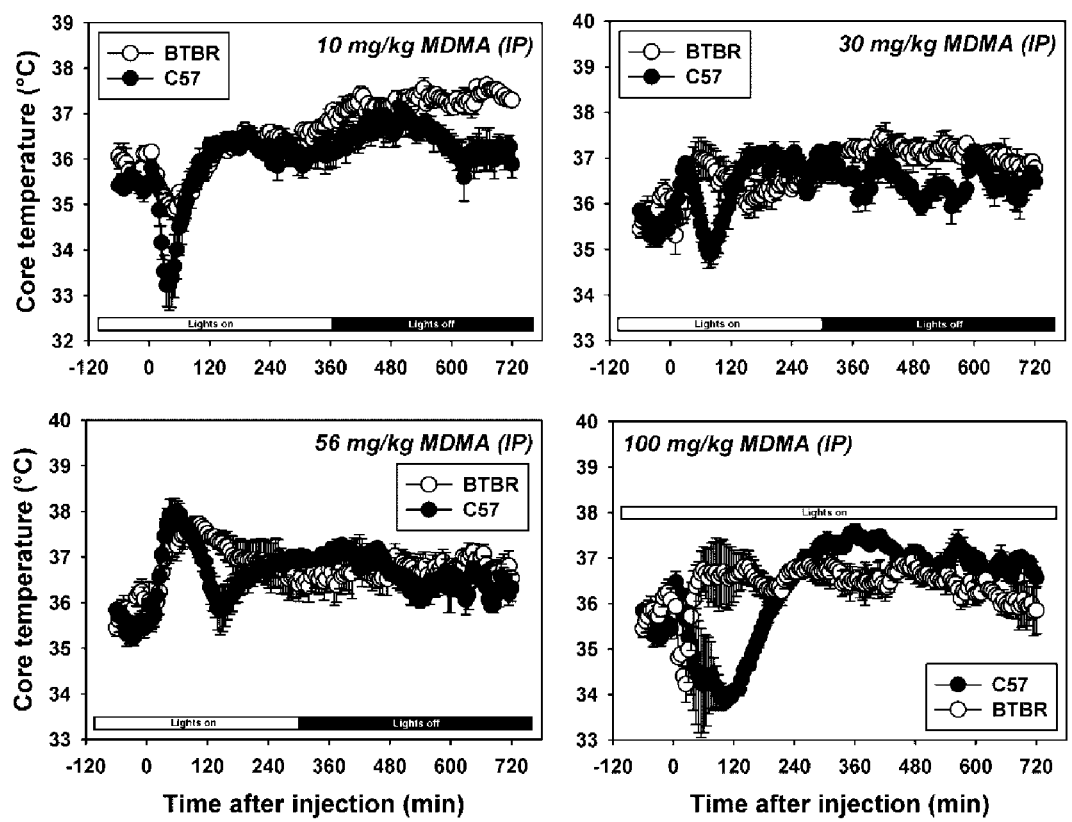
FIG. 14 shows the effect of various doses of racemic MDMA (e.g. comparative composition 1) on the core temperature in C57(filled circle) and BTBR mice (open circle). Symbols represent group means, and error bars represent SEM unless the SEM is smaller than the size of the symbol. The bar at the bottom of each panel indicates when room lights were on or off.

Effect of Increased Doses of Racemic MDMA Injection on the Core Temperature in C57 and BTBR Mice FIG. 14 shows the effect of various doses (10 mg/kg, 30 mg/kg, 56 mg/kg, 100 mg/kg) of racemic MDMA (e.g. comparative composition 1) on the core temperature in C57(filled circle) and BTBR mice (open circle). Because lethality was expected at the 100 mg/kg dose, injections, at this dose, were administered at the start of the workday and room lights, therefore, remained on for the duration of the data traces shown here.

At 10 mg/kg IP administration, Racemic MDMA (e.g. comparative composition 1) induced a drop in core temperature in both C57 and BTBR mice 30 mins-1 h after injection which subsequently stabilized. Increasing the doses saw a gradual increase in core temperature in both BTBR and C57 mice; with a nearly 2 degrees C. rise in temperature at 56 mg/kg.

Effect of Increased Doses of Racemic MDMA Injection on LMA in C57 and BTBR Mice

Figure 15:
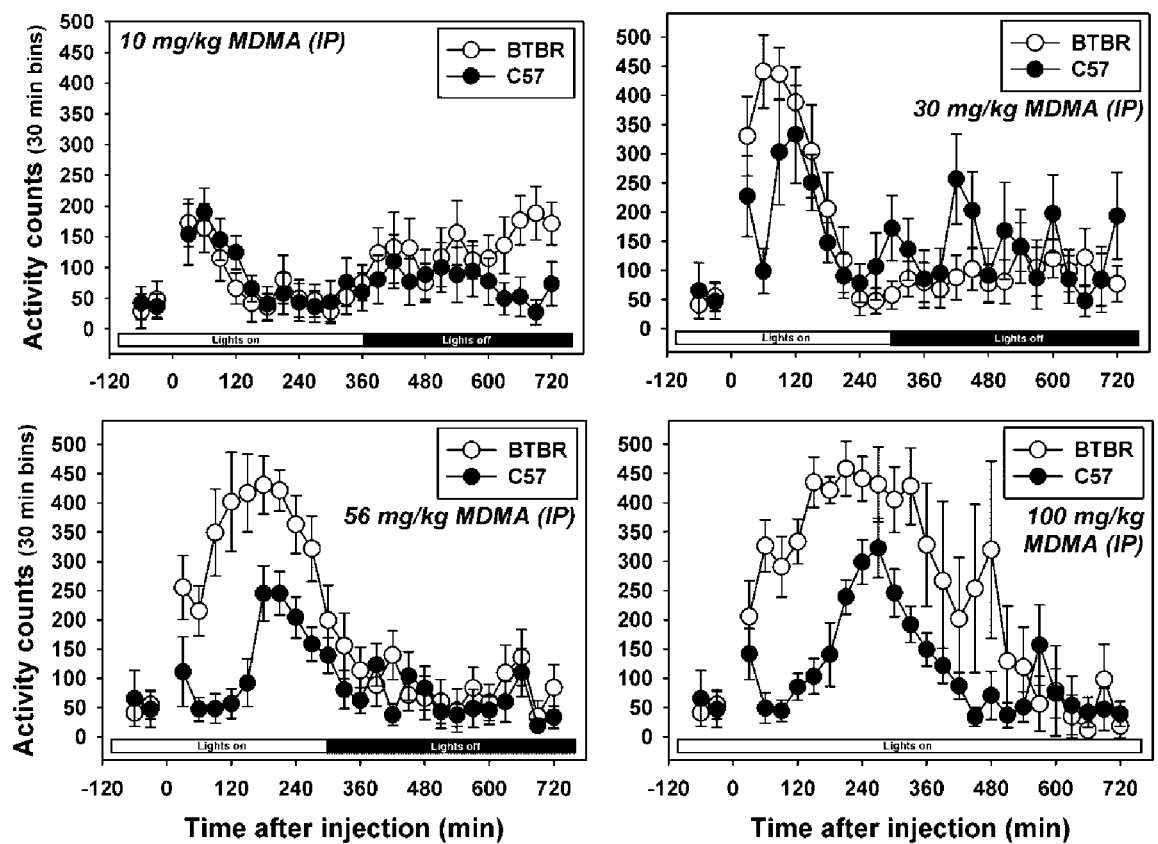
FIG. 15 shows the effects of various doses of racemic MDMA (50% R(−)-MDMA and 50% S(+)-MDMA, comparative composition 1) on locomotor activity in C57 (filled circles) and BTBR (open circles) mice. Symbols represent group means, and error bars represent SEM unless the SEM is smaller than the size of the symbol. The bar at the bottom of each panel indicates when room lights were on or off. Because lethality was expected at the 100 mg/kg dose, injections at this dose, were administered at the start of the workday and room lights, therefore, remained on for the duration of the data traces shown here.

FIG. 15 shows the effects of various doses of racemic MDMA (e.g. comparative composition 1) on locomotor activity in C57 (filled circles) and BTBR (open circles) mice. The pattern of locomotor activity (see 15) across the time course for the C57s administered 30, 56 and 100 mg/kg is consistent with motor stereotypy: an initial increase in activity is observed, followed by suppression of locomotion, then a "late phase" increase in activity as MDMA is cleared and eliminated. No evidence of motor stereotypy in the BTBR was observed at any dose. The increased locomotor effect corresponds to the modulation in temperature as documented in 14 above.

Figure 16:
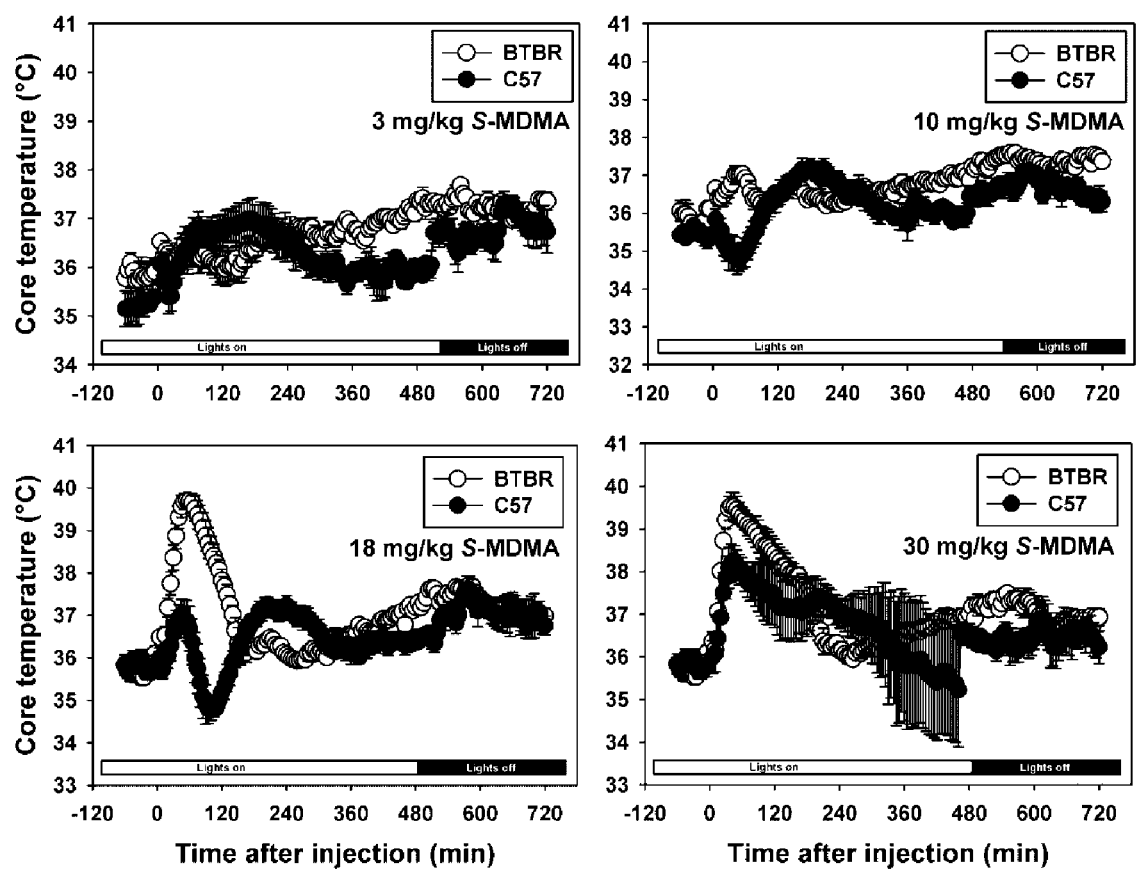
FIG. 16 shows the effects of various doses (3 mg/kg, 10 mg/kg, 18 mg/kg, 30 mg/kg) of S-MDMA (comparative composition 3) on core temperature in C57 (filled circles) and BTBR (open circles) mice. Symbols represent group means, and error bars represent SEM unless the SEM is smaller than the size of the symbol. The bar at the bottom of each panel indicates when room lights were on or off.

Effect of Increased Doses of S-MDMA Injection on Core Temperature in C57 and BTBR Mice FIG. 16 shows the effect of various doses of S-MDMA (e.g. comparative composition 3) on core temperature in C57 (filled circles) and BTBR (open circles) mice. Note that the large error bars in the C57 data trace from approximately 5-8 hrs after injection were due to one animal experiencing profound hypothermia before expiring. The abrupt "jump" in mean temperature is a consequence of this subject being removed from group average after death.

Like Racemic MDMA (e.g. comparative composition 1), S-MDMA (e.g. comparative composition 3) elicits a dose-dependent increase in temperature in both C57 and BTBR mice with the key distinction being that lower doses of S-MDMA elicit a stronger change in core temperature. The jump in core temperature at 18 mg/kg i.p administration of S-MDMA (e.g. comparative composition 3) (16) is greater than that observed by administration of 56 mg/kg i.p of Racemic MDMA (e.g. comparative composition 1) (14)

Effect of Increased Doses of S-MDMA Injection on LMA in C57 and BTBR Mice

Figure 17:
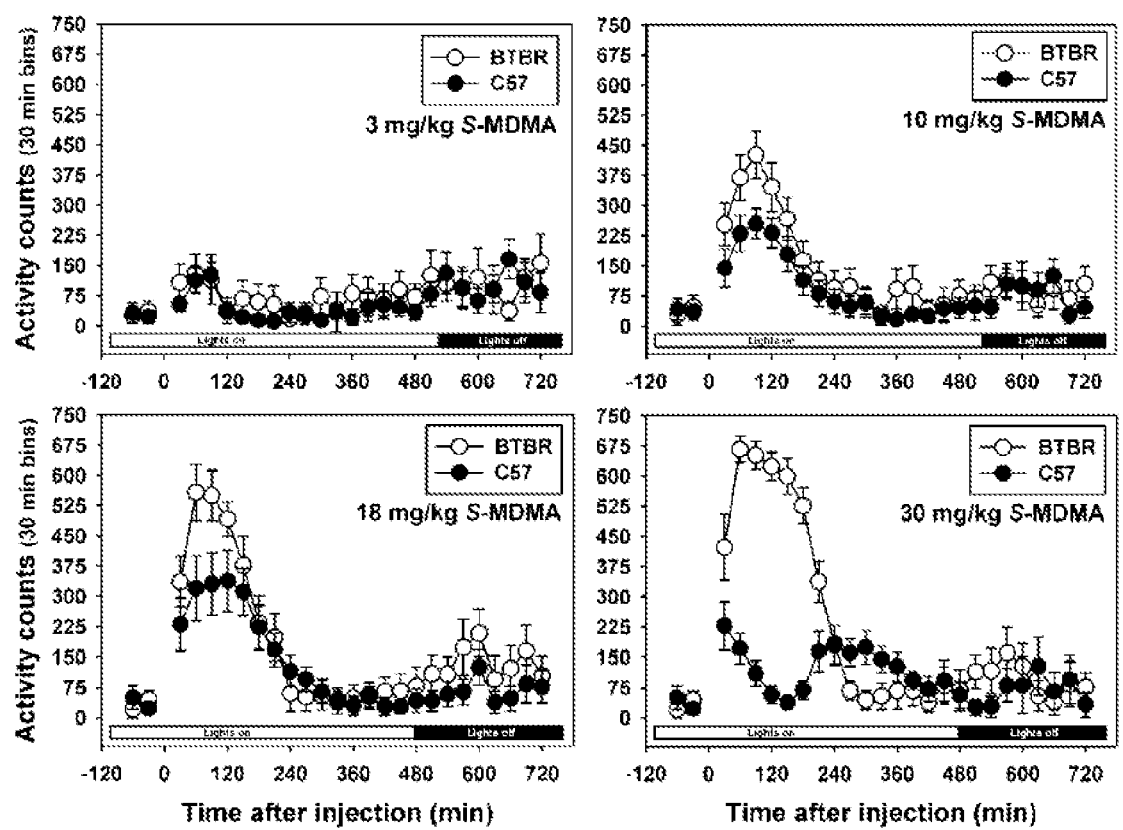
FIG. 17 shows the effect of various doses (3 mg/kg, 10 mg/kg, 18 mg/kg, 30 mg/kg) of S-MDMA (e.g comparative composition 3) on locomotor activity in C57 mice (filled circles) and BTBR mice (open circles). Symbols represent group means, and error bars represent SEM unless the SEM is smaller than the size of the symbol. The bar at the bottom of each panel indicates when room lights were on or off.

FIG. 17 shows the effect of various doses of S-MDMA (e.g. comparative composition 3) on locomotor activity in C57 mice (filled circles) and BTBR mice (open circles). The pattern of locomotor activity across the time course for the C57 mice administered 30 mg/kg is consistent with motor stereotypy: an initial increase in activity is observed, followed by suppression of locomotion, then a "late phase" increase in activity as S(+)-MDMA is cleared and eliminated. No evidence of motor stereotypy in the BTBR was observed at any dose.

Locomotor Effects of Increasing Doses of Fentanyl in C57 and BTBR Mice.

Figure 18:
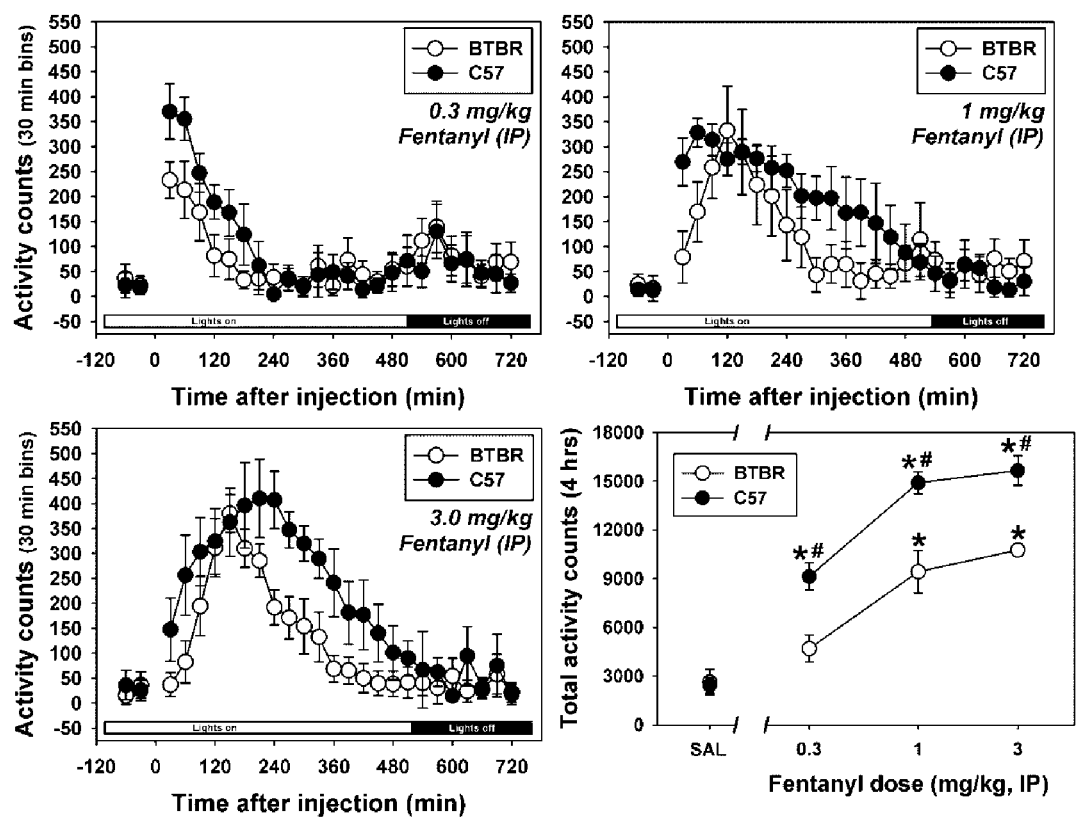
FIG. 18 shows the locomotor effects of 0.3 mg/kg (top left), 1 mg/kg (top right graph), 3 mg/kg of u-opioid agonist Fentanyl in C57 mice (filled circles) vs BTBR mice (open circles). Bottom right graph depicts dose-effect functions for locomotor effects of total activity for 4 h after injection. Symbols represent group means, and error bars represent SEM unless the SEM is smaller than the size of the symbol. Dose is expressed in mg/kg and presented on a log scale. Asterisks indicate significant differences from saline, while pound signs indicate significant differences between strains, within dose.

FIG. 18 shows the locomotor effects of 0.3 mg/kg (top left), 1 mg/kg (top right graph), 3 mg/kg of u-opioid agonist Fentanyl in C57 mice (filled circles) vs BTBR mice (open circles). Note that unlike the pattern of data observed with racemic MDMA (e.g. comparative composition 1) and S(+)-MDMA (e.g. comparative composition 1), each dose of fentanyl elicited more locomotor activity in the C57 mice than in the BTBR mice. Thus, BTBR mice are not more sensitive to locomotor effects of all drugs but are specifically sensitive to psychostimulant effects of MDMA-like drugs.
Locomotor Effects of Increasing Doses of Psychostimulant S-Methamphetamine in C57 and BTBR Mice.

Figure 19:
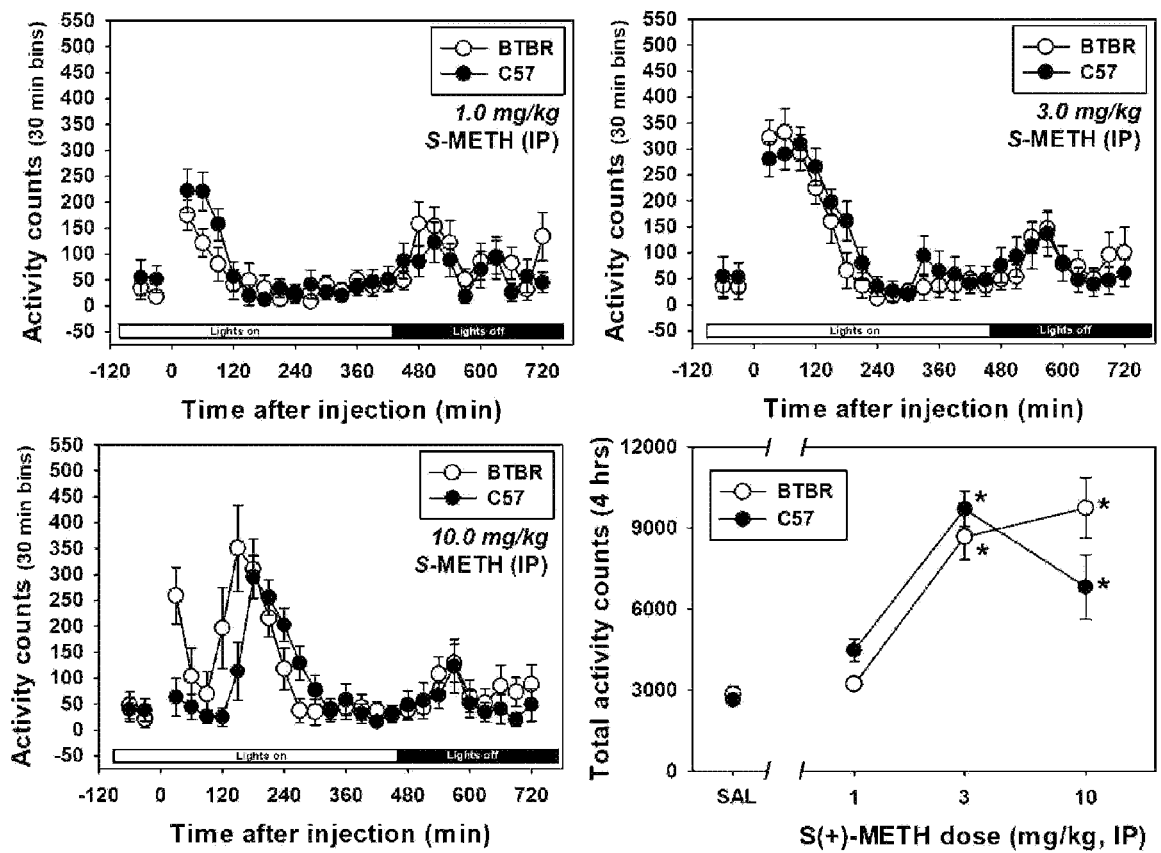
FIG. 19 shows the locomotor effects of 0.3 mg/kg (top left), 1 mg/kg (top right graph), 3 mg/kg of S-methamphetamine in C57 mice (filled circles) vs BTBR mice (open circles). The bottom right graph depicts dose-effect functions for locomotor effects of total activity for 4 h after injection. Symbols represent group means, and error bars represent SEM unless the SEM is smaller than the size of the symbol. Dose is expressed in mg/kg and presented on a log scale.

FIG. 19 shows the locomotor effects of 0.3 mg/kg (top left), 1 mg/kg (top right graph), 3 mg/kg of S-methamphetamine in C57 mice (filled circles) vs BTBR mice (open circles). Note that unlike the pattern of data observed with racemic MDMA and S(+)-MDMA, there were no significant strain differences observed at any dose of S(+)-METH. Thus, BTBR mice are not more sensitive to locomotor effects of all drugs but are specifically sensitive to psychostimulant effects of MDMA-like drugs. (Time-activity curve for 0.3 mg/kg S(+)-methamphetamine not shown because effects were not different from saline.)

Core Temperature Effect and Locomotor Activity Effect of 10 mg/kg of Racemic MDMA Vs S-MDMA Vs R-MDMA Vs Comparative Composition 2(i)

Figure 20:
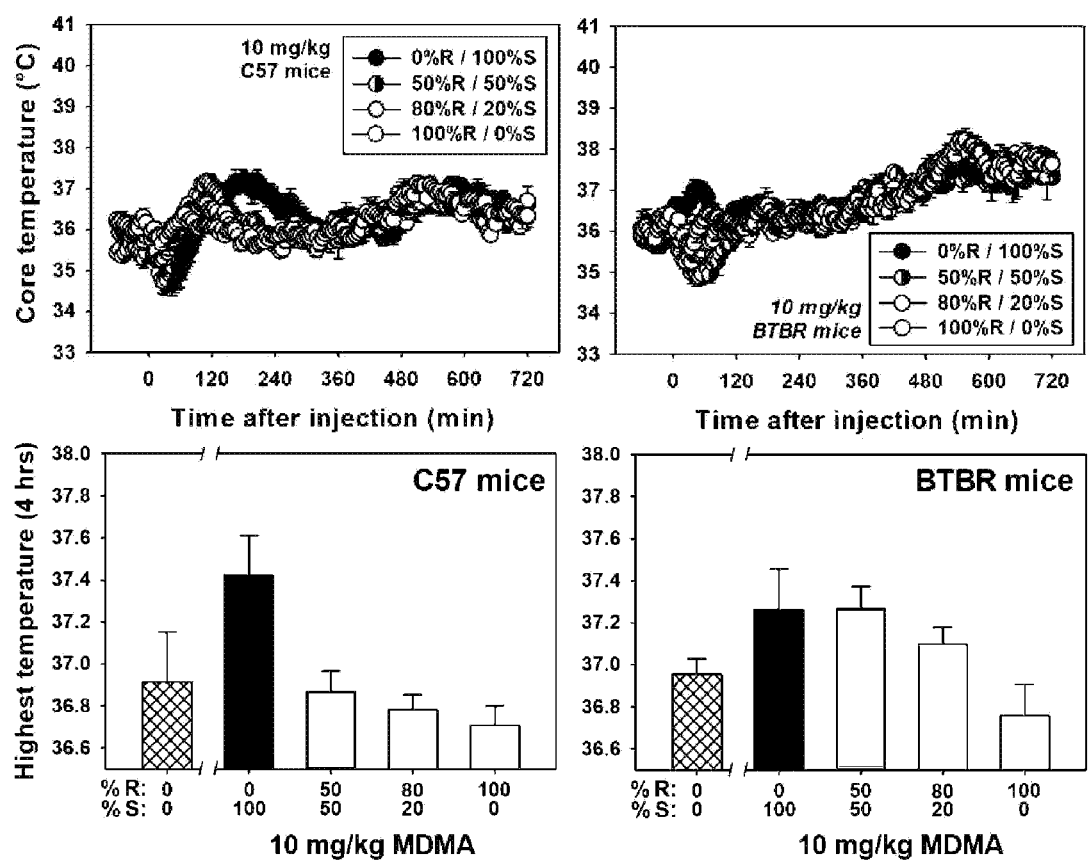
FIG. 20 shows the effects of 10 mg/kg of MDMA at a ratio of 0% R(−)-MDMA to 100% S(+)-MDMA (black circles, e.g., comparative composition 3), 50% R(−)-MDMA to 50% S(+)-MDMA (half white/half black circles, e.g., comparative composition 1), 80% R(−)-MDMA to 20% S(+)-MDMA (gray circles, e.g., exemplary composition 2(i)), or 100% R(−)-MDMA to 0% S(+)-MDMA (white circles, e.g., exemplary composition 7) on core temperature in C57 mice (left) and in BTBR mice (right). Symbols represent group means, and error bars represent SEM unless the SEM is smaller than the size of the symbol. Bottom panels represent core temperature summary figures, collapsing the time-activity data from the above figures (from 0 to 240 minutes) into bars in order to allow visualization of the impact of the MDMA enantiomers on core temperature.

FIG. 20 shows the effects of 10 mg/kg of MDMA at a ratio of 0% R(−)-MDMA to 100% S(+)-MDMA (black circles) (e.g., comparative composition 3), 50% R(−)-MDMA to 50% S(+)-MDMA (half white/half black circles) (e.g., comparative composition 1), 80% R(−)-MDMA to 20% S(+)-MDMA (gray circles) (e.g., exemplary composition 2(i)), or 100% R(−)-MDMA to 0% S(+)-MDMA (white circles) (e.g., exemplary composition 7) on core temperature in C57 mice (left) and in BTBR mice (right). For C57 mice (left), pure S(+)-MDMA (e.g., comparative composition 3) elicited an increase in temperature, but neither of the mixtures (e.g., exemplary composition 2(i)) nor pure R(−)-MDMA (e.g., exemplary composition 7) elicited significant effects on the core temperature at this dose. There looks to be a trend toward decreasing temperature as a function of the presence of R(−)-MDMA, whether these are physiologically relevant for the human populations remains to be evaluated.

For BTBR mice (right), pure S(+)-MDMA (e.g., comparative composition 3) elicited a similar increase in temperature, and the less S(+)-enantiomer present in the mixtures, the smaller the observed effect. This pattern is repeated at the 30 mg/kg dose below where significant differences are observed.

Figure 21:
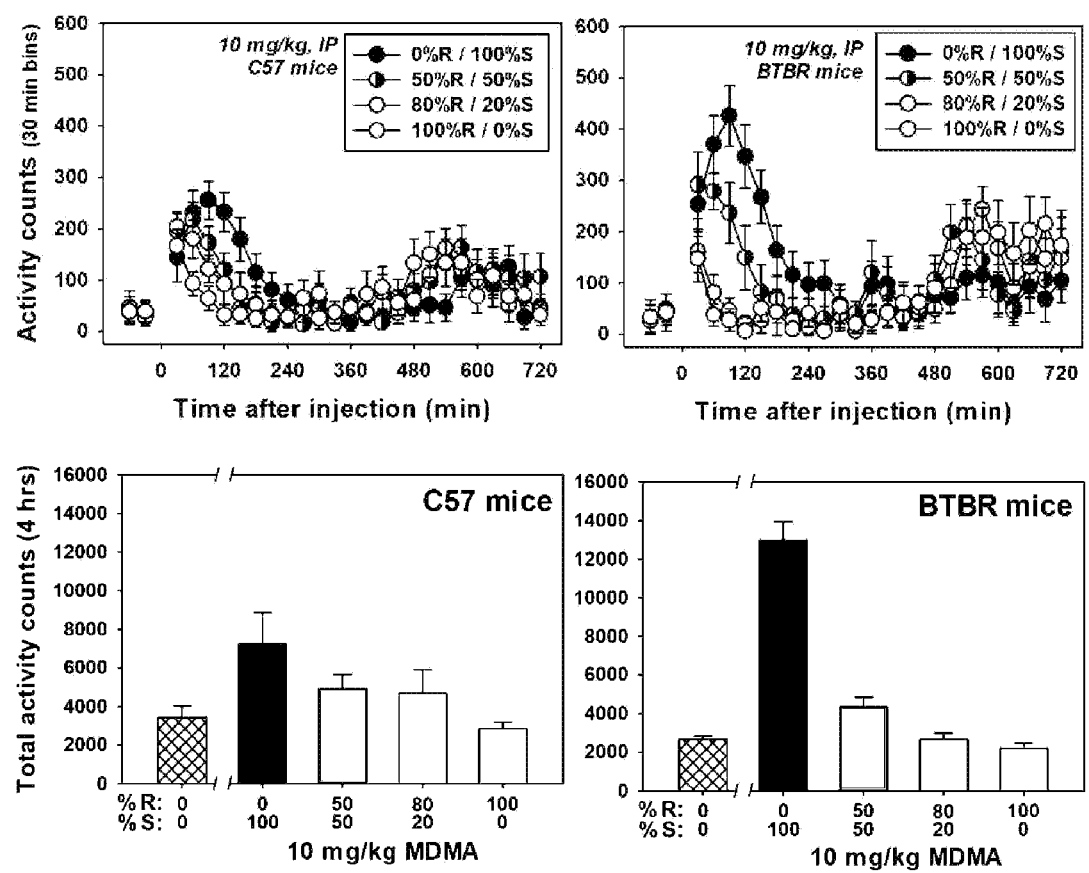
FIG. 21 shows the effects of 10 mg/kg of MDMA at a ratio of 0% R(−)-MDMA to 100% S(+)-MDMA (black circles, e.g., comparative composition 3), 50% R(−)-MDMA to 50% S(+)-MDMA (half white/half black circles, e.g., comparative composition 1), 80% R(−)-MDMA to 20% S(+)-MDMA (gray circles, e.g., exemplary composition 2(i)), or 100% R(−)-MDMA to 0% S(+)-MDMA (white circles, e.g., exemplary composition 7), on locomotor activity in c57 mice (left) and BTBR mice (right). Symbols represent group means, and error bars represent SEM unless the SEM is smaller than the size of the symbol. Bottom panels represent locomotor summary figures, collapsing the time-activity data from the above figures (from 0 to 240 minutes) into bars in order to allow visualization of the impact of the MDMA enantiomers on motor activity.

FIG. 21 shows the effects of 10 mg/kg of MDMA at a ratio of 0% R(−)-MDMA to 100% S(+)-MDMA (black circles) (e.g., comparative composition 3), 50% R(−)-MDMA to 50% S(+)-MDMA (half white/half black circles) (e.g., comparative composition), 80% R(−)-MDMA to 20% S(+)-MDMA (gray circles) (e.g., exemplary composition 2(i)), or 100% R(−)-MDMA to 0% S(+)-MDMA (white circles) (e.g., exemplary composition 7), on locomotor activity in c57 mice (left) and BTBR mice (right). For C57 mice (left), pure S(+)-MDMA (e.g., comparative composition 3), elicits the greatest locomotor stimulation, and lesser hyperactivity is observed with the racemic mixture (e.g., comparative composition 1), and the 80R/20S mixture (e.g., exemplary composition 2(i)) at this dose. Pure R(−)-MDMA (e.g., exemplary composition 7) did elicit significant motor stimulation at this dose. For BTBR mice (right), pure S(+)-MDMA (e.g., comparative composition 3) elicited a substantially large stimulation in motor activity, and the less S(+)-enantiomer present in the mixtures, the less activity was observed. For pure R(−)-MDMA (e.g., exemplary composition 7) and for the 80/20 mixture (e.g., exemplary composition 2(i)), no significant motor stimulation was observed at this dose.

Surprisingly, despite the strong locomotor stimulant effect with S-MDMA (e.g., comparative composition 3) in BTBR mice (FIG. 21), the core temperature did not differ much from that observed with Racemic MDMA (e.g., comparative composition 1) (see FIG. 20).

Core Temperature Effect and Locomotor Activity Effect of 30 mg/kg of Racemic MDMA Vs S-MDMA Vs R-MDMA Vs Exemplary Composition 2(i)

Figure 22:
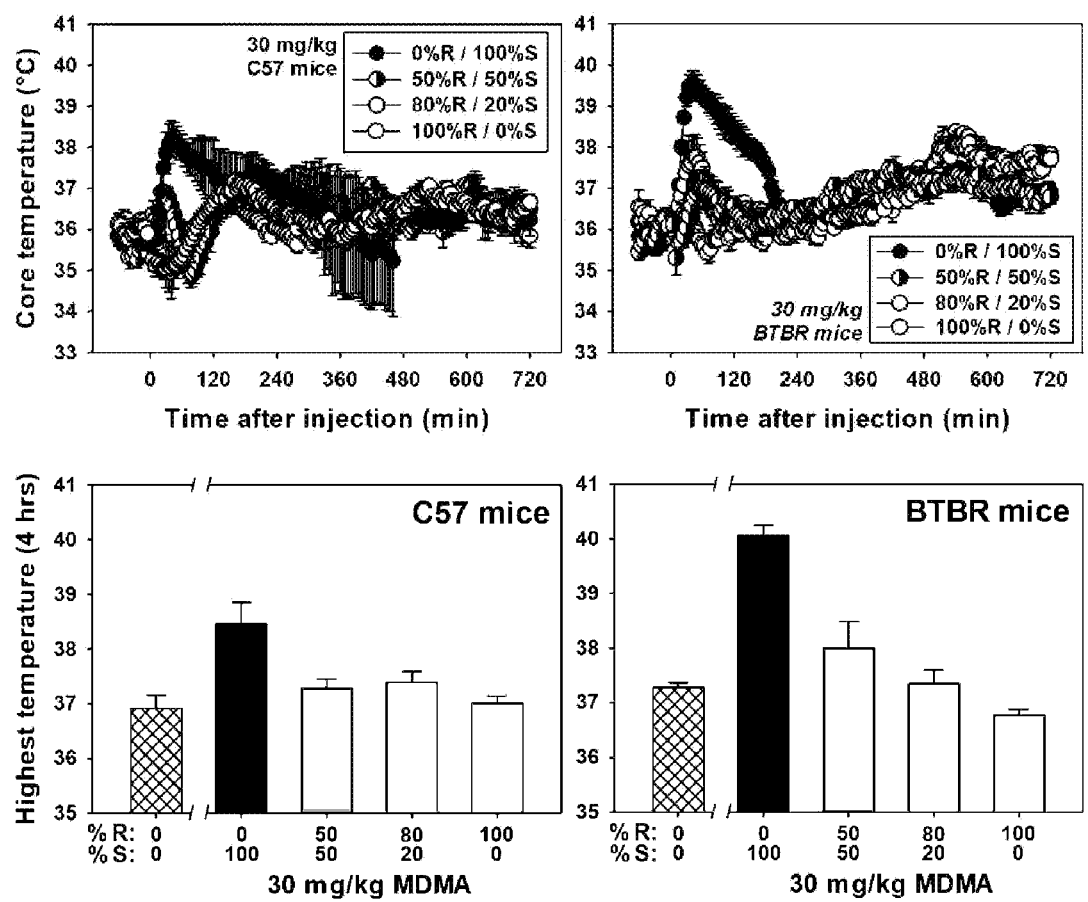
FIG. 22 shows the effects of 30 mg/kg of MDMA at a ratio of 0% R(−)-MDMA to 100% S(+)-MDMA (black circles, e.g., comparative composition 3), 50% R(−)-MDMA to 50% S(+)-MDMA (half white/half black circles, e.g., comparative composition 1), 80% R(−)-MDMA to 20% S(+)-MDMA (gray circles, e.g., exemplary composition 2(i)), or 100% R(−)-MDMA to 0% S(+)-MDMA (white circles, e.g., exemplary composition 7), on core temperature in C57 mice (left) and in BTBR mice (right). Symbols represent group means, and error bars represent SEM unless the SEM is smaller than the size of the symbol. Bottom panels represent core temperature summary figures, collapsing the time-activity data from the above figures (from 0 to 240 minutes) into bars in order to allow visualization of the impact of the MDMA enantiomers on core temperature.

FIG. 22 shows the effects of 30 mg/kg of MDMA at a ratio of 0% R(−)-MDMA to 100% S(+)-MDMA (black circles) (e.g., exemplary composition 7), 50% R(−)-MDMA to 50% S(+)-MDMA (half white/half black circles) (e.g., comparative composition 1), 80% R(−)-MDMA to 20% S(+)-MDMA (gray circles) (e.g., exemplary composition 2(i)), or 100% R(−)-MDMA to 0% S(+)-MDMA (white circles) (e.g., exemplary composition 7), on core temperature in C57 mice (left) and in BTBR mice (right). For C57 mice (left), pure S(+)-MDMA elicits significant hyperthermia, but neither of the mixtures nor pure R(−)-MDMA elicited significant effects on the core temperature at this dose.

For BTBR mice (right), pure S(+)-MDMA (e.g., exemplary composition 3), elicited a large hyperthermic response, and the less S(+)-enantiomer present in the mixtures, the less hyperthermia was observed. For pure R(−)-MDMA (e.g., exemplary composition 7) and for the 80/20 mixture (e.g., exemplary composition 2(i), no significant effects on core temperature were observed at this dose.

Figure 23:
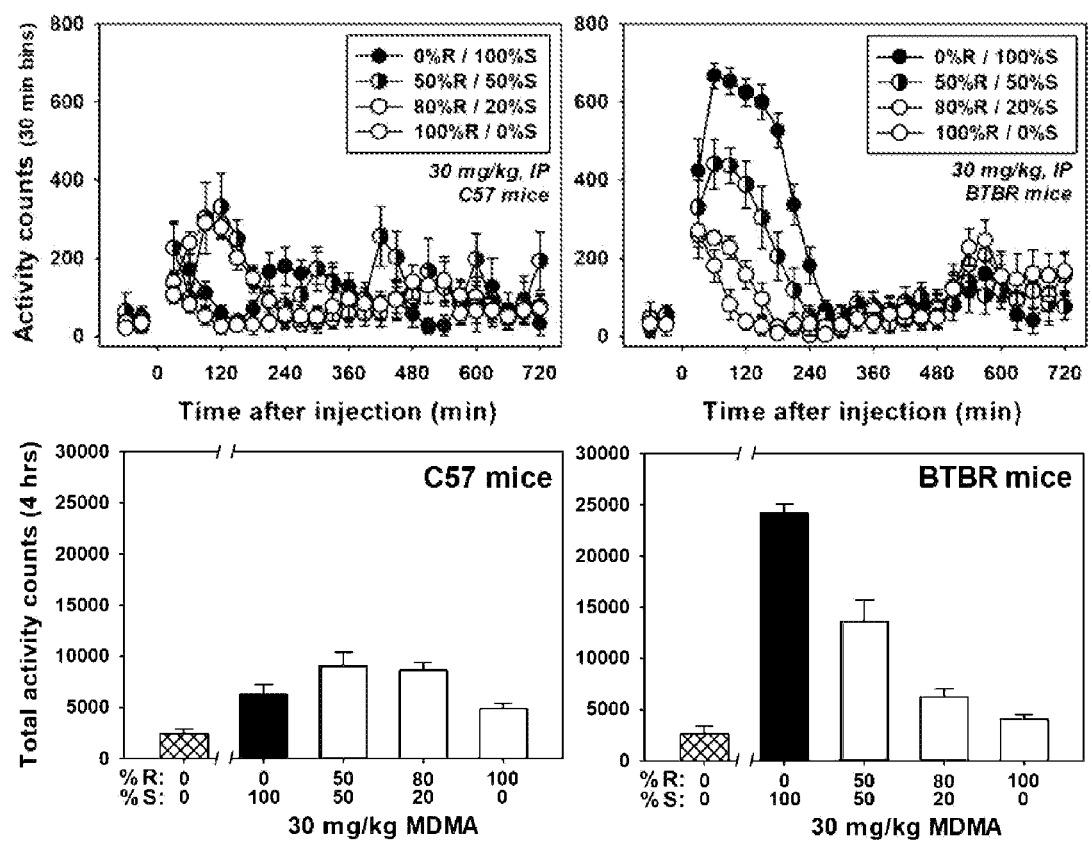
FIG. 23 shows the effects of 30 mg/kg of MDMA at a ratio of 0% R(−)-MDMA to 100% S(+)-MDMA (black circles, e.g., comparative composition 3), 50% R(−)-MDMA to 50% S(+)-MDMA (half white/half black circles) (e.g., comparative composition 1), 80% R(−)-MDMA to 20% S(+)-MDMA (gray circles, e.g., exemplary composition 2(i)), or 100% R(−)-MDMA to 0% S(+)-MDMA (white circles, e.g., exemplary composition 7) on locomotor activity in C57 mice (top left) and in BTBR mice (top right). Symbols represent group means, and error bars represent SEM unless the SEM is smaller than the size of the symbol. The bottom panels represent locomotor summary figures, collapsing the time-activity data from the above figures (from 0 to 240 minutes) into bars to allow visualization of the impact of the MDMA enantiomers on motor activity.

FIG. 23 shows the effects of 30 mg/kg of MDMA at a ratio of 0% R(−)-MDMA to 100% S(+)-MDMA (black circles) (e.g., comparative composition 3), 50% R(−)-MDMA to 50% S(+)-MDMA (half white/half black circles) (e.g., comparative composition 1), 80% R(−)-MDMA to 20% S(+)-MDMA (gray circles) (e.g., exemplary composition 2(i)), or 100% R(−)-MDMA to 0% S(+)-MDMA (white circles) (e.g., exemplary composition 7) on locomotor activity in C57 mice (top left) and in BTBR mice (top right). 30 mg/kg of 100% S(+)-MDMA (e.g., comparative composition 3), elicits locomotor stereotypy in C57 mice, characterized by an initial increase in activity, then depression as animals enter stereotypy, then a "second phase" increase in activity as the drug is cleared and eliminated around 240 min after injection. In contrast, the enantiomer mixtures (e.g., exemplary composition 2(i)) elicit only time-dependent increases in motor activity. Interestingly, no stereotypy was observed in the BTBR mice For C57 mice (left graph), the racemic mixture (e.g., comparative composition 1) and the 80R/20S mixture (e.g., exemplary composition 2(i)) elicit more activity than the pure S(+)-MDMA (e.g., comparative composition 3), due to stereotypic effects of the S(+)-enantiomer at this dose. Pure R(−)-MDMA (e.g., exemplary composition 7) did not elicit significant motor stimulation at this dose.

For BTBR mice (right), pure S(+)-MDMA elicited a large stimulation in motor activity, and the less S(+)-enantiomer present in the mixtures, the less activity was observed. For pure R(−)-MDMA (e.g., exemplary composition 7), no significant motor stimulation was observed at this dose.

Locomotor Effects of Saline or Various Doses of Racemic MDMA and S-MDMA in C57 and BTBR Mice.

Figure 24:
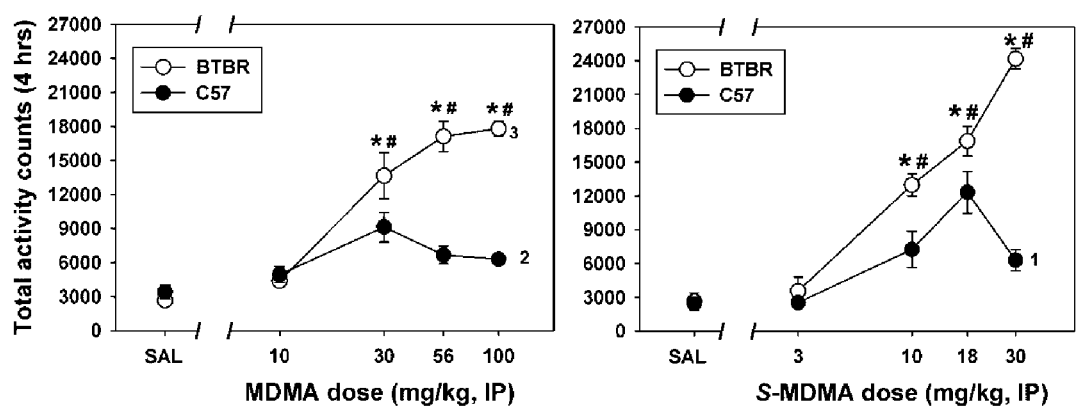
FIG. 24 shows the locomotor effects of saline or various doses of Racemic MDMA (left panel, e.g., comparative composition 1) or S-MDMA (right panel, e.g., comparative composition 3) in C57 (filled circles) and BTBR (open circles) mice. Symbols represent group means, and error bars represent SEM unless the SEM is smaller than the size of the symbol. Dose is expressed in mg/kg and presented on a log scale. Numerals adjacent to points indicate the number of animals that died within 8 hours of drug administration.

FIG. 24 shows the locomotor effects of saline or various doses of Racemic MDMA (left panel) (e.g., comparative composition 1) or S-MDMA (right panel) (e.g., comparative composition 3) in C57 (filled circles) and BTBR (open circles) mice. Both racemic MDMA (e.g., comparative composition 1) and S(+)-MDMA (e.g., comparative composition 3) elicit a classical "inverted U-shaped" dose-effect curve as large doses elicit motor stereotypy which results in less total ambulatory activity than observed at intermediate doses. Interestingly, the dose-effect curve for the BTBR mice does not follow this biphasic pattern for racemic MDMA.

Summary

In a Pilot Phase 2 clinical trial, Alicia Danforth, and Charles Grobb (Danforth et al., Psychopharmacology (Berl). 2018; 235(11): 3137-3148), have demonstrated rapid and durable improvement in social anxiety symptoms in autistic adults following MDMA-assisted psychotherapy. However, Racemic MDMA also results in a rise in core temperature and cardiovascular events as demonstrated by other researchers. The aim of the present study was to evaluate the safety profile of our exemplary non-racemic compositions of the application compared to the individual (R) and (S) enantiomers of MDMA and Racemic MDMA.

The following findings were found:

Both racemic MDMA (e.g., comparative composition 1) and S(+)-MDMA (e.g., comparative composition 3) elicit a classical "inverted U-shaped" dose-effect curve as large doses elicit motor stereotypy which results in less total ambulatory activity than observed at intermediate doses. Interestingly, the dose-effect curve for the BTBR mice does not follow this biphasic pattern for racemic MDMA (see FIG. 24)

In comparison to 10 mg/kg, BTBR elicits a strong hyperthermic response to 30 mg/kg S-MDMA (e.g., comparative composition 3). Racemic MDMA (e.g., comparative composition 1) at both doses (10 mg/kg and 30 mg/kg) results in an increase in temperature but is not as significant as S-MDMA. (see FIG. 22).

Exemplary composition 2(i)) (regardless of the dose) and Saline have a response to change in temperature in BTBR and C57 mice (see FIG. 20 and FIG. 22).

These results in combination with the Social Preference data described in Part A above elucidate that upon administration of non-racemic composition of the application such as exemplary composition 2(i)) in BTBR mice, the mice overcome the inherent social anxiety without having severe adverse events such as hyperthermia. Thereby non-racemic compositions of the application such as exemplary composition result in a relatively safer use of MDMA.

While the present application has been described with reference to examples, it is to be understood that the scope of the claims should not be limited by the embodiments set forth in the examples, but should be given the broadest interpretation consistent with the description as a whole.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

The invention claimed is:

1. A non-racemic mixture comprising a compound of Formula (R)-I, or a salt and/or solvate thereof, and a compound of Formula (S)-I, or a salt and/or solvate thereof:

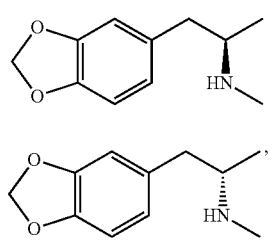

and wherein the non-racemic mixture comprises about 70% to about 80% by enantiomeric equivalents of the compound of Formula (R)-I, or a salt and/or solvate thereof, and about 20% to about 30% by enantiomeric equivalents of the compound of Formula (S)-I, or a salt and/or solvate thereof.

2. The non-racemic mixture of claim 1 comprising about 70% to about 75% by enantiomeric equivalents of the compound of Formula (R)-I, or a salt and/or solvate thereof, and 25% to about 30% by enantiomeric equivalents of the compound of Formula (S)-I, or a salt and/or solvate thereof.

3. The non-racemic mixture of claim 1 comprising about 75% to about 79.9% by enantiomeric equivalents of the compound of Formula (R)-I, or a salt and/or solvate thereof, and about 20.1% to about 25% by enantiomeric equivalents of the compound of Formula (S)-I.

4. The non-racemic mixture of claim 1 comprising about 80% by enantiomeric equivalents of the Formula (R)-I, or a salt and/or solvate thereof, and about 20% by enantiomeric equivalents of the Formula (S)-I, or a salt and/or solvate thereof.

5. The non-racemic mixture of claim 1 comprising about 70% by enantiomeric equivalents of the Formula (R)-I, or a salt and/or solvate thereof, and about 30% by enantiomeric equivalents of the Formula (S)-I, or a salt and/or solvate thereof.

6. The non-racemic mixture of claim 1, wherein the compounds of Formula (R)-I and (S)-I are both in acid salt form.

7. A pharmaceutical composition comprising a non-racemic mixture of a compound of Formula (R)-I, or a salt and/or solvate thereof, and a compound of Formula (S)-I, or a salt and/or solvate thereof:

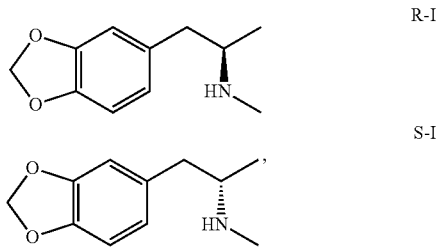

wherein the non-racemic mixture comprises about 70% to about 80% by enantiomeric equivalents of the compound of Formula (R)-I, or a salt and/or solvate thereof, and about 20% to about 30% by enantiomeric equivalents of the compound of Formula (S)-I, or a salt and/or solvate thereof, and the composition further comprises one or more pharmaceutically acceptable carriers.

8. The compositions of claim 7, wherein the composition is formulated for oral administration.

9. The composition of claim 7, wherein the composition is formulated for intranasal administration.

10. The composition of claim 7, wherein the composition is formulated for sublingual administration.

11. The composition of claim 7, wherein the composition comprises about 40 mg to about 180 mg of the non-racemic mixture.

12. The composition of claim 7, wherein the composition comprises about 40 mg, 60 mg, 75 mg, 80 mg, 100 mg, 120 mg or 125 mg of the non-racemic mixture.

13. The composition of claim 7, wherein the composition comprises about 0.05 wt % to about 99 wt % or about 0.10 wt % to about 70 wt %, of the non-racemic mixture, and from about 1 wt % to about 99.95 wt % or about 30 wt % to about 99.90 wt % of one or more pharmaceutically acceptable carriers, all percentages by weight being based on the total composition.

* * * * *